(12) United States Patent
Hoon

(10) Patent No.: US 6,673,914 B1
(45) Date of Patent: Jan. 6, 2004

(54) HUMAN TUMOR-ASSOCIATED GENE

(75) Inventor: David S. B. Hoon, Los Angeles, CA (US)

(73) Assignee: John Wayne Cancer Institute, Santa Monica, CA (US)

( * ) Notice: Subject to any disclaimer, the term of this patent is extended or adjusted under 35 U.S.C. 154(b) by 0 days.

(21) Appl. No.: 09/234,685

(22) Filed: Jan. 21, 1999

Related U.S. Application Data

(60) Provisional application No. 60/072,126, filed on Jan. 22, 1998.

(51) Int. Cl.[7] .............................. C07H 21/04
(52) U.S. Cl. ................. 536/23.5; 536/23.1; 435/320.1; 435/243; 435/358; 530/350
(58) Field of Search ................. 536/23.1, 23.5, 536/24.5, 24.1, 24.37; 530/350; 435/320.1, 325, 243, 252.3, 252.33, 254.1, 358

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,196,265 A | 4/1980 | Koprowski et al. |
| 4,215,051 A | 7/1980 | Schroeder et al. |
| 4,275,149 A | 6/1981 | Litman et al. |
| 4,277,437 A | 7/1981 | Maggio |
| 4,340,535 A | 7/1982 | Voisin et al. |
| 4,366,241 A | 12/1982 | Tom et al. |
| 4,472,509 A | 9/1984 | Gansow et al. |
| 4,554,101 A | 11/1985 | Hopp |
| 4,683,195 A | 7/1987 | Mullis et al. |
| 4,683,202 A | 7/1987 | Mullis |
| 4,740,463 A | 4/1988 | Weinberg et al. |
| 4,800,159 A | 1/1989 | Mullis et al. |
| 4,816,567 A | 3/1989 | Cabilly et al. |
| 4,867,973 A | 9/1989 | Goers et al. |
| 4,883,750 A | 11/1989 | Whiteley et al. |
| 5,021,236 A | 6/1991 | Gries et al. |
| 5,138,045 A | 8/1992 | Cook et al. |
| 5,262,311 A | 11/1993 | Pardec et al. |
| 5,279,721 A | 1/1994 | Schmid |
| 5,342,774 A | 8/1994 | Boon et al. |
| 5,565,332 A | 10/1996 | Hoogenboom et al. |
| 5,627,054 A * | 5/1997 | Gillespie, deceased |
| 5,633,365 A | 5/1997 | Stokke et al. |
| 5,665,549 A | 9/1997 | Pinkel et al. |
| 5,693,762 A | 12/1997 | Queen et al. |
| 6,054,289 A * | 4/2000 | Moore |

FOREIGN PATENT DOCUMENTS

| | | |
|---|---|---|
| EP | 329822 A2 | 8/1989 |
| EP | 431523 | 6/1991 |
| EP | 329822 B1 | 6/1994 |
| GB | 2202328 | 7/1991 |
| WO | WO 87/06270 | 10/1987 |
| WO | WO 88/10315 | 12/1988 |
| WO | WO 89/06700 | 7/1989 |
| WO | WO 89/09284 | 10/1989 |
| WO | WO 94/10343 | 5/1994 |
| WO | WO 94/23050 | 10/1994 |
| WO | WO 95/10265 | 4/1995 |

OTHER PUBLICATIONS

Sambrook et al Molecular Cloning, A Laboratory Manual, pp. 13.15 and 13.17, 1989.*

(List continued on next page.)

*Primary Examiner*—Larry Helms
(74) *Attorney, Agent, or Firm*—Fulbright & Jaworski

(57) ABSTRACT

The present invention describes a novel tumor marker antigen encoded by a gene designated as HOJ-1 (SEQ ID NO:1). In specific embodiment, the nucleic acid sequences disclosed herein are for used in the diagnosis and prognosis of cancer. Also provided are related protein and antibody compositions and various methods of use thereof, including methods for cancer diagnosis and treatment.

20 Claims, 11 Drawing Sheets

OTHER PUBLICATIONS

Bonaldo et al., Genome Res. 6:791–806, 1996*

Lewin, Genes IV, Oxford University Press, p. 810, 1990.*

Alberts et al., Molecular Biology of the Cell, third Ed. Carland Publishing, Inc. pp. 464–465, 1994.*

The Promega Catalog, Nucleic Acids, 1994.*

Hillier et al., "zd67g05.r1 soares fetal heart NbHH19W homo sapiens cDNA clone 345752 5'," Database EMBL–E–MEST13 entry HS526369, Acc. No. W76526, 1996.

Hoon, et al., "Human carcinoma associated HOJ–1 mRNA, complete eds." Database EMBL–R57U005, Entry/Acc. No. U82396, Dec. 15, 1998.

Marra et al., "mm45h12.r1 stratagene mouse melanoma (#937312) mus musculus cDNA clone 524519 5' similar to TR:G184390 G184390 putative transcritptional regulatory protein hrc 1," EMBL–EMEST19 entry Mma68103, Jun. 23, 1996.

Abbondanzo et al., "Prognostic significance of immunocytochemically determined ps2 in axillary nodenegative breast carcinoma," *Breast Cancer Res. Treat.*, 16:182, Abstract #151, 1990.

Alfthan et al., "Elevation of free β subunit of human choriogonadotropin and core β fragment of human choriogonadotropin in the serum and urine of patient with malignant pancreatic and biliary disease," *Cancer Res.*, 52:4628–4633, 1992.

Allred et al., "Comprehensive evaluation of prognostic factors by immunocytochemistry on extremely small samples (50 mg) of "pulverized" breast carcinomas," *Breast Cancer Res. Treat.*, 16:182, Abstract #149, 1990.

Ando et al., "Ganglioside gm2 on the K562 cell line is recognized as target structure by human natural killer cells," *Int. J. Cancer*, 40:12–17, 1987.

Bitter et al., "Expression and secretion vectors for yeast," *Methods in Enzymol*, 153:516–544, 1987.

Brown et al., "Prognostic significance and clinical–pathological correlations of cell–cycle kinetic measured by KI–67 immunocytochemistry in axillary node–negative carinoma of the breast," *Breast Cancer Res. Treat.*, 16:192, Abstract #191, 1990.

Capaldi et al., "Changes in order of migration of polypeptides in complex III and cytochrome c oxidase under different conditions of sds polyacrylamide gel electrophoresis," *Biochem. Biophys. Res. Comm.*, 74(2):425–433, 1977.

Carubia et al., "Gangliosides of normal and neoplastic human melanocytes," *Biochem. Biophys. Res. Commun.*, 120:500–504, 1984.

Chien et al., "The two–hybrid system: a method to identify and clone genes for proteins that interact with a protein of interest," *Proc. Nat'l. Acad. Sci. USA*, 88:9578–9582, 1991.

Chinault and Carbon, "Overlap hybridization screening: isolation and characterization of overlapping DNA fragments surrounding the leu2 gene on yeast chromosome III," *Gene*, 5:111–126, 1979.

Cohen, "Naked DNA points way to vaccines," *Science*, 259:1691–1692, 1993.

Cole et al., "Detection of the free beta subunit of human chorionic gonadotropin (HCG) in cultures of normal and malignant trophoblast cells, pregnancy sera, and sera of patients with choriocarcinoma," *Endocrinology*, 113:1176–1178, 1983.

Datta et al., "Sensitive detection of occult breast cancer by the reverse–transcriptase polymerase chain reaction," *J. Clin. Oncol.*, 12:475–482, 1994.

Denton et al., "A study of adhesion molecules as markers of progression in maglignant melanoma," *J. Pathol*, 167(2):187–191, 1992.

Diamond et al., "A new method to assess metastatic potential of human prostate cancer: relative nuclear roundness," *J. Urol.*, 128:729–734, 1982.

Donahue et al., "A delayed–early gene activated by fibroblast growth factor–1 encodes a protein related to aldose reductase," *J. Biol. Chem.*, 269:8604–8609, 1994.

Dzau et al., "Fusigenic viral liposome for gene therapy in cardiovascular diseases," *Proc. Nat'l. Acad. Sci. USA*, 93:11421–11425, 1996.

Elder et al., "Antigenic profile of tumor progression stages in human melanocytic nevi and melanomas," *Cancer Res.*, 49:5091–5096, 1989.

Fearon et al., "Cancer cachexia: influence of systemic ketosis on substrate levels and nitrogen metabolism," *Am J Clin Nutr*, 47(1):42–48, 1988.

Fink et al., "Localization of the gene encoding the putative human HLA class II associated protein (PHAPI) to chromosome 15q22.3–q23 by fluorescence in situ hybridization" *Genomics*, 29:309–310, 1995.

Furukawa et al., GD2 ganglioside on human T–lymphotropic virus type I–infected T cells: possible activation of β–1,4–N–acetylgalactosaminyltransferase gene by p40$^{tax}$ *Proc. Nat'l. Acad. Sci. USA*, 90:1972–1976, 1993.

Fynan et al., "DNA vaccines: protective immunizations by parenteral, mucosal, and gene–gun inoculations," *Proc. Nat'l. Acad. Sci. USA*, 90:11478–11482, 1993.

Gaugler et al., "Human gene MAGE–3 codes for an antigen recognized on a melanoma by autologous cytolytic T lymphocytes," *J. Exper. Med.*, 179:921–930, 1994.

Gomella et al., "Reverse transcriptase polymerase chain reaction for prostate specific antigen in the management of prostate cancer," *J. Urolology*, 158:326–337, 1997.

Hollingsworth et al., "Expression of muc1, muc2, muc3, and muc4 mucin mRNAs in human pancreatic and intestinal tumor cell lines," *Int J Cancer*, 57(2):198–203, 1994.

Hoon et al., "Detection of metastatic breast cancer by β–hCG polymerase chain reaction," *Int J Cancer*, 69(5):369–74, 1996.

Hoon et al., "Detection of occult melanoma cells in blood with a multiple–maker polymerase chain reaction assay," *J. Clin. Oncol.*, 13:2109–2116, 1995.

Hoon et al., "Melanoma paitents immunized with melanoma cell vaccine induce antibody responses to recombinant MAGE–1 antigen," *J. Immunol.*, 154:730–737, 1995.

Hoon et al., "Aberrant expression of gangliosides in human renal cell carcinomas," *J. Urol.* , 150(6):2013–2018, 1993.

Hoon et al., "Ganglioside gm2 expression on human melanoma cells correlates with sensitivity to lymphokine–activated killer cells," *Int. J. Cancer*, 43:857–862, 1989.

Kohler and Milstein, "Derivation of specific antibody–producing tissue culture and tumor lines by cell fusion," *Eur. J. Immunol.* 6:511–519, 1976.

Kohler and Milstein, "Continuous cultures of fused cells secreting antibody of predefined specificity," *Nature*, 256:495–497, 1975.

Kuo et al., "Assessment of Messenger RNA of β1→4–N–acetylgalactosaminyl–transferase as a molecular marker of metastatic melanoma," *Clin. Cancer Res.*, 4:411–418, 1998.

Kwoh et al., "Transcription–based amplification system and detection of amplified human immunodeficiency virus type 1 with a bead–base sandwich hybridization format," *Proc. Nat. Acad. Sci. USA*, 86(4): 1173–1177, 1989.

Kwon, B.S. "Pigmentation genes: the tyrosinase gene family and the pmel 17 gene family," *J Invest. Dermatol.*, 100(2 Suppl):134S–140S, 1993.

Lehmann et al., "MUC18, a marker of tumor progression in human melanoma, shows sequence similiarity to the neural cell adhesion molecules of the immunoglobulin superfamily," *Proc. Nat'l Acad Sci. USA*, 86:9891–9895, 1989.

Lehmann, et al., "Discrimination between benign and malignant cells of melanocytic lineage by two novel antigens, a glycoprotein with a molecular weight of 113,000 and a protein with a molecular weight of 76,000[1]," *Cancer Res.*, 47:841–845, 1987.

Li et al., "A huntingtin–associated protein enriched in brain with implications for pathology," *Nature*, 378: 398–402, 1995.

Liang and Pardee, "Differential display of eukaryotic messenger RNA by means of the polymerase chain reaction," *Science*, 257: 967–971, 1992.

Liang et al., "Differential display and cloning of messenger RNAs from human breast cancer versus mammary epithelial cells[1]," *Cancer Res.*, 52:6966–6968, 1992.

Lin and Guidotti, "Cloning and expression of a cDNA coding for a rat liver plasma membrane ecto–ATpase," *J. Biol. Chem.*, 264:14408–14414, 1989.

Madersbacher et al, "Human chorionic gonadotropin (hCG) and its free subunits in hydrocele fluids and neoplastic tissue of testicular cancer patients: insights into the in vivo hCG secretion pattern," *Cancer Res.*, 54:5096–5100, 1994.

Marcillac et al., "Free human chorionic gonadotropin β subunit in gonadal and nongonadal neoplasms," *Cancer Res.*, 52:3901–3907, 1992.

McManus et al., "Human chorionic gonadotropin in human neoplastic cells[1]," *Cancer Res.*, 36:3476–3481, 1976.

Melcher and Johnson, "GAL4 interacts with TATA–binding protein and coactivators," *Mol. Cell Biol.*,15:2839–2848, 1995.

Mencinger et al., "Expression analysis and chromosomal mapping of a novel human gene, April, encoding an acidic protein rich in leucines," *Biochim. Biophys. Acta*, 1395:176–180, 1998.

Merrifield, "Solid phase synthesis," *Science*, 232: 341–347, 1986.

Mosmann, "Rapid Colorimetric assay for cellular growth and survival: application to proliferation and cytotoxicity assays," *J. Immunol. Methods*, 65:55–63, 1983.

Nagata et al., "Expression cloning of β1,4 N–Acetylgalactosaminyltransferase cDNAs that determine the epxression of $G_{M2}$ and $G_{D2}$ gangliosides," *J. Biol. Chem*, 267:12082–12089, 1992.

Natali et al., "Immunohistochemical detection of antigen in human primary and metastatic melanomas by the monoclonal antibody 140.240 and its possible prognostic significance," *Cancer*, 59:55–63, 1987.

Nordlund et al., "Pigment cell biology: an historial review," *J. Invest. Dermatol*,. 92:53S–60S, 1989.

Ohara et al., One–sided polymerase chain reaction: the amplification of cDNA, *Proc. Nat'l Acad. Sci. USA*, 86: 5673–5677, 1989.

Pierce and Parsons, "Glycoprotein hormones: structure and function," *Ann. Rev. Biochem.*50:465–495. 1981.

Pinkel, et al., "Cytogenetic analysis using quantitative, high– sensitivity, fluorescence hybridization," *Proc Nat'l Acad Sci U S A*, 83(9):2934–2938, 1986.

Robbins et al., "Recognition of tyrosinase by tumor–infiltrating lymphocytes from a patient responding to immunotherapy," *Cancer Res*, 54(12):3124–3126, 1994.

Rubinstein et al., "Comparison in vitro anticancer–drug–screening data generated with a tetraolium assay versus a protein assay against a diverse panel of human tumor cell lines," *J. Nat'l Cancer Inst.*, 82:1113–1120, 1990.

Sarantou et al., "Melanoma–associated antigens as messenger RNA detection markers for melanoma," *Cancer Res*, 57(7):1371–1376, 1997.

Serrano et al., "A new regulatory motif in cell–cycle control causing specific inhibition of cyclin D/CDK4," *Nature*, 366:704–707, 1993.

Serrano et al., "Inhibition of ras–induced proliferation and cellular transformation by $p16^{INK4}$," *Science*, 267:249–252, 1995.

Sun and Cohen, "Computer–assisted drug discovery–a review," *Gene*, 137:127–132, 1993.

Talmadge et al., "Evolution of the genes for the β subunits of human chorionic gonadotropin and luteinizing hormore," *Nature*, 307:37–40, 1984.

Tam et al., "$S_N2$ deprotection of synthetic peptides with a low concentration of HF in dimethyl sulfide: evidence and application in peptide synthesis[1]," *J. Am. Chem. Soc.*, 105:6442, 1983.

Tang et al., "Genetic immunization in a simple method for eliciting an immune response," *Nature*, 356:152–154, 1992.

Tsuchida et al., "Gangliosides of human melanoma," *J. Nat'l. Cancer Inst.*, 78:45–54, 1987.

Tsuchida et al., "Gangliosides of human melanoma: $G_{M2}$ and tumorigenicity," *J. Nat'l. Cancer Inst.*, 78:55–60, 1987.

Van den Eynde et al., "A new family of genes coding for an antigen recognized by autologous cytolytic T lymphocytes on a human melanoma," *J. Exp. Med.*, 182:689–698, 1995.

Van Der Bruggen et al., "A gene encoding an antigen recognized by cytolytic T lymphocytes on a human melanoma," *Science*, 254:1643–1647, 1991.

Van Pel et al., "Protection against two spontaneous mouse leukemias conferred by immunogenic variants obtained by mutagenesis," *J. Exp. Med.*, 157:1992–2001, 1983.

Vijayasardahi et al., "The melanoma antigen gp75 is the human homologue of the mouse β (Brown) locus gene product," *J. Experimental Medicine*, 171(4):1375–1380, 1990.

Wagner et al., "Antisense gene inhibition by oligonucleotides containing C–5 propyne pyrimidines," *Science*, 260:1510–1513, 1993.

Walker et al., "Isothermal in vitro amplification of DNA by a restriction enzyme/DNA polymerase system," *Proc. Nat'l Acad Sci. USA*, 89:392–396 1992.

Weitzel and Patel, "A single P1 clone bearing three genes from human chromosome 11p15.5: HRC1, HRAS1, and RNH," *GATA*, 11(5–6) 165–170, 1994.

Weitzel et al., "The *HRAS1* gene cluster: two upstream regions recognizing transcripts and a third encoding a gene with a leucine zipper domain," *Genomics*, 14:309–319, 1992.

Wu et al., "The ligation amplification reaction (LAR)–amplification of specific DNA sequences using sequential rounds of template–dependant ligation," *Genomics*, 4(4):560–569, 1989.

Yamaguchi et al., "Human chorionic gonadotropin a colorectal cancer and its relationship," *Br. J. Cancer*, 60:382–384, 1989.

Yoshimura et al., "Assessment of urinary β–core fragment of human chorionic gonadotropin as a new tumor marker of lung cancer," *Cancer*, 73:2745–2752, 1994.

Zhu et al., "Cloning and characterization of a new silver–stainable protein ssp29, a member of the Irr family," *Biochem. Mol. Biol. Int.*, 42:927–935, 1997.

* cited by examiner

```
HOJI   1  MELKVWVDGVQRIVCGVTEMTTCQEVVIALAQAIGRTGRYTIEKWRDTERHLAPHENPI      60
HRCQ   1 MLLGLAAMELKVWVDGIQRMVCGVSEQTTCQEVVIALAQAIGQTGRIFMLVQRLREKERQLLPQECPV  67

HOJI  61 ISLNKWGQASDVQLIRRTGPSLSERPTSDSVARIPERTLMRQSLPLS                             109
HRCI  68 GAQATCGQFASDVQFVLRRTGPSLAGRPSSDSCPP-PERQLIRASLPVKPRAA---          373(I)/337(II)
```

FIG.7

```
CAGTTGGTAACTGACTGACTACACAGACTTAGTCTTCTCCACTCCGTGTTCCTGCGGCTA                    60

GAGACATGACCTAACACCCTGATGACCACTCTCAGGGACCTTGAGTGACTGGCCGGTGCA                   120

CCATGGAACTTAAAGTATGGGTGGATGGAGTTCAGAGGATTGTTTGTGGAGTCACTGAAG                   180
  M  E  L  K  V  W  V  D  G  V  Q  R  I  V  C  G  V  T  E                      19

TCACAACTTGCCAGGAGGTTGTCATAGCCTTAGCTCAAGCAATAGGTCGAACTGGAAGGT                   240
 V  T  T  C  Q  E  V  V  I  A  L  A  Q  A  I  G  R  T  G  R                    39

ACACCCTTATAGAGAAATGGAGAGATACTGAAAGACACTTAGCACCTCATGAAAATCCTA                   300
 Y  T  L  I  E  K  W  R  D  T  E  R  H  L  A  P  H  E  N  P                    59

TCATATCCTTAAACAAATGGGGCAGTATGCTAGTGATGTGCAGTCATTCTACGACGAA                     360
 I  I  S  L  N  K  W  G  Q  Y  A  S  D  V  Q  L  I  L  R  R                    79

CTGGGCCGTCTCTCAGTGAGCGAGGACCACTTCAGACAGTGGCTGAATTCCTGAAAGAA                    420
 T  G  P  S  L  S  E  R  P  T  S  D  D  S  V  A  R  I  P  E  R                 99

CTTTATACAGGCAGAGTCTCCCCTTAGCTAAACTGAGGCCTCAGATTGACAAATCAATC                    480
 I  L  Y  R  Q  S  L  P  L  S  *                                              109
```

FIG.8-1

```
AAAAGGAGGAACCGAAAAGGAAATCACTGACATTTACAGGAGGTGCCAAAGGATTAATG    540
GACATTTTTGGAAAAAGGTAAAGAGAAACTGAGTTTAAGCAAAAGGTGCTGAATAACTGCAAA  600
ACAACAGCAGATGAGTTGAAGAAGCTAATCCGTCTCTGCAGACAGAGAAGCTTCAATCCATT   660
GAGAAACAGCTGGAATCTAATGAAATAGAAATAAGATTTTGGGAGCAAAAGTATAATTCC    720
AACCTTGAAGAGGAAATTGTCCGTCTCTAGAGCAAAAATGAATTACAGAGATTGAAAAACAGCTG 780
GAGGAGGAAGAATTCTGGGAAAAATGAATTACAGATTGAACAGGAAAATGAAAAACAGCTG  840
AAGGATCAACTTCAGAAATAGACAAGACAAAAAAAAAAAAAAAAA    888
```

FIG.8-2

SEQUENCE LISTING

<160> NUMBER OF SEQ ID NOS: 24

<210> SEQ ID NO 1
<211> LENGTH: 888
<212> TYPE: DNA
<213> ORGANISM: Homo sapiens

<400> SEQUENCE: 1

| cagttggtaa | ctgactgact | acacagactt | agtcttctcc | actccgtgtt | cctgcggcta | 60 |
| gagacatgac | ctaacaccct | gatgaccact | ctcagggacc | ttgagtgact | ggccggtgca | 120 |
| ccatggaact | taaagtatgg | gtggatggag | ttcagaggat | tgtttgtgga | gtcactgaag | 180 |
| tcacaacttg | ccaggaggtt | gtcatagcct | tagctcaagc | aataggtcga | actggaaggt | 240 |
| acacccttat | agagaaatgg | agagatactg | aaagacactt | agcacctcat | gaaaatccta | 300 |
| tcatatcctt | aaacaaatgg | gggcagtatg | ctagtgatgt | gcagctcatt | ctacgacgaa | 360 |
| ctgggccgtc | tctcagtgag | cgacccactt | cagacagtgt | ggctcgaatt | cctgaaagaa | 420 |
| ctttatacag | gcagagtctc | cccttagct | aaactgaggc | ctcagattga | caaatcaatc | 480 |
| aaaaggaggg | aaccgaaaag | gaaatcactg | acatttacag | gaggtgccaa | aggattaatg | 540 |
| gacatttttg | gaaaaggtaa | agaaactgag | tttaagcaaa | aggtgctgaa | taactgcaaa | 600 |
| acaacagcag | atgagttgaa | gaagctaatc | cgtctgcaga | cagagaagct | tcaatccatt | 660 |
| gagaaacagc | tggaatctaa | tgaaatagaa | ataagatttt | gggagcaaaa | gtataattcc | 720 |
| aaccttgaag | aggaaattgt | ccgtctagag | caaaagatca | aagaaacga | tgtagaaatt | 780 |
| gaggaggaag | aattctggga | aaatgaatta | cagattgaac | aggaaaatga | aaaacagctg | 840 |
| aaggatcaac | ttcagaaata | gacaagacaa | aaaaaaaaaa | aaaaaaaa | | 888 |

<210> SEQ ID NO 2
<211> LENGTH: 109
<212> TYPE: PRT
<213> ORGANISM: Homo sapiens

<400> SEQUENCE: 2

Met Glu Leu Lys Val Trp Val Asp Gly Val Gln Arg Ile Val Cys Gly
 1               5                  10                  15

Val Thr Glu Val Thr Thr Cys Gln Glu Val Val Ile Ala Leu Ala Gln
             20                  25                  30

Ala Ile Gly Arg Thr Gly Arg Tyr Thr Leu Ile Glu Lys Trp Arg Asp
         35                  40                  45

Thr Glu Arg His Leu Ala Pro His Glu Asn Pro Ile Ile Ser Leu Asn
     50                  55                  60

Lys Trp Gly Gln Tyr Ala Ser Asp Val Gln Leu Ile Leu Arg Arg Thr
 65                  70                  75                  80

Gly Pro Ser Leu Ser Glu Arg Pro Thr Ser Asp Ser Val Ala Arg Ile
                 85                  90                  95

Pro Glu Arg Thr Leu Tyr Arg Gln Ser Leu Pro Leu Ser
            100                 105

<210> SEQ ID NO 3
<211> LENGTH: 105
<212> TYPE: PRT
<213> ORGANISM: Homo sapiens -continued

```
<400> SEQUENCE: 3

Met Glu Leu Lys Val Trp Val Asp Gly Val Gln Arg Ile Val Cys Gly
 1               5                  10                  15

Val Thr Glu Val Thr Thr Cys Gln Glu Val Val Ile Ala Leu Ala Gln
            20                  25                  30

Ala Ile Gly Arg Thr Gly Arg Tyr Thr Leu Ile Glu Lys Trp Arg Asp
        35                  40                  45

Thr Glu Arg His Leu Ala Pro His Glu Asn Pro Ile Ile Ser Leu Asn
    50                  55                  60

Lys Trp Gly Gln Tyr Ala Ser Asp Val Gln Leu Ile Leu Arg Arg Thr
65                  70                  75                  80

Gly Pro Ser Leu Ser Glu Arg Pro Thr Ser Asp Ser Pro Glu Arg Thr
                85                  90                  95

Leu Tyr Arg Gln Ser Leu Pro Leu Ser
            100                 105

<210> SEQ ID NO 4
<211> LENGTH: 105
<212> TYPE: PRT
<213> ORGANISM: Homo sapiens

<400> SEQUENCE: 4

Met Glu Leu Lys Val Trp Val Asp Gly Ile Gln Arg Val Val Cys Gly
 1               5                  10                  15

Val Ser Glu Gln Thr Thr Cys Gln Glu Val Val Ile Ala Leu Ala Gln
            20                  25                  30

Ala Ile Gly Gln Thr Gly Arg Phe Val Leu Val Gln Arg Leu Arg Glu
        35                  40                  45

Lys Glu Arg Gln Leu Leu Pro Gln Glu Cys Pro Val Gly Ala Gln Ala
    50                  55                  60

Thr Cys Gly Gln Phe Ala Ser Asp Val Gln Phe Val Leu Arg Arg Thr
65                  70                  75                  80

Gly Pro Ser Leu Ala Gly Arg Pro Ser Ser Asp Ser Pro Glu Arg Cys
                85                  90                  95

Leu Ile Arg Ala Ser Leu Pro Val Lys
            100                 105

<210> SEQ ID NO 5
<211> LENGTH: 23
<212> TYPE: DNA
<213> ORGANISM: Homo sapiens

<400> SEQUENCE: 5
gggaattctc tcttgagcag agg                                          23

<210> SEQ ID NO 6
<211> LENGTH: 22
<212> TYPE: DNA
<213> ORGANISM: Homo sapiens

<400> SEQUENCE: 6
gggtcgacca aagctgcttc ac                                           22

<210> SEQ ID NO 7
<211> LENGTH: 29
<212> TYPE: DNA
<213> ORGANISM: Homo sapiens
```

-continued

```
<400> SEQUENCE: 7
tgaggtgcct aagtgtcttt cagtatctc                                    29

<210> SEQ ID NO 8
<211> LENGTH: 25
<212> TYPE: DNA
<213> ORGANISM: Homo sapiens

<400> SEQUENCE: 8
gctaaggcta tgacaacctc ctggc                                        25

<210> SEQ ID NO 9
<211> LENGTH: 25
<212> TYPE: DNA
<213> ORGANISM: Homo sapiens

<400> SEQUENCE: 9
cagtgactcc acaacaatcc tctga                                        25

<210> SEQ ID NO 10
<211> LENGTH: 24
<212> TYPE: DNA
<213> ORGANISM: Homo sapiens

<400> SEQUENCE: 10
ttggtaactg actgactaca caga                                         24

<210> SEQ ID NO 11
<211> LENGTH: 19
<212> TYPE: DNA
<213> ORGANISM: Homo sapiens

<400> SEQUENCE: 11
tactgccccc atttgttta                                               19

<210> SEQ ID NO 12
<211> LENGTH: 23
<212> TYPE: DNA
<213> ORGANISM: Homo sapiens

<400> SEQUENCE: 12
cttagtcttc tccactccgt gtt                                          23

<210> SEQ ID NO 13
<211> LENGTH: 24
<212> TYPE: DNA
<213> ORGANISM: Homo sapiens

<400> SEQUENCE: 13
gattagcttc ttcaactcat ctgc                                         24

<210> SEQ ID NO 14
<211> LENGTH: 25
<212> TYPE: DNA
<213> ORGANISM: Homo sapiens

<400> SEQUENCE: 14
tgacctaaca ccctgatgac cactc                                        25

<210> SEQ ID NO 15
<211> LENGTH: 29
<212> TYPE: DNA
<213> ORGANISM: Homo sapiens
```

<400> SEQUENCE: 15
tgaggtgcta agtgtctttc agtatctct                29

<210> SEQ ID NO 16
<211> LENGTH: 25
<212> TYPE: DNA
<213> ORGANISM: Homo sapiens

<400> SEQUENCE: 16
tggaacttaa agtatgggtg gatgg                    25

<210> SEQ ID NO 17
<211> LENGTH: 24
<212> TYPE: DNA
<213> ORGANISM: Homo sapiens

<400> SEQUENCE: 17
ctaaggggga gactctgcct gtat                     24

<210> SEQ ID NO 18
<211> LENGTH: 24
<212> TYPE: DNA
<213> ORGANISM: Homo sapiens

<400> SEQUENCE: 18
actgaaagac acttagcacc tcat                     24

<210> SEQ ID NO 19
<211> LENGTH: 22
<212> TYPE: DNA
<213> ORGANISM: Homo sapiens

<400> SEQUENCE: 19
tttagctaag ggggagactc tg                       22

<210> SEQ ID NO 20
<211> LENGTH: 20
<212> TYPE: DNA
<213> ORGANISM: Homo sapiens

<400> SEQUENCE: 20
gctcgaattc ctgaaagaac                          20

<210> SEQ ID NO 21
<211> LENGTH: 22
<212> TYPE: DNA
<213> ORGANISM: Homo sapiens

<400> SEQUENCE: 21
ctctagacgg acaatttcct ct                       22

<210> SEQ ID NO 22
<211> LENGTH: 30
<212> TYPE: DNA
<213> ORGANISM: Homo sapiens

<400> SEQUENCE: 22
cagggacctt gagtgactgg ccggtgcacc               30

<210> SEQ ID NO 23
<211> LENGTH: 30
<212> TYPE: DNA
<213> ORGANISM: Homo sapiens -continued

```
<400> SEQUENCE: 23
caaggagctc aatggaactt aaagtatggg                                        30

<210> SEQ ID NO 24
<211> LENGTH: 30
<212> TYPE: DNA
<213> ORGANISM: Homo sapiens

<400> SEQUENCE: 24
cttgctcgag gctaaggggg agactctgcc                                        30
```

HUMAN TUMOR-ASSOCIATED GENE

The present application claims the priority of U.S. Provisional Patent Application Serial No. 60/072126, filed Jan. 22, 1998, the entire disclosure of which is incorporated herein by reference without disclaimer.

The U.S. Government has certain rights in the present invention pursuant to Grants FANY, P01CA1038 from the National Cancer Institute, National Institutes of Health.

BACKGROUND OF THE INVENTION

1. Field of the Invention

The present invention relates generally to the field of cancer diagnostics. More particularly, it concerns markers for use in the diagnosis and prognosis of cancer. Also provided are related protein, DNA and antibody compositions and various methods of use thereof, including methods for cancer diagnosis and treatment.

2. Description of Related Art

Cancer is one of the leading causes of disease, being responsible for 526,000 deaths in the United States each year (Boring et al., 1993). For example, breast cancer is the most common form of malignant disease among women in Western countries and, in the United States, is the most common cause of death among women between 40 and 55 years of age (Forrest, 1990). The incidence of breast cancer is increasing, especially in older women, but the cause of this increase is unknown. Malignant melanoma is another form of cancer whose incidence is increasing at a frightening rate, at least sixfold in the United States since 1945, and is the single most deadly of all skin diseases (Fitzpatrick, 1986).

One of the most devastating aspects of cancer is the propensity of cells from malignant neoplasms to disseminate from their primary site to distant organs and develop into metastases. Despite advances in surgical treatment of primary neoplasms and aggressive therapies, most cancer patients die as a result of metastatic disease. Animal tests indicate that about 0.01% of circulating cancer cells from solid tumors establish successful metastatic colonies (Fidler, 1993).

Thus, the detection of occult cancer cells in circulation is important in assessing the level of tumor progression and metastasis. Because subclinical metastasis can remain dormant for many years, monitoring of patients' blood for circulating tumor cells may prove advantageous in detecting tumor progression before metastasis to other organs occurs. Assessment of circulating tumor cells also would provide a rapid monitoring system to determine if a specific therapy is effective.

The recognition or lack of recognition of cancer cells by a host organism is a complicated process. Understanding of the field presumes some understanding of both basic immunology and oncology. Early research on mouse tumors revealed that these cells displayed molecules which led to rejection of tumor cells when transplanted into syngeneic animals. These molecules are "recognized" by T-cells in the recipient animal, and provoke a cytolytic T-cell response with lysis of the transplanted cells. This evidence was obtained with tumors induced in vitro by chemical carcinogens (Prehn, et al., 1957; Klein et al., 1960; Gross, 1943, Basombrio, 1970), as well as on tumors induced in vitro via ultraviolet radiation. (Kripke, 1974). The antigens expressed by the tumors and which elicited the T-cell response were found to be different for each tumor. This class of antigens has come to be known as "tumor specific transplantation antigens" (TSTAs).

While T-cell mediated immune responses were observed for tumors induced through the application of carcinogens, spontaneous tumors were thought to be generally non-immunogenic. These were, therefore, believed not to present antigens which provoked a response to the tumor in the tumor carrying subject (Hewitt, et al., 1976).

Later research found that when spontaneous tumors were subjected to mutagenesis, immunogenic variants were produced which did generate a response. Indeed, these variants were able to elicit an immune protective response against the original tumor (Van Pel et al., 1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors (Fearon et al., 1988) in this regard.

A class of antigens has been recognized which are presented on the surface of tumor cells and are recognized by cytolytic T cells, leading to lysis. This class of antigens will be referred to as "tumor rejection antigens" (TRAs). TRAs may or may not elicit antibody responses. These antigens have been studied by cytolytic T cell characterization studies, i.e., the in vitro study of the identification of the antigen by a particular cytolytic T cell (CTL) subset. The subset proliferates upon recognition of the presented tumor rejection antigen, and the cells presenting the antigen are lysed. Characterization studies have identified CTL clones which specifically lyse cells expressing the antigens. (Levy et al., 1977; Boon et al., 1980; Brunner et al., 1980; Maryanski et al., 1980; Maryanski et al., 1982; Palladino et al., 1987).

U.S. Pat. No. 5,342,774, incorporated herein by reference, described a family of human tumor rejection antigen precursor coding genes, referred to as the MAGE family (van der Bruggen et al., 1991; Traversari et al., 1992). It now is clear that the various genes of the MAGE family are expressed in tumor cells, and can serve as markers for the diagnosis of such tumors, as well as for other purposes discussed therein.

Although MAGE expression has been identified in different types of cell lines and tumor tissues, it is not ubiquitously expressed in tumors of all types. Similar molecules, such as PAGE, BAGE (Boel et al., 1995) and GAGE (van den Eynde, 1995) have been identified as tumor recognition antigens for a variety of cancers including melanoma, sarcomas, non-small cell lung cancers, head and neck tumors, bladder tumors and prostate tumors. However, there remains a significant scientific hurdle in identifying which MAGE gene will be expressed by a particular tumor type. Thus, while on one level one can say that MAGE, BAGE and PAGE genes are "markers" for tumors, on the level of specific tumor types, the correlation of marker and tumor type is not predictable, and must be determined empirically. Thus, there is a need to define tumor marker antigens that are expressed ubiquitously on all cancer types.

SUMMARY OF THE INVENTION

The present invention seeks to overcome these and other drawbacks inherent in the prior art by providing nucleic acid species and marker genes that are expressed in cancers cells, and methods of making and using such nucleic acids and related proteins and antibodies. Further provided are methods for the diagnosis, prognosis and treatment of cancers using one or more of the foregoing compositions.

Thus, in order to meet the objectives of the present invention, there is provided herein a DNA segment comprising an isolated gene that encodes a HOJ-1 polypeptide. In particular embodiments, there is provided a gene that encodes a human HOJ-1 polypeptide. In other preferred embodiments, there is provided a gene that encodes a HOJ-1 protein or peptide that includes a contiguous amino acid sequence from SEQ ID NO:2. In still other embodiments, the gene includes a contiguous nucleic acid sequence from SEQ ID NO:1. In certain embodiments, the present invention provides a nucleic acid segment that encodes a HOJ-1 peptide of from about 105 to 109 amino acids in length.

The DNA segment may comprise a gene that encodes the HOJ-1 protein of SEQ ID NO:2. In other embodiments, the present invention comprises a gene that has the nucleic acid sequence of SEQ ID NO:1. In particular aspects, the gene is positioned under the control of a promoter. In preferred aspects, the gene is positioned under the control of a recombinant promoter in an expression vector. In other specific embodiments, the gene is positioned in reverse orientation under the control of a promoter, the promoter expressing an antisense product. In particular embodiments, the DNA segment may be further defined as a recombinant vector.

Other aspects of the present invention provide a recombinant host cell comprising a DNA segment that comprises an isolated gene that encodes a HOJ-1 protein. In preferred embodiments the recombinant host cell of the present invention further may be defined as a prokaryotic host cell. In other embodiments, the recombinant host cell of the present invention further may be defined as a eukaryotic host cell. In particular aspects, the DNA segment is introduced into the cell by means of a recombinant vector. In preferred embodiments, the host cell expresses the DNA segment to produce the encoded HOJ-1 protein or peptide. In more preferred embodiments, the expressed HOJ-1 protein or peptide includes a contiguous amino acid sequence from SEQ ID NO:2.

The present invention also contemplates a method of using a DNA segment that encodes a HOJ-1 protein or peptide, comprising expressing the DNA segment in a recombinant host cell and collecting the HOJ-1 protein or peptide expressed by the cell.

In further aspects, the present invention provides an isolated nucleic acid segment comprising a sequence region that consists of at least 14 contiguous nucleotides that have the same sequence as, or are complementary to, 14 contiguous nucleotides of SEQ ID NO:1.

In still further aspects, the present invention contemplates an isolated nucleic acid segment of from 14 to about 888 nucleotides in length that hybridizes to the nucleic acid segment of SEQ ID NO:1, or a complement thereof, under standard hybridization conditions. In other embodiments, there is provided an isolated nucleic acid segment of from 14 to about 888 nucleotides in length that hybridizes under high stringency conditions to the nucleic acid segment of SEQ ID NO:1, or a complement thereof. The nucleic acid segment further may be defined as a DNA segment. In preferred embodiments, the nucleic acid segment further may be defined as a RNA segment.

Also provided by the present invention is an isolated nucleic acid segment comprising a contiguous nucleic acid sequence that is identical or complementary to the nucleic acid sequence of SEQ ID NO:1. Another aspects of the present invention provides an isolated nucleic acid segment having the contiguous nucleic acid sequence of SEQ ID NO:1, or a complement thereof. In preferred embodiments, the nucleic acid may be selected from the group consisting of genomic DNA, complementary DNA and RNA. In particular embodiments, the nucleic acid is a complementary DNA and further comprises a promoter operably linked to the region, or the complement thereof, encoding a HOJ-1 tumor antigen. In other preferred embodiments, the nucleic acid further comprises a polyadenylation signal operably linked to the region encoding the tumor antigen. In still further embodiments, the nucleic acid further comprises an origin of replication. In defined embodiments, the nucleic acid may be a viral vector selected from the group consisting of retrovirus, adenovirus, herpesvirus, vaccinia virus, poxvirus and adeno-associated virus or a bacterial vector or a plasmid vector. In other embodiments, the nucleic acid is packaged in a virus particle. In alternative preferred embodiments, the nucleic acid is packaged in a liposome.

The present invention provides a nucleic acid detection kit comprising, in suitable container means, an isolated nucleic acid segment comprising a contiguous nucleic acid sequence from SEQ ID NO:1, or a complement thereof. In preferred aspects, the kit further may comprise a detection reagent. In preferred embodiments, the detection reagent is a detectable label that is linked to the nucleic acid segment.

Other embodiments, contemplate a nucleic acid detection kit comprising, in suitable container means, an isolated nucleic acid segment that hybridizes under high stringency conditions to the nucleic acid sequence of SEQ ID NO:1, or a complement thereof. In particular aspects, the kit may comprise an isolated nucleic acid segment comprising a contiguous nucleic acid sequence from SEQ ID NO:1, or a complement thereof.

Particular aspects of the present invention contemplate a nucleic acid detection kit comprising, in suitable container means, a pair of primers for amplifying a nucleic acid having a sequence from SEQ ID NO:1, or a complement thereof. Other aspects provide a nucleic acid detection kit comprising, in suitable container means, a pair of primers with sequences from spatially distant regions of SEQ ID NO:1. In particular embodiments, the kit may comprise a pair of primers, each primer having a sequence from a spatially distant region of SEQ ID NO:1, or a complement thereof.

Also contemplated by the present invention is a composition comprising a purified HOJ-1 protein or peptide that includes a contiguous amino acid sequence from SEQ ID NO:2. Another aspect of the present invention provides a purified HOJ-1 protein having the amino acid sequence of SEQ ID NO:2. Yet another preferred embodiments provides a recombinant HOJ-1 protein or peptide prepared by expressing a DNA segment that encodes a HOJ-1 protein or peptide in a recombinant host cell and purifying the expressed HOJ-1 protein or peptide away from total recombinant host cell components.

The present invention further provides an isolated protein or polypeptide comprising a contiguous amino acid sequence encoded by a contiguous nucleic acid sequence from SEQ ID NO:1. Preferred embodiments provide an isolated protein or polypeptide having an amino acid sequence encoded by the nucleic acid sequence of SEQ ID NO:1. In particular embodiments, the protein or polypeptide may comprise a contiguous amino acid sequence having the sequence of SEQ ID NO:2.

Other embodiments provide an isolated peptide, of between about 10 and about 50 amino acids in length, comprising a contiguous amino acid sequence encoded by a contiguous nucleic acid sequence from SEQ ID NO:1. In more particular embodiments the peptide is a HOJ-1 peptide that comprises the contiguous amino acid sequence of SEQ ID NO:2.

The present invention also contemplates an antibody that binds to a HOJ-1 protein or peptide that includes a contiguous amino acid sequence from SEQ ID NO:2. Other embodiments contemplate an antibody that binds to a protein or peptide encoded by a contiguous sequence from the nucleic acid sequence of SEQ ID NO:1. In preferred embodiments, the antibody binds to a HOJ-1 protein or peptide. In particular embodiments, the antibody is a monoclonal antibody. In other embodiments, the antibody is operatively attached to a detectable label. In particular aspects, the label may be selected from the group consisting of a fluorescent label, a chemiluminescent label, a radiolabel and an enzyme. In other embodiments, the antibody is operatively attached to a cytotoxic, anticellular or chemotherapeutic agent.

The present invention further provides a hybridoma cell that produces a monoclonal antibody that binds immunologically to a tumor antigen designated as HOJ-1. In preferred embodiments, the antibody does not bind immunologically to other human polypeptides. Other embodiments provide a polyclonal antisera, antibodies of which bind immunologically to a tumor antigen designated as HOJ-1.

Also provided by the present invention is an immunodetection kit comprising, in suitable container means, a first antibody that binds to a HOJ-1 protein or peptide that includes a contiguous amino acid sequence from SEQ ID NO:2. Other embodiments provide an immunodetection kit comprising, in suitable container means, a first antibody that binds to a protein or peptide encoded by a contiguous sequence from the nucleic acid sequence of SEQ ID NO:1 and an immunodetection reagent. In particular aspects, the kit comprises an antibody that binds to a HOJ-1 protein or peptide having the sequence as set forth in SEQ ID NO:2. In other aspects, the immunodetection reagent is a detectable label that is operatively attached to the first antibody. In still, further aspects, the immunodetection reagent is a detectable label that is operatively attached to a second antibody that has binding affinity for the first antibody. Other embodiments contemplate the kit of the present invention further comprising a second antibody that has binding affinity for the first antibody, and wherein the immunodetection reagent is a detectable label that is operatively attached to a third antibody that has binding affinity for the second antibody. In preferred embodiments, the first antibody is bound to a solid support. In other embodiments, the kit further comprises a suitably aliquoted composition of the protein or peptide to which the first antibody binds.

The present invention also provides a method for detecting a cancer cell, comprising identifying a cell that contains a HOJ-1 protein, peptide or mRNA. In preferred embodiments, the cancer cell is a metastatic cancer cell or a primary cancer cell. In further preferred embodiments, the cancer cell is a melanoma, glioblastomas, astrocytomas, leukemia, lymphoma, breast, gastric, colon, pancreas, renal, testicular, ovarian, lung, prostate, hepatic, germ cell or a lung cancer cell.

Other embodiments of the present invention provide a method for detecting a cancer cell, comprising identifying a cell that contains a protein or peptide encoded by a contiguous sequence from the nucleic acid sequence of SEQ ID NO:1. In preferred aspects the cancer cell is a metastatic cancer cell or a primary cancer cell. In other preferred aspects the cancer cell is a melanoma, glioblastomas, astrocytomas, leukemia, lymphoma, breast, gastric, colon, pancreas, renal, testicular, ovarian, lung, prostate, hepatic, germ cell or a lung cancer cell. In particularly preferred embodiments, the cell is identified by means of a molecular biological assay to identify a nucleic acid that encodes the protein or peptide. In certain aspects of the present invention the method comprises contacting sample nucleic acids from the cell with an isolated nucleic acid segment comprising a contiguous sequence SEQ ID NO:1, under conditions effective to allow hybridization of substantially complementary nucleic acids, and detecting the hybridized complementary nucleic acids thus formed. In preferred embodiments, the sample nucleic acids contacted are located within a cell. In other embodiments, the sample nucleic acids are separated from a cell prior to contact. In yet other embodiments, the sample nucleic acids are RNA. It is contemplated that the isolated nucleic acid segment comprises a detectable label and the hybridized complementary nucleic acids are detected by detecting the label. In further embodiments, the method may further comprise amplifying nucleic acids from the cell by conducting a polymerase chain reaction using a pair of primers, each primer having a sequence from a spatially distant region of SEQ ID NO:1, and detecting the amplified nucleic acids thus formed. Nucleic acids may also be amplified by nucleic acid amplification techniques other than the polymerase chain reaction.

In particularly defined embodiments, the method of detecting a cancer comprises the steps of contacting sample nucleic acids from the cell with a pair of nucleic acid primers that hybridize to distant sequences from SEQ ID NO:1, wherein the primers are capable of amplifying a corresponding nucleic acid segment when used in conjunction with a polymerase chain reaction; conducting a polymerase chain reaction to create amplification products or using other methods of nucleic acid amplification and detecting the amplification products "thus formed. In particular embodiments, the amplification products thus formed are detected by contacting the amplification products with an isolated nucleic acid segment comprising a contiguous sequence from SEQ ID NO:1, under stringent hybridization conditions, and detecting amplification products that hybridize to the nucleic acid segment. In further embodiments, the amplification products may be formed using primers labeled with agents such as biotin, but not restricted to biotin, and the amplification products thus formed are detected directly by agents that recognize the primer label, often a fluorescently labelled agent that binds or recognizes the primer label.

In certain embodiments, it is contemplated that the cell is present within a biological sample obtained from a patient suspected of having cancer. In particular embodiments, the cell is identified by means of an immunoassay to identify the protein or peptide. In particularly preferred embodiments the cell is identified by contacting the cell or a sample therefrom with a first antibody that binds to a protein or peptide encoded by a contiguous sequence from the nucleic acid sequence of SEQ ID NO:1, under conditions effective to allow the formation of immune complexes, and detecting the immune complexes so formed. In further defined aspects, the first antibody is linked to a detectable label and the immune complexes are detected by detecting the presence of the label. In alternative preferred aspects the immune complexes are detected by means of a second antibody linked to a detectable label, the second antibody having binding affinity for the first antibody.

Also contemplated herein is a method of diagnosing a cancer comprising the steps of obtaining a sample from a subject; and determining the expression a HOJ-1 in cells of the sample. In particular aspects, the cancer may be selected from the group consisting of melanoma, leukemia, lymphoma, glioblastomas, astrocytomas, breast, gastric, colon, pancreas, renal, testicular, ovarian, lung, prostate, hepatic, lung cancer and germ cell tumors. In other aspects, the sample is a tissue or fluid sample. In preferred embodiments, the determining comprises assaying for a nucleic acid from the sample. In other aspects the method further comprises subjecting the sample to conditions suitable to amplify the nucleic acid. Preferred embodiments contemplate that the determining comprises contacting the sample with an antibody that binds immunologically to a HOJ-1 protein or peptide. In still further embodiments, the determining may further comprise subjecting proteins of the sample to ELISA. In particular aspects of the present invention, the diagnostic method further comprises the step of comparing the expression of HOJ-1 with the expression of HOJ-1 in non-cancer samples. In more particular aspects, the comparison involves evaluating the level of HOJ-1 expression. In further aspects, the comparison involves evaluating the structure of the HOJ-1 gene, protein or transcript.

The present invention provides a method for altering the phenotype of a tumor cell comprising the step of contacting the cell with a agent that inhibits HOJ-1 under conditions permitting the uptake of the agent by the tumor cell. In particular embodiments, the agent is encapsulated in a liposome. In other defined embodiments, the tumor cell is derived from a tissue selected from the group consisting of skin, brain, CNS, breast, gastric, colon, pancreas, renal, ovarian, lung, prostate, hepatic, lung tissue and germ cell tissue. In preferred aspects, the tissue may comprise melanoma, leukemia, lymphoma, glioblastomas, astrocytomas, breast, gastric, colon, pancreas, renal, testicular, ovarian, lung, prostate, hepatic, lung cancer and germ cell tumor cells. In particular aspects, the phenotype is selected from the group consisting of proliferation, migration, contact inhibition, soft agar growth and cell cycling.

A method for altering the phenotype of a tumor cell also is provided. The method comprises the step of contacting the cell with a nucleic acid (i) encoding antisense HOJ-1 and (ii) a promoter active in the tumor cell, wherein the promoter is operably linked to the region encoding the antisense HOJ-1, under conditions permitting the uptake of the nucleic acid by the tumor cell. In particular aspects of this embodiment, the tumor cell is derived from a tissue selected from the group consisting of skin, brain, CNS, breast, gastric, colon, pancreas, renal, ovarian, lung, prostate, hepatic, and lung tissue. In other aspects, the phenotype is selected from the group consisting of proliferation, migration, contact inhibition, soft agar growth or cell cycling. In preferred embodiments, the nucleic acid is encapsulated in a liposome or in a viral particle. In other embodiments, the nucleic acid is a viral vector selected from the group consisting of retrovirus, adenovirus, adeno-associated virus, vaccinia virus, pox-virus and herpesvirus or bacterial vectors or plasmid vectors.

Also provided is a method for treating cancer, comprising inhibiting HOJ-1 within a patient with cancer. In particular aspects of this embodiments, the inhibiting comprises the step of contacting a tumor cell within a subject with a nucleic acid (i) encoding antisense HOJ-1 and (ii) a promoter active in the tumor cell, wherein the promoter is operably linked to the region encoding the antisense HOJ-1, under conditions permitting the uptake of the nucleic acid by the tumor cell. In other aspects, the inhibiting comprises administering to a patient with the cancer a biologically effective amount of composition comprising a HOJ-1 inhibitor. In preferred embodiments, the inhibitor comprises an antibody that binds to and inhibits the protein or peptide. In other preferred embodiments, the inhibitor comprises an immunotoxin that binds to and inhibits the protein or peptide. In still further embodiments, the inhibitor composition comprises a recombinant vector that expresses an agent that inhibits the production or activity of the protein or peptide. In preferred embodiments, the subject is a human.

Also provided is a method of predicting tumor metastasis comprising the steps of obtaining a sample from a subject; and determining the expression a HOJ-1 tumor antigen in cells of the sample. In particular aspects, the cancer is distinguished as metastatic and non-metastatic. In other aspects, the determining comprises assaying for a HOJ-1 nucleic acid or polypeptide in the sample.

The present invention also provides a method of screening a candidate substance for anti-tumor activity comprising the steps of providing a cell expressing HOJ-1 polypeptide; contacting the cell with the candidate substance; and determining the effect of the candidate substance on the cell. In preferred embodiments, the cell is a tumor cell. In other embodiments, the determining comprises comparing one or more characteristics of the cell in the presence of the candidate substance with characteristics of a cell in the absence of the candidate substance. In more particular embodiments, the characteristic is selected from the group consisting of HOJ-1 expression, MAGE-binding activity, proliferation, metastasis, contact inhibition, soft agar growth, cell cycle regulation, chromosome recombination, tumor formation, tumor progression and tissue invasion. In defined embodiments, the candidate substance is a chemotherapeutic or radiotherapeutic agent. In other embodiments, the candidate substance is selected from a small molecule library. The cell may be contacted in vitro, in alternate embodiments, the cell is contacted in vivo.

The present invention provides a method of generating an anti-cancer immune response in a patient, comprising providing to a patient with the cancer an immunologically effective amount of a protein or peptide encoded by a contiguous sequence from the nucleic acid sequence of SEQ ID NO:1. In preferred aspects, the patient is provided with an immunologically effective amount of a protein or peptide encoded by a contiguous sequence from the nucleic acid sequence of SEQ ID NO:1. In other aspects, the patient is provided with an immunologically effective amount of a nucleic acid composition that encodes the protein or peptide.

Also contemplated is a therapeutic kit comprising, in suitable container means, an effective amount of a pharmaceutically acceptable formulation of an inhibitor that inhibits the production or activity of a protein or peptide encoded by a contiguous sequence from the nucleic acid sequence of SEQ ID NO:1. In preferred embodiments, the pharmaceutical formulation is suitable for parenteral administration.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5B shows a schematic of the results of PCR™ analysis.

FIG. 7 shows a comparison of the predicted amino acid sequence of HOJ-1 (SEQ ID NO:3) with that of HRC1 (SEQ ID NO:4). Identical residues are enclosed in boxes.

FIG. 8 Alignment of nucleotide and predicted amino acid sequence (SEQ ID NO:1 AND SEQ ID NO:2). The coding region is shown from position 123 to 449. The termination codon (TAA) is indicated by an asterisk. The potential N-myristoylation (underline) and phosphorylation (dashed line) are indicated.

DESCRIPTION OF ILLUSTRATIVE EMBODIMENTS

1. The Present Invention

Figure 1:
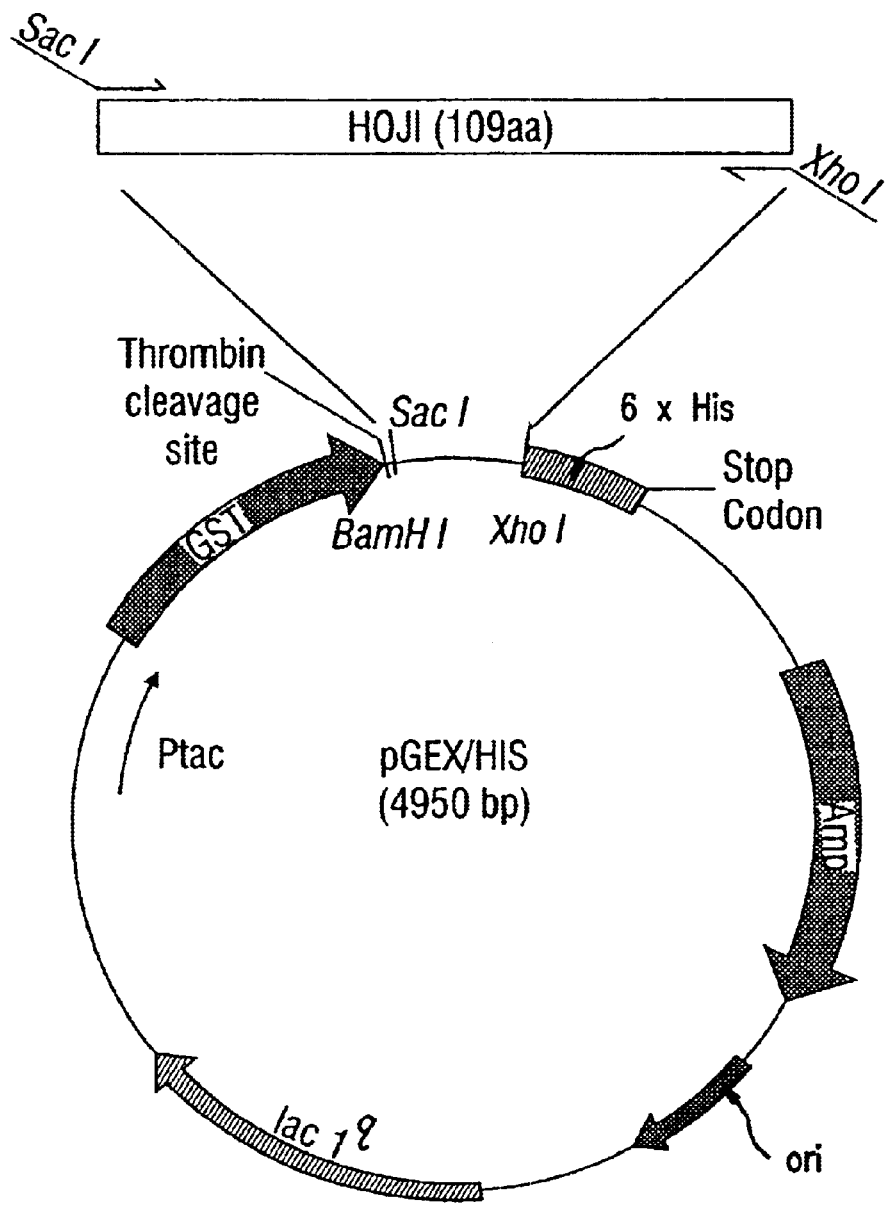
FIG. 1 shows HOJ-1 subcloned into a modified GST-fusion vector pGEX-1 λT (Pharmacia) (Smith and Johnson, 1988) that contains an in-frame hexa-histidine tag on the C-terminal end.

The present invention describes a novel cancer marker gene, designated HOJ-1. HOJ-1 was discovered by using the two hybrid yeast system in which the "bait" protein was human MAGE-1 (Van Der Bruggen et al., 1991). The full sequence open reading frame MAGE-1 protein was used as the "bait" to detect an interacting protein. A cDNA clone product was identified to interact with MAGE-1 protein.

A standard two hybrid yeast system was used to isolate a potential protein that interacts with MAGE-1. MAGE-1 is found in tumor tissues, and testis and placenta only. The interacting protein for MAGE-1 was identified using a yeast human testis cDNA library (Clontech). Screening the library was performed as instruction provided in the manual by Clontech. A clone termed C-28 (partial sequence for HOJ-1) was isolated and sequenced. Subsequently, this was referred to as HOJ-1.

Initially, a partial cDNA sequence was isolated. Using various molecular techniques, the full open reading frame sequence of HOJ-1 was determined and is presented herein as SEQ ID NO:1. The mRNA sequence is 888 base pairs in length and has been deposited in GenBank accession number U82396 (incorporated herein by reference). In databank search, it was determined that there is no known nucleic acid with a similar sequence. The closest related sequence belongs to the HRC1 and has only a 64% nucleic acid homology; however, it is not a continuous sequence (FIG. 7). HRC1 is a potential oncogene or transcription related factor (growth or differentiation regulator), whose function is currently unknown (Weitzel et al., 1992; Weitzel and Patel, 1994). HRC stands for H-ras cluster region, indicating that HRC is located near H-ras. Both H-ras1 and HRC1 are from regions on chromosome 11p15.5. HOJ-1 has a Ras-associated binding domain which spans codon 1 to 82 of HOJ-1.

The HOJ-1 cDNA sequence was cloned into a vector and expressed as a recombinant protein. A 6×HIS tag was inserted into the recombinant protein for affinity purification. The recombinant protein expressed from HOJ-1 sequence was approximately 15 kDa (predicted size) after affinity purification and run under reducing conditions in SDS-PAGE.

Antibodies to HOJ-1 also were generated. HOJ-1 protein was injected in New Zealand White rabbits and polyclonal antibody with specificity to the 15 kDa was determined by Western blotting. Antibody titers after 2 injections were >1:50,000 dilution. Normal rabbit sera (pre-bleed) did not bind to HOJ-1 in Western blot analysis.

In certain embodiments of the present invention, it is contemplated that the HOJ-1 mRNA sequence can be used as a marker to detect cancer. Primer sequences were designed from the full cDNA sequence of HOJ-1. The cDNA sequence (888 bp) contains at least 1 intron region. This was determined by partial genomic sequencing from the 5' end of the genomic clone isolated. Several primer sequences for RT-PCR™ were assessed. Normal and cancer tissues were assessed. RT-PCR™ studies indicated by gel electrophoresis that normal cells, except testis and placenta, do not express HOJ-1. Multiple carcinoma cell lines and biopsies were shown to express HOJ-1 at different frequencies. These include melanoma, glioblastomas, astrocytomas and carcinomas of the breast, gastric, colon, pancreas, renal, ovarian, lung, prostate, hepatic, and lung. Primary and metastatic human tumor biopsies also have been assessed and found to express HOJ-1. Also, leukemias of different origin were shown to express HOJ-1.

One of the unique features of this gene expression is that it is expressed in a wide variety of cancers of different origin and not normal cells. This observation is similar to that of the MAGE gene family. The HOJ-1 gene is not lineage specific or a differentiation gene marker. Furthermore, it does not have homology to members of the MAGE, BAGE, PAGE or GAGE gene families.

There are various types of tumor markers known in the art. These markers include oncogenes, tumor antigens and mutated tumor suppressors. It is likely that the HOJ-1 tumor marker of the present invention will fall into one of these categories. Indeed, it appears that HOJ-1 may be an oncogene regulating cell growth/differentiation. The closest known sequence (64% homology) is HRC1, a potential oncogene (Weitzel et al., 1992). It is suggested that the HOJ-1 protein may have important regulatory properties on MAGE-1 or MAGE-related proteins since it potentially interacts with MAGE-1. MAGE-1 is expressed in cancers and only in normal tissue such as testis and placenta. MAGE-1 related family members share similar amino acid homologies such as MAGE-2, 3, 4, 6 and 12.

The identification of HOJ-1 as a novel gene that is expressed in different types of cancer tissue, as provided by the present invention, may be exploited to provide compositions and methods for the diagnosis, monitoring and prognostic evaluation of patients with cancer, and further provide new treatment methods. Such compositions and methods are disclosed in further detail herein below.

2. Nucleic Acids

The present invention identifies of a new human cancer marker. The full open-reading time sequence has been determined and the HOJ-1 gene sequence is given in SEQ ID NO:1. The open reading frame sequence (genomic) contains at least one intron. RT-PCR™ primer sequences designed from open-reading frame cDNA were used for the detection of the HOJ-1 cancer marker. mRNA was detected under optimal conditions in human cancer cells and tissues but not in normal tissue. RT-PCR™ analysis revealed the expression of HOJ-1 gene in multiple cancer cell lines, as well as in multiple types of primary and metastatic human cancer biopsies, however, normal donor PBL do not express the gene under optimal conditions. Thus, the HOJ-1 gene is a good cancer marker for many metastatic human cancers in lymphoid related tissues such as blood, lymph, lymphnodes, bone marrow and so on.

The HOJ-1 cancer marker of the present invention is intended for use in the design of diagnostic and prognostic oligonucleotide probes, primers and oligonucleotides, and for use in protein and peptide expression. When used in combination with nucleic acid amplification procedures, these probes and primers permit the rapid analysis of biopsy core specimens. The probes and primers can be used for in situ hybridization and/or in situ PCR™ detection and diagnosis of cancer.

In addition, it should be clear that the present invention is not limited to the specific nucleic acids disclosed herein. As discussed below, a "HOJ-1 gene" may contain a variety of different bases and yet still produce a corresponding polypeptide that is functionally indistinguishable, and in some cases structurally, from the human gene disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the function of HOJ-1.

a. Nucleic Acids Encoding HOJ-1

The present invention provides a marker sequence connected with cancer. This marker comprises HOJ-1 gene products, such as those connected with SEQ ID NO:2. Indeed, the link between HOJ-1 and cancer or metastasis has only been established by the present invention in that this invention is the first study to identify HOJ-1 and to link HOJ-1 gene expression with a human cancer. It is likely that HOJ-1 is the first of a family of cancer related genes. The HOJ-1 gene has been designated as C12or f2 by the Human Gene Nomenclature Committee.

The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given HOJ-1 sequence may be represented by natural variants that have slightly different nucleic acid sequences but, nonetheless, encode the same protein (see Table 1 below). It is not necessary for the proteins or peptides encoded by the nucleic acid segments of the invention to be identified. In that the nucleic acid sequences themselves have been identified by virtue of their differential expression in cancers, they are evidently useful for their intended diagnostic and prognostic functions. However, if so desired, the longer and fill length cancer marker gene sequence of the invention also may be defined in terms of the proteins and polypeptides encoded by such a sequence.

Accordingly, in certain exemplary aspects, the present invention concerns nucleic acid sequences that. encode proteins, polypeptides or peptides that are expressed in cancer, and may be differentially expressed in different metastatic forms of cancer. An example of a particular cancer marker gene sequence of the invention is the HOJ-1 marker gene sequence.

The HOJ-1 and other DNA segments of the invention, whether full length or partial gene sequences, are preferably isolated away from, or purified free from, total genomic DNA of cells or tissues. Included within the terms "nucleic acid and DNA segments", are DNA and RNA segments and smaller fragments of such segments, and also recombinant vectors, including, for example, plasmids, cosmids, phage, viruses, and the like.

As used in this application, the term "a nucleic acid encoding a HOJ-1" refers to a nucleic acid molecule that has been isolated free of total cellular nucleic acid. In preferred embodiments, the invention concerns a nucleic acid sequence essentially as set forth in SEQ ID NO:1. The term "as set forth in SEQ ID NO:1" means that the nucleic acid sequence substantially corresponds to a portion of SEQ ID NO:1. The term "functionally equivalent codon" is used herein to refer to codons that encode the same amino acid, such as the six codons for arginine or serine (Table 1, below), and also refers to codons that encode biologically equivalent amino acids, as discussed in the following pages.

A "DNA segment comprising an isolated or purified HOJ-1 or other marker gene" refers to a DNA segment including HOJ-1 or other similar marker gene coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences and smaller engineered gene segments that express, or may be adapted to express, HOJ-1 or other cancer marker gene proteins, polypeptides or peptides.

TABLE 1

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |

TABLE 1-continued

| Amino Acids | | | Codons | | | | | |
|---|---|---|---|---|---|---|---|---|
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NO:1 will be sequences that are "as set forth in SEQ ID NO:1." Sequences that are essentially the same as those set forth in SEQ ID NO:1 also may be functionally defined as sequences that are capable of hybridizing to a nucleic acid segment containing the complement of SEQ ID NO:1 under standard conditions.

The DNA segments of the present invention include those encoding biologically functional equivalent HOJ-1 proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

It will also be understood that nucleic acid sequences (and their encoded amino acid sequences) may include additional residues, such as additional 5' or 3' sequences (or N- or C-terminal amino acids), and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions of any cancer marker gene, and allowing for the degeneracy of the genetic code, sequences that have between about 70% and about 80%; or more preferably, between about 81% and about 90%; or even more preferably, between about 91% and about 99% of nucleotides that are identical to the nucleotides of a disclosed sequence are thus sequences that are "essentially as set forth" in the given sequence.

Of course, it will be understood that these values will also be interpreted according to the length, function and properties of the particular nucleic acid sequence. For a nucleic acid sequence to be a biologically equivalent nucleic acid sequence, functional equivalence, not only structural equivalence, is necessary. "Functional equivalence" is defined herein as being a cancer marker sequence that is expressed in cancers.

An effective method for characterizing functional equivalence in nucleic acid sequences is hybridization. Nucleic acid sequences that are capable of hybridizing to one of the nucleic acid segments disclosed herein under relatively stringent conditions are functionally equivalent nucleic acid sequences. Suitable relatively stringent hybridization conditions will be well known to those of skill in the art and are further defined herein.

This invention thus particularly encompasses at least functional sequence analogs of the disclosed sequences and nucleic acid sequences that are hybridizable to the disclosed sequences.

b. Oligonucleotide Probes and Primers

Naturally, the present invention also encompasses DNA segments that are complementary, or essentially complementary, to the sequence set forth in SEQ ID NO:1. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 under relatively stringent conditions such as those described herein. Such sequences may encode the entire HOJ-1 protein or functional or non-functional fragments thereof The nucleic acid detection techniques and conditions described herein serve both to define the functionally equivalent nucleic acids of the invention, as outlined structurally above, and to describe certain methods by which the cancer marker gene sequences and their equivalents may be used in practical terms to identify and characterize cancer cells and tissues.

Hybridizing fragments should be of sufficient length to provide specific hybridization to a RNA or DNA tissue sample. The use of a hybridization probe of between about 10–14 or 15–20 and about 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained.

Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 300, 500, 600, 700, 800; and longer are contemplated as well. Such oligonucleotides will find use, for example, as probes in Southern and Northern blots and as primers in amplification reactions.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C.

One method of using probes and primers of the present invention is in the search for genes related to HOJ-1 or, more particularly, homologs of HOJ-1 from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidinibiotin, which are capable of being detected.

In certain embodiments, one may desire to employ a fluorescent label, electroluminescence or an enzyme tag such as urease, alkaline phosphatase or peroxidase, instead of radioactive or other environmentally undesirable reagents. In the case of enzyme tags, calorimetric indicator substrates are known which can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions.

The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

c. Gene Cloning

The sequences of the invention may have differential expression in various cancers, and have immediate uses in diagnostic and prognostic embodiments. This utility does not depend on the identity of the encoded protein or the definition of the function of the gene and/or protein. However, the markers of the invention may indeed be used to identify and isolate full length gene sequences if desired.

The use of a marker sequence to identify and isolate a full length gene sequence is most particularly exemplified herein by the use of pGAD 10 to clone HOJ-1. Any marker sequence disclosed herein, or an equivalent thereof, may be so used to clone a gene, including its regulatory elements, from a cDNA and/or genomic DNA library. The techniques of screening cDNA libraries to clone genes are now standard.

In cDNA cloning, one would obtain a high quality cDNA library, many of which, including human cDNA libraries, are readily available from commercial or other sources. The library is then plated on, for example, agarose plates containing nutrients, antibiotics and other standard ingredients. Individual colonies are then transferred to nylon or nitrocellulose membranes and a probe of the present invention is then hybridized to complementary sequences on the membranes. Hybridization is detected by radioactive or enzyme-linked tags associated with the hybridized probes.

Positive colonies are grown and sequenced by, for example, Sanger dideoxy nucleotide sequencing or similar methods, as are well known in the art. Comparison of cloned cDNA sequences with known human or animal cDNA or genomic sequences is readily performed using computer programs and databases well known to the skilled practitioner.

Further, cDNA sequences identified in the present invention are useful as hybridization probes to screen genomic DNA libraries. Once partial genomic clones have been identified, full-length genes can be isolated by "chromosomal walking", also called "overlap hybridization" (Chinault and Carbon, 1979; incorporated herein by reference). Once a partial genomic clone has been isolated using a cDNA hybridization probe, nonrepetitive segments at or near the ends of the partial genomic clone may be used as hybridization probes in further genomic library screening, ultimately allowing the isolation of entire gene sequences for the cancer markers of interest (see, e.g., Sambrook et al., 1989; incorporated herein by reference).

d. Antisense Constructs

In some cases, the HOJ-1 tumor marker may be responsible for the tumorigenic potential of the cell. Further, the homology studies performed herein suggested that HOJ-1 may be an oncogene. If this is the case, antisense treatments are one way of alleviating the cancer growth mediated by HOJ-1. Antisense technology also may be used to "knock-out" function of HOJ-1 in the development of cell lines for research, diagnostic and screening purposes.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

3. The HOJ-1 Tumor Protein

A tumor associated gene has been identified in the present invention. This antigen is encoded by a gene designated as HOJ-1. This molecule is expressed on cells having tumor phenotypes in various cancers. These cancer include, but are not limited to, melanoma, glioblastomas, astrocytomas and carcinomas of the breast, gastric, colon, pancreas, renal, ovarian, lung, prostate, hepatic, choriocarcinoma, leukemia/lymphoma, and lung carcinomas. Thus, it will be understood that the invention further provides cancer marker proteins, polypeptides and peptides with amino acid sequences encoded by the isolated nucleic acids disclosed herein, and their biological functional equivalents.

In addition to the entire HOJ-1 molecule, the present invention also relates to fragments of the polypeptide that may or may not retain the tumor (or other) phenotype. Fragments, including the N-terminus of the molecule may be generated by genetic engineering of translation stop sites within the coding region (discussed below). Alternatively, treatment of the HOJ-1 molecule with proteolytic enzymes, known as proteases, can produces a variety of N-terminal, C-terminal and internal fragments. Examples of fragments may include contiguous residues of the HOJ-1 sequence given in SEQ ID NO:2, of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

a. Structural and Functional Features of the Polypeptide

The gene for HOJ-1 encodes a 109 amino acid polypeptide. The predicted molecular weight of the molecule prior to post-translational modifications is 15 kDa. Thus, at a minimum, this molecule may be used as a standard in assays where molecule weights are being examined. When the present application refers to the function of HOJ-1 or "wild-type" activity, it is meant that the molecule in question is expressed as a malignant phenotype, i.e., one associated with any sort of abnormal growth regulation.

The amino acid sequence translated from the HOJ-1 open-reading has been determined and expressed. HOJ-1 protein binds to MAGE-1 protein. MAGE-1 protein is only expressed in cancer cells, testis and placenta. HOJ-1 expression correlates well with the expression of MAGE-1 in testis and placenta. However, it was found that HOJ-1 is expressed in MAGE-1 positive and negative cancer cells. The HOJ-1 has 64% homology to HRC1 gene (partial sequence). HRC1 gene is considered as a potential oncogene (cell growth and differentiation regulator) discovered in bladder carcinoma.

HOJ-1 was originally isolated through the two yeast hybrid assay. This assay exploited the MAGE-1 protein interaction of HOJ-1. The inventor suggests that HOJ-1 may likely interact with other MAGE family members and potentially with other tumor related proteins. Since the initial 5' sequence codons of HOJ-1 are similar by homology to the potential oncogene (cell growth and differentiation regulator) HRC1, and to the Ras-binding domain its role in cell regulatory function can also be postulated.

b. Variants of HOJ-1

Amino acid sequence variants of HOJ-1 (SEQ ID NO:2) also are encompassed by the present invention. Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See, for example, Johnson et al., "Peptide Turn Mimetics" in *BIOTECHNOLOGY AND PHARMACY*, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of HOJ-1, but with altered and even improved characteristics. For example, peptides 8 to 12-mer in length allow for HLA class I restricted cytotoxic T lymphocyte (CTL) recognition and peptides 11–24-mer in length allow for HLA class II recognition by CTL's. Such peptides generally have 1 or 2 amino acid motifs that allow specific HLA molecule binding. Substitution of amino acids to generate motifs that have stronger binding allows the generation of more immunogenic HOJ-1 related peptides.

c. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologicallyactive domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. Fusion to a polypeptide that can be used for purification of the substrate-HOJ-1 complex would serve to isolated the substrate for identification and analysis.

Examples of such fusion protein expression systems are the glutathione S-transferase (GST) system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.). The present inventor has made fusion of GST-HOJ-1 and 6×HIS-HOJ-1 for purification purposes.

Some of these systems produce recombinant polypeptides bearing only a small number of additional amino acids, which are unlikely to affect the antigenic ability of the recombinant polypeptide. For example, both the FLAG system and the 6×His system add only short sequences, both of which are known to be poorly antigenic and which do not adversely affect folding of the polypeptide to its native conformation.

In still further systems, it is possible to create fusion protein constructs to enhance immunogenicity of a HOJ-1 fusion construct to increase immunogenicity are well known to those of skill in the art, for example, a fusion of HOJ-1 with a helper antigen such as hsp70 or peptide sequences such as from Diptheria toxin chain or a cytokine such as IL2 will be useful in eliciting an immune response. In other embodiments, fusion construct can be made which will enhance the targeting of the HOJ-1 related compositions to a specific site or cell. For example, fusing HOJ-1 or a HOJ-1 type protein to a ligand will be an effective means to target the composition to a site expressing the receptor for such a ligand. In this manner the HOJ-1 or HOJ-1 related composition may be delivered into a cell via receptor mediated delivery. HOJ-1 can be attached covalently or fused to a ligand. This can be used as a mechanics for delivery into a cell. The ligand with the HOJ-1 attached may then be internalized by a receptor bearing cell.

Other fusion systems produce polypeptide hybrids where it is desirable to excise the fusion partner from the desired polypeptide. In one embodiment, the fusion partner is linked to the recombinant HOJ-1 cancer polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

In further embodiments, the gene sequence encoding the HOJ-1 cancer marker polypeptide may be first analyzed to detect putative transmembrane sequences. Such sequences are typically very hydrophobic and are readily detected by the use of standard sequence analysis software, such as Mac Vector (IBI, New Haven, Conn.). The presence of transmembrane sequences is often deleterious when a recombinant protein is synthesized in many expression systems, especially *E. coli*, as it leads to the production of insoluble aggregates that are difficult to renature into the native conformation of the protein. Deletion of transmembrane sequences typically does not significantly alter the conformation of the remaining protein structure.

Moreover, transmembrane sequences, being by definition embedded within a membrane, are inaccessible. Antibodies to these sequences will not, therefore, prove useful in vivo or in situ studies. Deletion of transmembrane-encoding sequences from the genes used for expression can be achieved by standard techniques. For example, fortuitously-placed restriction enzyme sites can be used to excise the desired gene fragment, or PCR™-type amplification can be used to amplify only the desired part of the gene.

d. Synthetic Peptides

The present invention also describes smaller HOJ-1-related peptides for use in various embodiments of the present invention. These peptides correspond to one or more antigenic determinants, or "epitopic core regions", of HOJ-1 or other related cancer antigens. Such peptides should generally be at least five or six amino acid residues in length, and may contain up to about 35–50 residues or so. Because of their relatively small size, the peptides of the invention can also be synthesized in solution or on a solid support in accordance with conventional techniques.

Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

U.S. Pat. No. 4,554,101 (Hopp, incorporated herein by reference) also teaches the identification and preparation of epitopes from primary amino acid sequences on the basis of hydrophilicity. Through the methods disclosed in Hopp, one of skill in the art would be able to identify epitopes from within any amino acid sequence encoded by any of the DNA sequences disclosed herein.

e. Antigen Compositions

The present invention also provides for the use of HOJ-1 proteins or peptides as antigens for the immunization of animals relating to the production of antibodies. It is envisioned that either HOJ-1, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH), bovine serum albumin (BSA) or lipids.

f. Recombinant Protein Expression

Irrespective of whether the cancer marker gene of the present invention is used to produce a fill length, unmodified protein, a variant, a fusion protein, a peptide and/or an epitopic core sequence, recombinant vectors evidently form further important aspects of the present invention.

The vectors will generally have the coding portion of the DNA segment, whether encoding a full length protein or smaller peptide, positioned under the control of a promoter. The promoter may be in the form of the promoter that is naturally associated with a HOJ-1 cancer marker gene, e.g., in a variety of cancer cells including melanoma, glioblastomas, astrocytomas and carcinomas of the breast, gastric, colon, pancreas, renal, ovarian, lung, prostate, hepatic, and lung cells, as may be obtained by isolating the 5' non-coding sequences located upstream of the coding segment or exon, for example, using recombinant cloning and/or PCR™ technology, in connection with the compositions disclosed herein (PCR™ technology is disclosed in U.S. Pat. No. 4,683,202 and U.S. Pat. No. 4,682,195, each incorporated herein by reference).

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a HOJ-1 cancer marker gene in its natural environment. Such promoters may include tissue promoters normally associated with other genes, and/or promoters isolated from any other bacterial, viral, eukaryotic, or mammalian cell.

Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al. (1989). The promoters employed may be constitutive, or inducible, and can be used under the appropriate conditions to direct high level expression of the introduced DNA segment, such as is advantageous in the large-scale production of recombinant proteins or peptides.

The preparation and engineering of expression vectors for use in prokaryotic or eukaryotic systems is well known to those of skill in the art. It is believed that virtually any expression vector and system may be employed in the expression of one or more cancer marker antigens of this invention.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the present invention do not exclude the possibility of employing a genomic version of a particular gene where desired.

As used herein, the terms "engineered" and "recombinant" cells are intended to refer to a cell into which an exogenous DNA segment or gene, such as a cDNA or gene encoding a cancer marker, such as HOJ-1, has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

To express a recombinant cancer marker, such as HOJ-1, in accordance with the present invention, one would prepare an expression vector that comprises the coding nucleic acid under the control of one or more promoters. To bring a coding sequence "under the control of a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and

*B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium, Serratia marcescens*, and various Pseudomonas species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used (Stinchcomb et al., 1979; Kingsman et al., 1979; Tschemper et al., 1980). This plasmid already contains the trp1 gene which provides a selection marker for a mutant strain of yeast lacking the ability to grow in tryptophan, for example ATCC No. 44076 or PEP4-1 (Jones, 1977). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms also may be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more cancer antigen coding sequences.

In a useful insect system, *Autograph californica* nuclear polyhidrosis virus (AcNPV) is used as a vector to express foreign genes. The virus grows in *Spodoptera frugiperda* cells. The HOJ-1 cancer antigen coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051, incorporated herein by reference). A useful exemplary baculovirus vector is the pBlueBac vector (Invitrogen, Sorrento, Calif.).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein, and it is reasonable to assume that cellular mechanisms modulate metastasis-related genes in response to changing times and conditions.

Different host cells have characteristic and specific mechanisms for the post-translational processing and modification of proteins. Appropriate cells lines or host systems can be chosen to ensure the correct modification and processing of the foreign protein expressed. To this end, eukaryotic host cells will often be preferred.

Expression vectors for use in such cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it also is possible, and may be desirable, to utilize promoter or control sequences normally associated with the desired HOJ-1 cancer gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments also may be used, provided there is included the approximately 250 bp sequence extending from the HindIII site toward the BgII site located in the viral origin of replication.

In cases where an adenovirus is used as an expression vector, the coding sequences may be ligated to an adenovirus transcription/ translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing HOJ-1 and related cancer antigens in infected hosts.

Specific initiation signals also may be required for efficient translation of cancer antigen coding sequences, such as HOJ-1. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators (Bittner et al., 1987).

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of recombinant HOJ-1 and related cancer-associated proteins, stable expression is preferred. For example, cell lines that stably express constructs encoding HOJ-1 may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may. be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex virus thymidine kinase (Wigler et al., 1977), hypoxanthine-guanine phosphoribosyltransferase (Szybalska et al., 1962) and adenine phosphoribosyltransferase genes (Lowy et al., 1980), in tk-, hgprt- or aprt-cells, respectively. Also, antimetabolite resistance can be used as the basis of selection for dhfr, that confers resistance to methotrexate (Wigler et al., 1980; O'Hare et al., 1981); gpt, that confers resistance to mycophenolic acid (Mulligan et al., 1981); neo, that confers resistance to the aminoglycoside G418 (Colberre-Garapin et al., 1981); and hygro, that confers resistance to hygromycin (Santerre et al., 1984).

g. Purification of Proteins

It will be desirable to purify HOJ-1 or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) and FPLC are characterized by a very rapid separation with extraordinary resolution of peaks. This is achieved by the use of very fine particles and high pressure to maintain an adequate flow rate. Separation can be accomplished in a matter of min, or at most an h. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

4. Additional Tumor Markers

Tumors are notoriously heterogeneous, particularly in advanced stages of tumor progression (Morton et al., 1993; Fidler and Hart, 1982; Nowell, 1982; Elder et al., 1989; Bystryn et al., 1985). Although tumor cells within a primary tumor or metastasis all may express the same marker gene, the level of specific mRNA expression can vary considerably (Elder et al., 1989). It is, in certain instances, necessary to employ a detection system that can cope with an array of heterogeneous markers.

Thus, while the present invention exemplifies HOJ-1 as a tumor marker, any marker that is correlated with the presence or absence of cancer may be used in combination with HOJ-1 to improve the efficacy of tumor detection and treatment. A marker, as used herein, is any proteinaceous molecule (or corresponding gene) whose production or lack of production is characteristic of a cancer cell. Depending on the particular set of markers employed in a given analysis, the statistical analysis will vary. For example, where a particular combination of markers is highly specific for melanomas or breast cancer, the statistical significance of a positive result will be high. It may be, however, that such specificity is achieved at the cost of sensitivity, i.e., a negative result may occur even in the presence of melanoma or breast cancer. By the same token, a different combination may be very sensitive, i.e., few false negatives, but has a lower specificity.

As new markers are identified, different combinations may be developed that show optimal function with different ethnic groups or sex, different geographic distributions, different stages of disease, different degrees of specificity or different degrees of sensitivity. Marker combinations also may be developed, which are particularly sensitive to the effect of therapeutic regimens on disease progression. Patients may be monitored after surgery, gene therapy, hyperthermia, immunotherapy, cytokine therapy, gene therapy, radiotherapy or chemotherapy, to determine if a specific therapy is effective.

One particularly useful combination of markers for melanoma is tyrosinase and members of the MAGE family, particularly MAGE-1 or MAGE-3. Human tyrosinase is an essential enzyme which regulates the production of melanin (Nordlund et al., 1989; Hoon et al., 1993), a group of brown or black pigments in the skin and eyes of humans. More specifically, tyrosinase catalyzes the conversion of tyrosine to Dopa and of Dopa to dopaquinone.

There are many other markers that may be used in combination with these, and other, markers. For example, β-human chorionic gonadotropin (β-HCG). β-HCG is produced by trophoblastic cells of placenta of pregnant woman and is essential for maintenance of pregnancy at the early stages (Pierce et al., 1981; Talmadge et al., 1984). β-HCG is known to be produced by trophoblastic or germ cell origin tumors, such as choriocarcinoma or testicular carcinoma cells (Madersbacher et al., 1994; Cole et al., 1983). Also ectopic expression of β-HCG has been detected by a number of different immunoassays in various tumors of non-gonadal such as breast, lung, gastric, colon, and pancreas, etc. (McManus et al., 1976; Yoshimura et al., 1994; Yamaguchi et al., 1989; Marcillac et al., 1992; Alfthan et al., 1992). Although the function of β-HCG production in these tumors is still unknown, the atavistic expression of β-HCG by cancer cells and not by normal cells of non-gonadal origin suggests it may be a potentially good marker in the detection of melanoma and breast cancer (Hoon et al., 1996; Sarantou et al., 1997).

Another exemplary example of a marker is glycosyltransferase β-1,4-N-acetylgalacto-saminyltransferase (GalNAc). GalNAc catalyzes the transfer of N-acetylgalactosamine by β1→4 linkage onto both gangliosides GM3 and GD3 to generate GM2 and GD2, respectively (Nagata et al., 1992; Furukawa et al., 1993). It also catalyzes the transfer of N-acetylgalactosamine to other carbohydrate molecules such as mucins. Gangliosides are glycosphingolipids containing sialic acids which play an important role in cell differentiation, adhesion and malignant transformation. In melanoma, gangliosides GM2 and GD2 expression, are often enhanced to very high levels and associate with tumor progression including metastatic tumors (Hoon et al., 1989; Ando et al., 1987; Carubia et al., 1984; Tsuchida et al., 1987a). Gangliosides are also expressed in melanoma, renal, lung, breast carcinoma cancer cells. The gangliosides GM2 and GD2 are immunogenic in humans and can be used as a target for specific immunotherapy such as human monoclonal antibodies or cancer vaccines (Tsuchida et al., 1987b; Irie, 1985.)

GalNAc mRNA may be used as a marker of GM2 and GD2 expression and consequently a marker of either melanoma or breast cancer cells. GalNAc is generally not expressed in normal lymphocytes, epithelial cells, melanocytes, connective tissue or lymph node cells. If detected, it is in very low levels. Prostate specific antigen is a well characterized marker for prostate cancer (Gomella et al., 1997). bcr/abl gene for leukemia is a further well characterized marker that is contemplated to be useful in combination with HOJ-1.

Other markers contemplated by the present invention include cytolytic T lymphocyte (CTL) targets. MAGE-3 is a marker identified in melanoma cells and breast carcinoma. MAGE-3 is expressed in many melanomas as well as other tumors and is a (CTL) target (Gaugler et al., 1994). MAGE-1, MAGE-2, MAGE-4, MAGE-6, MAGE-12, MAGE-Xp, and are other members of the MAGE gene family. MAGE-1 gene sequence shows 73% identity with MAGE-3 and expresses an antigen also recognized by CTL (Gaugler et al., 1994). MART-1 is another potential CTL target (Robbins et al., 1994) and also may be included in the present invention.

Other proteins and their corresponding nucleic acids related to the melanin synthesis pathway may be used as markers, such as tyrosinase related protein 1 and 2 and members of the pMel 17 gene family (Kwon et al., 1993).

MUC18, melanoma antigen gp75 (Vijayasardahi et al., 1990) and high molecular weight melanoma antigen are other markers that are useful in the identification of melanoma cells (Lehman et al., 1989; Lehman et al., 1987). MUC18 is a cell surface glycoprotein that is a member of the immunoglobulin superfamily and possesses sequence homology to neural cell adhesion molecules (NCAM). In addition, mucin family members such as MUC1, MUC2, MUC3 and MUC4 can be used. These were found to be expressed at a high level in certain tumor cell lines (Hollingsworth et al., 1994) and also may be used as markers in combination with the novel HOJ-1 marker of the present invention.

Other members of the immunoglobulin superfamily of adhesion molecules associated with the development of melanoma metastasis (Denton et al., 1992) may be utilized in the present invention. Examples include intercellular adhesion molecule-1 (ICAM-1) NCAM, VCAM-1 and ELAM. Another embodiment includes carcinoma cell related molecules and molecules associated with other metastatic diseases such as carcinoembryonic antigen and cytokeratin 20 (CEA; Lin and Guidotti, 1989).

Other carcinoma or skin cancer associated proteins and their corresponding nucleic acids also may be utilized in the present invention. Preferred examples include melanoma antigen gp75 (Vijayasardahi et al., 1990), human cytokeratin 20, high molecular weight melanoma antigen (Natali et al., 1987) and cytokeratin 19 (K19) (Datta et al., 1994). Other markers that may be useful herein include inhibitors of the cyclin-dependent kinases, (CDK). For example, CDK4 regulates progression through the $G_1$ phase of the cell cycle. The activity of CDK4 is controlled by an activating subunit, D-type cyclin, and by an inhibitory subunit, the $p16^{INK4}$ has been biochemically characterized as a protein that specifically binds to and inhibits CDK4 (Serrano et al., 1993; Serrano et al., 1995). Other CDK-inhibitory proteins that also includes p16, $p21^{WAF1}$, and $p27^{KIP1}$. This list is not intended to be exhaustive, but merely exemplary, for the type and number of potential markers which may be used in the present invention.

Preferred embodiments of the invention involve many different combinations of markers for the detection of cancer cells. Any marker that is indicative of neoplasia in cells may be included in this invention.

Many different combinations of markers for the detection of cancer cells are contemplated to be used in combination with the HOJ-1 marker of the present invention. Any marker that is indicative of neoplasia in cells may be included in this invention.

5. Nucleic Acid Detection

A variety of nucleic acid detection and/or amplification techniques are suitable for use with the probes and primers of the present invention in methods for detecting cancer cells in biological samples.

These embodiments of the invention comprise methods for the identification of metastatic cancer cells in biological samples by detecting nucleic acids that correspond to cancer cell markers and are not present in the immediate surrounding of normal cells. The biological sample can be any tissue or fluid in which cancer cells might have metastasized to.

Lymph node tissue sections, specimens, aspirates and biopsies also may be used. Further suitable examples are bone marrow aspirates, bone marrow biopsies, spleen tissues, fine needle aspirates and even skin biopsies. Other suitable examples are fluids, including samples where the body fluid is peripheral blood, serum, lymph fluid, seminal fluid or urine. Stools may even be used.

The nucleic acids used as a template for detection are isolated from cells contained in the biological sample, according to standard methodologies (Sambrook et al., 1989). The nucleic acid may be genomic DNA or fractionated or whole cell RNA.

a. Northern Blotting

In certain embodiments, RNA detection is by Northern blotting, i.e., hybridization with a labeled probe. The techniques involved in Northern blotting are well known to those of skill in the art and can be found in many standard books on molecular protocols (e.g., Sambrook et al., 1989).

Briefly, RNA is separated by gel electrophoresis. The gel is then contacted with a membrane, such as nitrocellulose, permitting transfer of the nucleic acid and non-covalent binding. Subsequently, the membrane is incubated with, e.g., a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

b. Amplification and Detection i. PCR™

In one detection embodiment, RNA is used directly as a template for PCR™ amplification. In PCR™, pairs of primers that selectively hybridize to nucleic acids corresponding to cancer-specific markers are used under conditions that permit selective hybridization. The term primer, as used herein, encompasses any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

The primers are used in any one of a number of template dependent processes to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, each incorporated herein by reference, and in Innis et al. (1990, incorporated herein by reference).

In PCR™, two primer sequences are prepared which are complementary to regions on opposite complementary strands of the cancer marker sequence. The primers will hybridize to form a nucleic acid:primer complex if the cancer marker sequence is present in a sample. An excess of deoxynucleoside triphosphates are added to a reaction mixture along with a DNA polymerase, e.g., Taq polymerase, that facilitates template-dependent nucleic acid synthesis.

If the marker sequence:primer complex has been formed, the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated. These multiple rounds of amplification, referred to as "cycles", are conducted until a sufficient amount of amplification product is produced.

Next, the amplification product is detected. In certain applications, the detection may be performed by visual means. Alternatively, the detection may involve indirect identification of the product via chemiluminescence, electroluminescence, radioactive scintigraphy of incorporated radiolabel or fluorescent label or even via a system using electrical or thermal impulse signals (Affymax technology).

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641, filed Dec. 21, 1990.

ii. Other Amplification Techniques

Another method for amplification is the ligase chain reaction ("LCR"), disclosed in European Patent Application No. 320,308, incorporated herein by reference. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference, describes a method similar to LCR for binding probe pairs to a target sequence.

Qbeta Replicase, described in PCT Patent Application No. PCT/US87/00880, also may be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[α-thio]-triphosphates in one strand of a restriction site also may be useful in the amplification of nucleic acids in the present invention. Such an amplification method is described by Walker et al. (1992, incorporated herein by reference).

Strand Displacement Amplification (SDA) is another method of carrying out isothermal amplification of nucleic acids which involves multiple rounds. of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA.

Target specific sequences can also be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

Other amplification methods, as described in British Patent Application No. GB 2,202,328, and in PCT Patent Application No. PCT/US89/01025, each incorporated herein by reference, may be used in accordance with the present invention. In the former application, "modified" primers are used in a PCR™ like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; PCT Patent Application WO 88/10315, each incorporated herein by reference).

In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

Davey et al., European Patent Application No. 329,822 (incorporated herein by reference) disclose a nucleic acid amplification process involving cyclically synthesizing single-stranded RNA ("ssRNA"), ssDNA, and double-stranded DNA (dsDNA), which may be used in accordance with the present invention.

The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can-be chosen to be in the form of either DNA or RNA.

Miller et al., PCT Patent Application WO 89/06700 (incorporated herein by reference) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts.

Other suitable amplification methods include "race" and "one-sided PCR™" (Frohman, 1990; Ohara et al., 1989, each herein incorporated by reference). Methods based on ligation of two (or more) oligonucleotides in the presence of nucleic acid having the sequence of the resulting "di-oligonucleotide", thereby amplifying the di-oligonucleotide, also may be used in the amplification step of the present invention (Wu et al., 1989, incorporated herein by reference).

iii. Separation Methods

Following amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982). In yet another alternative, labeled cDNA products, such as biotin or antigen can be captured with beads bearing avidin or antibody, respectively.

iv. Identification Methods

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, where the other member of the binding pair carries a detectable moiety.

V. In Situ Hybridization

In a particular embodiment, the present invention contemplates the detection of abnormalities related to cancer cells in biological samples. In order to do this the present inventor has mapped the gene for HOJ-1 to chromosome 12. Mapping the positions of DNA probes within a chromosome or relative to other probes can be accomplished rapidly using in situ hybridization techniques (Pinkel et al., 1986, U.S. Pat. No. 5,633,365 and U.S. Pat. No. 5,665,549, each incorporated herein by reference).

Briefly, if a gene sequence is available, for example having been isolated from a cosmid, a phage clone or as a cDNA sequence, its chromosomal location may be visualized using in situ hybridization of the cloned DNA to a metaphase spread of chromosomes. The probe DNA may be labeled radioactively or non-radioactively. The most common radioactive labels used for hybridization studies are 32P, 35S and 3H. A popular method of non-radiolabeling is using a fluorescent moiety. fluorescent in situ hybridization (FISH) involves the incorporation of a substance such as biotinylated UTP into the DNA in a nick-translation reaction as the probe is being synthesized. The probe DNA is then denatured and allowed to hybridize, under appropriate conditions, with denatured chromosomal DNA. In this way the site of hybridization can be detected by a fluorescently labeled avidin (FITC-avidin) which binds to the biotin on the biotinylated UTP. The signal may be increased by one or more rounds of amplification to identify the unique molecule on the chromatid. It is also possible to use different types of fluorescent labels to look at the positioning of several different probes at the same time and to order their position with respect to each other and to the centromere. Given the description of HOJ-1 in the present invention, one of skill in the art will be able to perform such hybridization studies without undue experimentation. By way of example, the individual of skill in the art is referred to "Visualization of Nucleic Acids" (Gerad Morel, Ed., CRC publ., 1995) or any other standard molecular biology text for a more comprehensive treatise on hybridization techniques and protocols. Examples of such hybridization studies and data generated therefrom are given herin below.

Using FISH techniques, the inventor has located the HOJ-1 gene to the 12p12.3 location on chromosome 12.

In situ hybridization can also be used to detect abnormal nucleic acid sequence copy numbers in one or more genomes wherein repetitive sequences that bind to multiple loci in a reference chromosome spread are either substantially removed and/or their hybridization signals suppressed.

Techniques such as FISH and comparative genomic hybridization (CGH; U.S. Pat. No. 5,665,549, incorporated herein by reference) provide methods of determining the relative number of copies of nucleic acid sequences in one or more subject genomes or portions thereof (for example, a tumor cell) as a function of the location of those sequences in a reference genome (for example, a normal human genome). The intensity(ies) of the signals from each labeled subject nucleic acid and/or the differences in the ratios between different signals from the labeled subject nucleic acid sequences are compared to determine the relative copy numbers of the nucleic acid sequences in the one or more subject genomes as a function of position along the reference chromosome spread. Thus, if there is an amplification, duplication and/or deletion in a cancer subject's genome, it can be readily can be detected.

d. Molecular Biological Detection Kits

The materials and reagents required for detecting cancer cells in a biological sample may be assembled together in a kit.

The kits of the invention will generally comprise one or more preselected primers or probes specific for cancer markers, such as HOJ-1. Preferably, the kits will comprise, in suitable container means, one or more cancer nucleic acid probes or primers and means for detecting nucleic acids. In certain embodiments, such as in kits for use in Northern blotting, the means for detecting the nucleic acids may be a label, such as a radiolabel, that is linked to a nucleic acid probe itself.

Preferred kits are those suitable for use in PCR™. In PCR™ kits, two primers will preferably be provided that have sequences from, and that hybridize to, spatially distinct regions of the cancer marker gene, such as HOJ-1. Preferred pairs of primers for amplifying nucleic acids are selected to amplify the sequences specified herein. Also included in PCR™ kits may be enzymes suitable for amplifying nucleic acids, including various polymerases (RT, Taq, etc.), deoxynucleotides and buffers to provide the necessary reaction mixture for amplification.

The molecular biological detection kits of the present invention, although containing at least one novel cancer marker nucleic acid, as disclosed herein, also may contain one or more of a variety of other cancer marker gene sequences as described above. By way of example only, one may mention prostate specific antigen (PSA) sequences, probes and primers. Thus the cancer markers of this invention, such as HOJ-1, would be one of a panel of cancer markers in the kit.

In each case, the kits will preferably comprise distinct containers for each individual reagent and enzyme, as well as for each cancer probe or primer pair. Each biological agent will generally be suitable aliquoted in their respective containers.

The container means of the kits will generally include at least one vial or test tube. Flasks, bottles and other container means into which the reagents are placed and aliquoted are also possible. The individual containers of the kit will preferably be maintained in close confinement for commercial sale. Suitable larger containers may include injection or blow-molded plastic containers into which the desired vials are retained. Instructions may be provided with the kit.

e. RNA Fingerprinting and Quantitation

RNA fingerprinting is a method by which RNAs isolated from many different tissues, cell types or treatment groups can be sampled simultaneously to identify RNAs whose relative abundances vary. Two forms of this technology were developed simultaneously and reported in 1992 as RNA fingerprinting by differential display (Liang and Pardee, 1992; Welsh et al., 1992). See also, Liang and Pardee, U.S. Pat. No. 5,262,311, incorporated herein by reference, and Donahue et. al. (1994, incorporated herein by reference).

All forms of RNA fingerprinting by PCR™ are theoretically similar but differ in their primer design and application. The most striking difference between differential display and other methods of RNA fingerprinting is that differential display utilizes anchoring primers that hybridize to the poly A tails of mRNAs. As a consequence, the PCR™ products amplified in differential display are biased towards the 3' untranslated regions of mRNAs.

The basic technique of differential display has been described in detail (Liang and Pardee, 1992). Total cell RNA is primed for first strand reverse transcription with an anchoring primer composed of oligo dT. The oligo dT primer is extended using a reverse transcriptase, for example, Moloney Murine Leukemia Virus (MMLV) reverse transcriptase. The synthesis of the second strand is primed with an arbitrarily chosen oligonucleotide, using reduced stringency conditions. Once the double-stranded cDNA has been synthesized, amplification proceeds by standard PCR™ techniques, utilizing the same primers. The resulting DNA fingerprint is analyzed by gel electrophoresis and ethidium bromide staining or autoradiography. A side by side comparison of fingerprints obtained from different cell derived RNAs using the same oligonucleotide primers identifies mRNAs that are differentially expressed.

RNA fingerprinting technology has been demonstrated as being effective in identifying genes that are differentially expressed in cancer (Liang et al., 1992; Wong et al., 1993; Sager et al., 1993; Mok et al., 1994; Watson et al., 1994; Chen et al., 1995; An et al., 1995). The present invention utilizes the RNA fingerprinting technique to identify genes that are differentially expressed in different metastatic forms of cancer. These studies utilized RNAs isolated from tumor-derived cell lines that behave as tumors cells with different metastatic potential.

The underlying concept of these studies was that genes that are differentially expressed in cells with different metastatic potentials can be used as indicators of metastatic potential. Since metastasis is a prerequisite for cancer progression to life threatening pathologies, indicators of metastatic potential are likely to be indicators of pathological potential.

Although a number of useful cancer markers have already been identified herein, the present invention further provides methods for the identification of still more HOJ-1-like cancer markers.

i. Relative Quantitative RT-PCR™ Reverse transcription (RT) of RNA to cDNA followed by relative quantitative or semi-quantitative PCR™ (RT-PCR™) can be used to determine the relative concentrations of specific mRNA species in a series of total cell RNAs isolated from the cancer cells.

By determining that the concentration of a specific mRNA species varies, it is shown that the gene encoding the specific mRNA species is differentially expressed. This technique can be used to confirm that mRNA transcripts shown to be differentially regulated by RNA fingerprinting are differentially expressed in cancer progression.

In PCR™, the number of molecules of the amplified target DNA increase by a factor approaching two with every cycle of the reaction until some reagent becomes limiting. Thereafter, the rate of amplification becomes increasingly diminished until there is not an increase in the amplified target between cycles. If one plots a graph on which the cycle number is on the X axis and the log of the concentration of the amplified target DNA is on the Y axis, one observes that a curved line of characteristic shape is formed by connecting the plotted points.

Beginning with the first cycle, the slope of the line is positive and constant. This is said to be the linear portion of the curve. After some reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ is directly proportional to the starting concentration of the target before the PCR™ was begun. By determining the concentration of the PCR™ products of the target DNA in PCR™ reactions that have completed the same number of cycles and are in their linear ranges, it is possible to determine the relative concentrations of the specific target sequence in the original DNA mixture.

If the DNA mixtures are cDNAs synthesized from RNAs isolated from different cells, the relative abundances of the specific mRNA from which the target sequence was derived can be determined for the respective tissues or cells. This direct proportionality between the concentration of the PCR™ products and the relative mRNA abundances is only true in the linear range portion of the PCR™ reaction.

The final concentration of the target DNA in the plateau portion of the curve is determined by the availability of reagents in the reaction mix and is independent the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ study to successfully determine the relative abundances of a particular mRNA species is that relative concentrations of the amplifiable cDNAs must be normalized to some independent standard. The goal of an RT-PCR™ study is to determine the abundance of a particular mRNA species relative to the average abundance of all mRNA species in the sample. In such studies, mRNAs for β-actin, asparagine synthetase and lipocortin II may be used as external and internal standards to which the relative abundance of other mRNAs are compared.

Most protocols for competitive PCR™ utilize internal PCR™ internal standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The discussion above describes the theoretical considerations for an RT-PCR™ assay for clinically derived materials. The problems inherent in clinical samples are that they are of variable quantity (making normalization problematic), and that they are of variable quality (necessitating the co-amplification of a reliable internal control, preferably of larger size than the target).

Both of the foregoing problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies are available that use a more conventional relative quantitative RT-PCR™ with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This is very important since this assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ with an internal standard.

One reason for this is that without the internal standard/competitor, all of the reagents can be converted into a single PCR™ product in the linear range of the amplification curve, increasing the sensitivity of the assay. Another reason is that with only one PCR™ product, display of the product on an electrophoretic gel or some other display method becomes less complex, has less background and is easier to interpret.

6. Antibodies a. Antibody Generation

It will be understood that polyclonal or monoclonal antibodies specific for the HOJ-1 and related proteins that are expressed in cancer cells will have utilities in several applications. These include the production of diagnostic kits for use in detecting and diagnosing cancer. An additional use is to link such antibodies to therapeutic agents, such as chemotherapeutic agents, and to administer the antibodies to individuals with cancer, thereby selectively targeting the cancer cells for destruction.

Thus the invention further provides antibodies specific for the proteins, polypeptides or peptides, such as HOJ-1, encoded by the nucleic acid segments disclosed herein and their equivalents. Means for preparing and characterizing antibodies are well known in the art (See, e.g., Antibodies: A Laboratory Manual, Cold Spring Harbor Laboratory, 1988; incorporated herein by reference). Antibodies to HOJ-1 peptides or protein have already been generated using such standard techniques.

The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention and collecting antisera from that immunized animal.

A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed Mycobacterium tuberculosis), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The procured blood is allowed to coagulate and then centrifuged to separate serum components from whole cells and blood clots. The serum may be used as is for various applications or else the desired antibody fraction may be purified by well-known methods, such as affinity chromatography using another antibody or a peptide bound to a solid matrix or protein A followed by antigen (peptide) affinity column for purification.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified HOJ-1 protein, polypeptide or peptide. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep, goat, monkey cells also is possible. The use of rats may provide certain advantages (Goding, 1986, pp. 60–61), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens or lymph nodes. Spleen cells and lymph node cells are preferred, the former because they are a rich source of antibody-producing cells that are in the dividing plasmablast stage.

Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984; each incorporated herein by reference). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding pp. 71–74, 1986).

Fusion procedures usually produce viable hybrids at low frequencies, about $1\times10^{-6}$ to $1\times10^{-8}$. However, this does not pose a problem; as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways.

A sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration.

The individual cell lines could also be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Humanized monoclonal antibodies are antibodies of animal origin that have been modified using genetic engineering techniques to replace constant region and/or variable region framework sequences with human sequences, while retaining the original antigen specificity. Such antibodies are commonly derived from rodent antibodies with specificity against human antigens. such antibodies are generally useful for in vivo therapeutic applications. This strategy reduces the host response to the foreign antibody and allows selection of the human effector functions.

The techniques for producing humanized immunoglobulins are well known to those of skill in the art. For example U.S. Pat. No. 5,693,762 discloses methods for producing, and compositions of, humanized immunoglobulins having one or more complementarity determining regions (CDR's). When combined into an intact antibody, the humanized immunoglobulins are substantially non-immunogenic in humans and retain substantially the same affinity as the donor immunoglobulin to the antigen, such as a protein or other compound containing an epitope.

Other U.S. patents, each incorporated herein by reference, that teach the production of antibodies useful in the present invention include U.S. Pat. No. 5,565,332, which describes the production of chimeric antibodies using a combinatorial approach; U.S. Pat. No. 4,816,567 which describes recombinant immunoglobin preparations and U.S. Pat. No. 4,867,973 which describes antibody-therapeutic agent conjugates.

U.S. Pat. No. 5,565,332 describes methods for the production of antibodies, or antibody fragments, which have the same binding specificity as a parent antibody but which have increased human characteristics. Humanized antibodies may be obtained by chain shuffling, perhaps using phage display technology, in as much as such methods will be useful in the present invention the entire text of U.S. Pat. No. 5,565,332 is incorporated herein by reference. Human antibodies may also be produced by transforming B cells with EBV and subsequent cloning of secretors as described by Hoon et al., (1993).

b. Cross-Reactive Antibodies and Epitopes

The invention further encompasses anti-HOJ-1 cancer marker antibodies and antibody-based compositions, such as antibody conjugates and immunotoxins, that bind to the same antigens and/or epitopes as the antibodies disclosed herein (e.g., those raised to the peptides of SEQ ID NO:2). Such antibodies may be of the polyclonal or monoclonal type, with monoclonals being generally preferred.

The identification of an antibody that binds to a cancer antigen or epitope, such as to HOJ-1 or an epitope thereof, in substantially the same manner as an antibody of the invention is a fairly straightforward matter. This can be readily determined using any one of variety of immunological screening assays in which antibody competition can be assessed.

For example, where the test antibodies to be examined are obtained from different source animals, or are even of a different isotype, a simple competition assay may be employed in which the control and test antibodies are premixed and then applied to an antigen composition. By "antigen composition" is meant any composition that contains a HOJ-1 or related cancer antigen as described herein. Thus, protocols based upon ELISAs and Western blotting are suitable for use in such simple competition studies.

In such embodiments, one would pre-mix the control antibodies with varying amounts of the test antibodies (e.g., 1:1, 1:10 and 1:100) for a period of time prior to applying to an antigen composition, such as an antigen-coated well of an ELISA plate or an antigen adsorbed to a membrane (as in dot blots and Western blots). By using species or isotype secondary antibodies one will be able to detect only the bound control antibodies, the binding of which will be reduced by the presence of a test antibody that recognizes the same epitope/antigen.

In conducting an antibody competition study between a control antibody, such as an anti-HOJ-1 antibody, and any test antibody, one may first label the control with a detectable label, such as, e.g., biotin or an enzymatic, radioactive or fluorescent label, to enable subsequent identification. In these cases, one would incubate the labeled control antibodies with the test antibodies to be examined at various ratios (e.g., 1:1, 1:10 and 1:100) and, after a suitable period of time, one would then assay the reactivity of the labeled control antibodies and compare this with a control value in which no potentially competing test antibody was included in the incubation.

The assay may again be any one of a range of immunological assays based upon antibody hybridization, and the control antibodies would be detected by means of detecting their label, e.g., using streptavidin in the case of biotinylated antibodies or by using a chromogenic substrate in connection with an enzymatic label or by simply detecting a radioactive or fluorescent label. An antibody that binds to substantially the same epitope as the control antibodies will be able to effectively compete for binding and thus will significantly reduce control antibody binding, as evidenced by a reduction in bound label.

The reactivity of the labeled control antibodies in the absence of any test antibody would be the control high value. The control low value would be obtained by incubating the labeled antibodies with unlabelled antibodies of the same type, when competition would occur and reduce binding of the labeled antibodies. A significant reduction in labeled antibody reactivity in the presence of a test antibody is indicative of a test antibody that recognizes the same epitope, i.e., one that "cross-reacts" with the labeled antibody. A significant reduction is a reproducible, i.e., consistently observed, reduction in binding.

C. Antibody Conjugates

Antibody conjugates in which a HOJ-1 cancer marker antibody is linked to a detectable label or a cytotoxic agent form further aspects of the invention. Diagnostic antibody conjugates may be used both in vitro diagnostics, as in a variety of immunoassays, and in vivo diagnostics, such as in imaging technology.

Certain antibody conjugates include those intended primarily for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

d. Antibodies for Use in Vitro Also may be Radiolabeled Antibody Conjugates.

In using an antibody-based molecule as an in vivo diagnostic agent to provide an image of, for example, breast, gastric, colon, pancreas, renal, ovarian, lung, prostate, hepatic, and lung cancer or respective metastases, magnetic resonance imaging, X-ray imaging, computerized emission tomography and such technologies may be employed. In the antibody-imaging constructs of the invention, the antibody portion used will generally bind to the cancer marker, such as HOJ-1, and the imaging agent will be an agent detectable upon imaging, such as a paramagnetic, radioactive or fluorescent agent.

Many appropriate imaging agents are known in the art, as are methods for their attachment to antibodies (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the antibody (U.S. Pat. No. 4,472,509). Monoclonal antibodies also may be reacted with an enzyme in the presence of a coupling agent such as glutaraldehyde or periodate. Conjugates with fluorescein markers are prepared in the presence of these coupling agents or by reaction with an isothiocyanate.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred.

Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled monoclonal antibodies of the present invention may be produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99m}$ by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as SNCl$_2$, a buffer solution such as sodium-potassium phthalate solution, and the antibody.

Intermediary functional groups which are often used to bind radioisotopes which exist as metallic ions to antibody are diethylenetriaminepentaacetic acid (DTPA) and ethylene diaminetetracetic acid (EDTA).

Fluorescent labels include rhodamine, fluorescein isothiocyanate and renographin.

e. Immunotoxins

The invention further provides immunotoxins in which an antibody that binds to a cancer marker, such as HOJ-1, is linked to a cytotoxic agent. Immunotoxin technology is fairly well-advanced and known to those of skill in the art. Immunotoxins are agents in which the antibody component is linked to another agent, particularly a cytotoxic or otherwise anticellular agent, having the ability to kill or suppress the growth or cell division of cells.

As used herein, the terms "toxin" and "toxic moiety" are employed to refer to any cytotoxic or otherwise anticellular agent that has such a killing or suppressive property. Toxins are thus pharmacologic agents that can be conjugated to an antibody and delivered in an active form to a cell, wherein they will exert a significant deleterious effect.

The preparation of immunotoxins is, in general, well known in the art (see, e.g., U.S. Pat. No. 4,340,535, incorporated herein by reference). It also is known that while IgG based immunotoxins will typically exhibit better binding capability and slower blood clearance than their Fab' counterparts, Fab' fragment-based immunotoxins will generally exhibit better tissue penetrating capability as compared to IgG based immunotoxins.

Exemplary anticellular agents include chemotherapeutic agents, radioisotopes as well as cytotoxins. Example of chemotherapeutic agents are hormones such as steroids; antimetabolites such as cytosine arabinoside, fluorouracil, methotrexate or aminopterin; anthracycline; mitomycin C; vinca alkaloids; demecolcine; etoposide; mithramycin; or alkylating agents such as chlorambucil or melphalan.

Preferred immunotoxins often include a plant-, fungal- or bacterial-derived toxin, such as an A chain toxin, a ribosome inactivating protein, α-sarcin, aspergillin, restirictocin, a ribonuclease, diphtheria toxin or pseudomonas exotoxin, to mention just a few examples. The use of toxin-antibody constructs is well known in the art of immunotoxins, as is their attachment to antibodies. Of course, combinations of the various toxins could also be coupled to one antibody molecule, thereby accommodating variable or even enhanced cytotoxicity.

One type of toxin for attachment to antibodies is ricin, with deglycosylated ricin A chain being particularly preferred. As used herein, the term "ricin" is intended to refer to ricin prepared from both natural sources and by recombinant means. Various 'recombinant' or 'genetically engineered' forms of the ricin molecule are known to those of skill in the art, all of which may be employed in accordance with the present invention.

Deglycosylated ricin A chain (dgA) is preferred because of its extreme potency, longer half-life, and because it is economically feasible to manufacture it a clinical grade and scale (available commercially from Inland Laboratories, Austin, Tex.). Truncated ricin A chain, from which the 30 N-terminal amino acids have been removed by Nagarase (Sigma), also may be employed.

Linking or coupling one or more toxin moieties to an antibody may be achieved by a variety of mechanisms, for example, covalent binding, affinity binding, intercalation, coordinate binding and complexation. Preferred binding methods are those involving covalent binding, such as using chemical cross-linkers, natural peptides or disulfide bonds.

The covalent binding can be achieved either by direct condensation of existing side chains or by the incorporation of external bridging molecules. Many bivalent or polyvalent agents are useful in coupling protein molecules to other proteins, peptides or amine functions. Examples of coupling agents are carbodiimides, diisocyanates, glutaraldehyde, diazobenzenes, and hexamethylene diamines. This list is not intended to be exhaustive of the various coupling agents known in the art but, rather, is exemplary of the more common coupling agents that may be used.

In preferred embodiments, it is contemplated that one may wish to first derivatize the antibody, and then attach the toxin component to the derivatized product. As used herein, the term "derivatize" is used to describe the chemical modification of the antibody substrate with a suitable cross-linking agent. Examples of cross-linking agents for use in this manner include the disulfide-bond containing linkers SPDP (N-succinimidyl-3-(2-pyridyldithio)propionate) and SMPT (4-succinimidyl-oxycarbonyl-α-methyl-α(2-pyridyldithio)toluene).

Biologically releasable bonds are particularly important to the realization of a clinically active immunotoxin in that the toxin moiety must be capable of being released from the antibody once it has entered the target cell. Numerous types of linking constructs are known, including simply direct disulfide bond formation between sulfhydryl groups contained on amino acids such as cysteine, or otherwise introduced into respective protein structures, and disulfide linkages using available or designed linker moieties.

Numerous types of disulfide-bond containing linkers are known which can successfully be employed to conjugate toxin moieties to antibodies, however, certain linkers are generally preferred, such as, for example, sterically hindered disulfide bond linkers are preferred due to their greater stability in vivo, thus preventing release of the toxin moiety prior to binding at the site of action. A particularly preferred cross-linking reagent is SMPT, although other linkers such as SATA, SPDP and 2-iminothiolane also may be employed.

Once conjugated, it will be important to purify the conjugate so as to remove contaminants such as unconjugated A chain or antibody. It is important to remove unconjugated A chain because of the possibility of increased toxicity. Moreover, it is important to remove unconjugated antibody to avoid the possibility of competition for the antigen between conjugated and unconjugated species. In any event, a number of purification techniques have been found to provide conjugates to a sufficient degree of purity to render them clinically useful.

In general, the most preferred technique will incorporate the use of Blue-Sepharose with a gel filtration or gel permeation step. Blue-Sepharose is a column matrix composed of Cibacron Blue 3GA and agarose, which has been found to be useful in the purification of immunoconjugates. The use of Blue-Sepharose combines the properties of ion exchange with A chain binding to provide good separation of conjugated from unconjugated binding. The Blue-Sepharose allows the elimination of the free (non conjugated) antibody from the conjugate preparation. To eliminate the free (unconjugated) toxin (e.g., dgA) a molecular exclusion chromatography step may be used using either conventional gel filtration procedure or high performance liquid chromatography.

After a sufficiently purified conjugate has been prepared, one will generally desire to prepare it into a pharmaceutical composition that may be administered parenterally. This is done by using for the last purification step a medium with a suitable pharmaceutical composition. Such formulations will typically include pharmaceutical buffers, along with excipients, stabilizing agents and such like. The pharmaceutically acceptable compositions will be sterile, non-immunogenic and non-pyrogenic. Details of their preparation are well known in the art and are further described herein. It will be appreciated that endotoxin contamination should be kept minimally at a safe level, for example, less that 0.5 ng/mg protein.

Suitable pharmaceutical compositions in accordance with the invention will generally comprise from about 10 to about 100 mg of the desired conjugate admixed with an acceptable pharmaceutical diluent or excipient, such as a sterile aqueous solution, to give a final concentration of about 0.25 to about 2.5 mg/ml with respect to the conjugate.

As mentioned above, the cancer marker antibodies of the invention may be linked to one or more chemotherapeutic agents, such as anti-tumor drugs, cytokines, antimetabolites, alkylating agents, hormones, nucleic acids and the like, which may thus be targeted to a HOJ-1 expressing cancer cell using the antibody conjugate. The advantages of antibody-conjugated agents over their non-antibody conjugated counterparts is the added selectivity afforded by the antibody.

In analyzing the variety of chemotherapeutic and pharmacologic agents available for conjugating to an antibody, one may wish to particularly consider those that have been previously shown to be successfully conjugated to antibodies and to function pharmacologically. Exemplary antineoplastic agents that have been used include doxorubicin, daunomycin, methotrexate, vinblastine. Moreover, the attachment of other agents such as neocarzinostatin, macromycin, trenimon and α-amanitin has also been described. The lists of suitable agents presented herein are, of course, merely exemplary in that the technology for attaching pharmaceutical agents to antibodies for specific delivery to tissues is well established.

Thus, it is generally believed to be possible to conjugate to antibodies any pharmacologic agent that has a primary or secondary amine group, hydrazide or hydrazine group, carboxyl alcohol, phosphate, or alkylating group available for binding or cross-linking to the amino acids or carbohydrate groups of the antibody. In the case of protein structures, this is most readily achieved by means of a cross linking agent, as described above for the immunotoxins. Attachment also may be achieved by means of an acid labile acyl hydrazone or cis aconityl linkage between the drug and the antibody, or by using a peptide spacer such as L-Leu-L-Ala-L-Leu-L-Ala, between the γ-carboxyl group of the drug and an amino acid of the antibody.

7. Immunological Detection
a Immunoassays

The anti-cancer marker antibodies of the invention, as exemplified by anti-HOJ-1 antibodies, are useful in various diagnostic and prognostic applications connected with the detection and analysis of cancer.

In still further embodiments, the present invention thus concerns immunodetection methods for binding, purifying, removing, quantifying or otherwise generally detecting biological components. The encoded proteins or peptides of the present invention may be employed to detect antibodies having reactivity therewith, or, alternatively, antibodies prepared in accordance with the present invention, may be employed to detect the encoded proteins or peptides, such as HOJ-1.

The steps of various useful immunodetection methods have been described in the scientific literature, such as, e.g., Nakamura et al. (1987; incorporated herein by reference). Immunoassays, in their most simple and direct sense, are binding assays. Certain preferred immunoassays are the various types of enzyme linked immunosorbent assays (ELISAs), radioimmunoassays (RIA) and immunobead capture assay. Immunohistochemical detection using tissue sections also is particularly useful. However, it will be readily appreciated that detection is not limited to such techniques, and Western blotting, dot blotting, FACS analyses, and the like also may be used in connection with the present invention.

In general, immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods of this invention include methods for detecting or quantifying the amount of a reactive component in a sample, which methods require the detection or quantitation of any immune complexes formed during the binding process. Here, one would obtain a sample suspected of containing a HOJ-1 or related cancer marker protein, peptide or a corresponding antibody, and contact the sample with an antibody or encoded protein or peptide, as the case may be, and then detect or quantify the amount of immune complexes formed under the specific conditions.

In terms of antigen detection, the biological sample analyzed may be any sample that is suspected of containing a cancer-specific antigen, e.g., HOJ-1, such as a melanoma, glioblastoma, astrocytoma and carcinoma of the breast, gastric, colon, pancreas, renal, ovarian, lung, prostate, hepatic, lung, lymph node or bone marrow tissue section or specimen, a homogenized tissue extract, an isolated cell, a cell membrane preparation, separated or purified forms of any of the above protein-containing compositions, or even any biological fluid that comes into contact with cancer tissues, including blood, lymphatic fluid, seminal fluid and urine.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present, such as HOJ-1. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The encoded protein, peptide or corresponding antibody employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

The immunodetection methods of the present invention have evident utility in the diagnosis of cancer. Here, a biological or clinical sample suspected of containing either the encoded protein or peptide or corresponding antibody is used. However, these embodiments also have applications to non-clinical samples, such as in the titering of antigen or antibody samples, in the selection of hybridomas, and the like.

b. ELISAs

As noted, it is contemplated that the cancer proteins or peptides of the invention, such as HOJ-1, will find utility in ELISAs.

In one exemplary ELISA, antibodies binding to the encoded proteins of the invention are immobilized onto a selected surface exhibiting protein affinity, such as a well in a polystyrene microtiter plate. Then, a test composition suspected of containing the cancer disease marker antigen, e.g., HOJ-1, such as a clinical sample, is added to the wells. After binding and washing to remove non-specifically bound immunocomplexes, the bound antigen may be detected.

Detection is generally achieved by the addition of a second antibody specific for the target protein, that is linked to a detectable label. This type of ELISA is a simple "sandwich ELISA". Detection also may be achieved by the addition of a second antibody, followed by the addition of a third antibody that has binding affinity for the second antibody, with the third antibody being linked to a detectable label.

In another exemplary ELISA, the samples suspected of containing the cancer disease marker antigen, such as HOJ-1, are immobilized onto the well surface and then contacted with the antibodies of the invention. After binding and washing to remove non-specifically bound immunecomplexes, the bound antibody is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Another ELISA in which the proteins or peptides, such as HOJ-1, are immobilized, involves the use of antibody competition in the detection. In this ELISA, labeled antibodies are added to the wells, allowed to bind to the HOJ-1 or related cancer marker protein, and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immunecomplexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control human cancer and/or clinical or biological sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

"Under conditions effective to allow immunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 h, at temperatures preferably on the order of 25° to 27° C., or may be overnight at about 4° C. or so.

Following all incubation steps in an ELISA, the contacted surface is washed so. as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 h at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

In other embodiments, solution-phase competition ELISA is also contemplated. Solution phase ELISA involves attachment of HOJ-1 to a bead, for example a magnetic bead. The bead is then incubated with sera from human and animal origin. After a suitable incubation period to allow for specific interactions to occur, the beads are washed. The specific type of antibody is the detected with an antibody indicator conjugate. The beads are washed and sorted. This complex is the read on an appropriate instrument (fluorescent, electroluminescent, spectrophotometer, depending on the conjugating moiety). The level of antibody binding can thus by quantitated and is directly related to the amount of signal present.

c. Immunohistochemistry

The antibodies of the present invention, such as anti-HOJ-1 antibodies, also may be used in conjunction with both fresh-frozen and formalin-fixed, paraffin-embedded tissue blocks prepared from study by immunohistochemistry (IHC). For example, each tissue block consists of 50 mg of residual "pulverized" tumor. The method of preparing tissue blocks from these particulate specimens has been successfully used in previous IHC studies of various prognostic factors, e.g., in breast, and is well known to those of skill in the art (Brown-et al., 1990; Abbondanzo et al., 1990; Allred et al., 1990).

Briefly, frozen-sections may be prepared by rehydrating 50 ng of frozen "pulverized" tumor at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections containing an average of about 500 remarkably intact tumor cells.

Permanent-sections may be prepared by a similar method involving rehydration of the 50 mg sample in a plastic microfuge tube; pelleting; resuspending in 10% formalin for 4 h fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

d. FACS Analyses

Fluorescent activated cell sorting, flow cytometry or flow microfluorometry provides the means of scanning individual cells for the presence of an antigen, such as HOJ-1. The method employs instrumentation that is capable of activating, and detecting the excitation emissions of labeled cells in a liquid medium.

FACS is unique in its ability to provide a rapid, reliable, quantitative, and multiparameter analysis on either living or fixed cells. The cancer antibodies of the present invention provide a useful tool for the analysis and quantitation of antigenic cancer markers of individual cells.

Cells would generally be obtained by biopsy, single cell suspension in blood or culture. FACS analyses would probably be most useful when desiring to analyze a number of cancer antigens at a given time, e.g., to follow an antigen profile during disease progression.

e. In vivo Imaging

The invention also provides in vivo methods of imaging cancer using antibody conjugates. The term "in vivo imaging" refers to any non-invasive method that permits the detection of a labeled antibody, or fragment thereof, that specifically binds to cancer cells located in the body of an animal or human subject.

The imaging methods generally involve administering to an animal or subject an imaging-effective amount of a detectably-labeled cancer-specific antibody or fragment thereof (in a pharmaceutically effective carrier), such as a HOJ-1 antibody, and then detecting the binding of the labeled antibody to the cancerous tissue. The detectable label is preferably a spin-labeled molecule or a radioactive isotope that is detectable by non-invasive methods.

An "imaging effective amount" is an amount of a detectably-labeled antibody, or fragment thereof, that when administered is sufficient to enable later detection of binding of the antibody or fragment to cancer tissue. The effective amount of the antibody-marker conjugate is allowed sufficient time to come into contact with reactive antigens that be present within the tissues of the patient, and the patient is then exposed to a detection device to identify the detectable marker.

Antibody conjugates or constructs for imaging thus have the ability to provide an image of the tumor, for example, through magnetic resonance imaging, x-ray imaging, computerized emission tomography and the like. Elements particularly useful in Magnetic Resonance Imaging ("MRI") include the nuclear magnetic spin-resonance isotopes $^{157}$Gd, $^{55}$Mn, $^{162}$Dy, $^{52}$Cr, and $^{56}$Fe, with gadolinium often being preferred. Radioactive substances, such as technicium$^{96m}$ or indium that may be detected using a gamma scintillation camera or detector, also may be used. Further examples of metallic ions suitable for use in this invention are $^{123}$I, $^{131}$I, $^{131}$I, $^{97}$Ru, $^{67}$Cu, $^{67}$Ga, $^{125}$I, $^{68}$Ga, $^{72}$As, $^{89}$Zr, and $^{201}$Tl.

A factor to consider in selecting a radionuclide for in vivo diagnosis is that the half-life of a nuclide be long enough so that it is still detectable at the time of maximum uptake by the target, but short enough so that deleterious radiation upon the host, as well as background, is minimized. Ideally, a radionuclide used for in vivo imaging will lack a particulate emission, but produce a large number of photons in a 140–2000 keV range, which may be readily detected by conventional gamma cameras.

A radionuclide may be bound to an antibody either directly or indirectly by using an intermediary functional group. Intermediary functional groups which are often used to bind radioisotopes which exist as metallic ions to antibody are diethylenetriaminepentaacetic acid (DTPA) and ethylene diaminetetracetic acid (EDTA).

Administration of the labeled antibody may be local or systemic and accomplished intravenously, intra-arterially, via the spinal fluid or the like. Administration also may be intradermal or intracavitary, depending upon the body site under examination. After a sufficient time has lapsed for the labeled antibody, or fragment to bind to the diseased tissue, in this case cancer tissue, for example 30 min to 48 h, the area of the subject under investigation is then examined by the imaging technique. MRI, SPECT, planar scintillation imaging and other emerging imaging techniques may all be used.

The distribution of the bound radioactive isotope and its increase or decrease with time is monitored and recorded. By comparing the results with data obtained from studies of clinically normal individuals, the presence and extent of the diseased tissue can be determined.

The exact imaging protocol will necessarily vary depending upon factors specific to the patient, and depending upon the body site under examination, method of administration, type of label used and the like. The determination of specific procedures is, however, routine to the skilled artisan. Although dosages for imaging embodiments are dependent upon the age and weight of patient, a one time dose of about 0.1 to about 20 mg, more preferably, about 1.0 to about 2.0 mg of antibody-conjugate per patient is contemplated to be useful.

f. Immunodetection Kits

In further embodiments, the invention provides immunological kits for use in detecting cancer cells, e.g., in biological samples. Such kits will generally comprise one or more antibodies that have immunospecificity for proteins or peptides, such as HOJ-1, encoded by the nucleic acid markers of cancer identified in the present invention.

As the HOJ-1 and related cancer marker proteins or peptides may be employed to detect antibodies and the anti-marker antibodies may be employed to detect cancer proteins or peptides, either or both of such components may be provided in the kit. The immunodetection kits will thus comprise, in suitable container means, a HOJ-1 or related cancer marker protein or peptide, or a first antibody that binds to such a cancer marker protein or peptide, and an immunodetection reagent.

Kits comprising antibodies, such as anti-HOJ-1 antibodies, will be preferred in many cases. In more preferred embodiments, it is contemplated that the antibodies will be those that bind to the HOJ-1 epitopes. Monoclonal antibodies are readily prepared and will often be preferred. Where cancer marker proteins or peptides are provided, it is generally preferred that they be highly purified.

In certain embodiments, the cancer protein or peptide, or the first antibody that binds to the marker protein or peptide, such as an anti-HOJ-1 antibody, may be bound to a solid support, such as a column matrix or well of a microtitre plate.

The immunodetection reagents of the kit may take any one of a variety of forms, including those detectable labels that are associated with, or linked to, the given antibody or antigen itself. Detectable labels that are associated with or attached to a secondary binding ligand are also contemplated. Exemplary secondary ligands are those secondary antibodies that have binding affinity for the first antibody or antigen.

Further suitable immunodetection reagents for use in the present kits include the two-component reagent that comprises a secondary antibody that has binding affinity for the first antibody or antigen (generally anti-HOJ-1 or HOJ-1), along with a third antibody that has binding affinity for the second antibody, wherein the third antibody is linked to a detectable label.

As noted above in the discussion of antibody conjugates, a number of exemplary labels are known in the art and all such labels may be employed in connection with the present invention. Radiolabels, nuclear magnetic spin-resonance isotopes, fluorescent labels and enzyme tags capable of generating a colored product upon contact with an appropriate substrate are suitable examples.

The kits may contain antibody-label conjugates either in fully conjugated form, in the form of intermediates, or as separate moieties to be conjugated by the user of the kit.

The kits may further comprise a suitably aliquoted composition of the cancer protein or antigen, such as HOJ-1, whether labeled or unlabeled, as may be used to prepare a standard curve for a detection assay.

The kits of the invention, regardless of type, will generally comprise one or more containers into which the biological agents are placed and, preferably, suitable aliquoted. The components of the kits may be packaged either in aqueous media or in lyophilized form.

The immunodetection kits of the invention, although containing at least one novel cancer marker antibody or antigen, as may be based on HOJ-1, also may contain one or more of a variety of other cancer marker antibodies or antigens, if so desired. Such kits could thus provide a panel of cancer markers, as may be better used in testing a variety of patients. By way of example, such additional markers could include, other tumor markers such as PSA, SeLe$^x$, g HCG, as well as p53, cyclin D1, p16, tyrosinase, MAGE, BAGE, PAGE, MUC18, CEA, p27 and βHCG.

The container means of the kits will generally include at least one vial, test tube, flask, bottle, or even syringe or other container means, into which the antibody or antigen may be placed, and preferably, suitably aliquoted. Where a second or third binding ligand or additional component is provided, the kit will also generally contain a second, third or other additional container into which this ligand or component may be placed.

The kits of the present invention will also typically include a means for containing the antibody, antigen, and any other reagent containers in close confinement for commercial sale. Such containers may include injection or blow-molded plastic containers into which the desired vials are retained.

8. Prognostic Applications

HOJ-1 was identified in a variety of cancer cells and cell lines. As such, HOJ-1 and the other related sequences are useful as markers for a cancer phenotype. Evaluation of the expression of HOJ-1, and the other sequences of the invention, in the cancer tissues of a patient will be useful in determining whether that patient's cancer will progress and, therefore, will allow a proper determination of the need for additional therapy to be made.

The expression levels of HOJ-1, and other sequences, will also be useful in monitoring the effectiveness of a treatment regimen. In any event, the methods of the present invention will assist physicians in diagnosing cancer and in determining optimal treatment courses for individuals with tumors of varying malignancy.

As described herein in detail, the amount of a HOJ-1 or related cancer marker present within a biological sample, such as a tissue, blood or serum sample, may be determined by means of a molecular biological assay to determine the level of a nucleic acid that encodes such a polypeptide, or by means of an immunoassay to determine the level of the polypeptide itself.

It is envisioned that in clinical applications, human tissue samples will be screened for the presence of the markers of cancer identified herein. Such samples could consist of needle biopsy cores, surgical resection samples, lymph node tissue, or serum/plasma.

In certain embodiments, nucleic acids would be extracted from these samples and amplified as described above. Some embodiments would utilize kits containing pre-selected primer pairs or hybridization probes. The amplified nucleic acids would be tested for the markers by any of the detection methods described herein or other suitable methods known in the art.

In other embodiments, tissue extracts containing marker proteins would be extracted from a sample and subjected to an immunoassay as described herein. Immunoassays of tissue sections are also possible. Kits containing the antibodies of the invention would be useful.

Another embodiment of the present invention involves application of RT-PCR™ techniques to detect circulating cancer cells in blood (i.e., those that have already metastasized), using probes and primers selected from the nucleic acid sequences disclosed herein, such as from SEQ ID NO:1. Similar techniques have been described in PCT Patent Application No. WO 94/10343, incorporated herein by reference.

In this embodiment, metastatic cancer cells are detected in hematopoietic samples by amplification of cancer-specific nucleic acid sequences, such as HOJ-1 sequences. Samples taken from blood or lymph nodes are treated to purify total cell RNA. The isolated RNA is reverse transcribed using a reverse transcriptase and primers selected to bind under high stringency conditions to a cancer nucleic acid sequence of the invention, as exemplified by the HOJ-1 sequence of SEQ ID NO:1. Following reverse transcription, the resulting cDNAs are amplified using standard PCR™ techniques and a thermostable DNA polymerase and amplified sequences are detected.

The presence of cancer-marker nucleic acids, such as HOJ-1, in blood or lymph node samples is indicative of a patient with metastatic cancer, i.e., indicative of a poor prognosis.

In terms of analyzing tissue samples, irrespective of the manner in which the level of a given cancer marker, such as HOJ-1, is determined, the prognostic evaluation will generally require the amount of the marker in the tissue sample to be compared to the amount in normal cells, in other patients and/or amounts at an earlier stage of treatment of the same patient. Comparing the varying levels of a given marker will allow the characteristics of the particular cancer to be more precisely defined.

Thus, the levels of selected marker detected, such as HOJ-1, would be compared with statistically valid groups of metastatic, non-metastatic malignant, benign or normal tissue samples; and/or with earlier marker levels in the same patient. The diagnosis and prognosis of the individual patient would be determined by comparison with such groups.

Where the presence of a cancer marker correlates with cancer progression, then the clinical detection of such a marker, or an increase in the levels of such a marker, in comparison to the levels in a corresponding biological sample from a normal or even more healthy subject, is indicative of a patient with advancing cancer.

Likewise, where the absence of a cancer marker correlates with cancer progression, then the failure to clinically detect such a marker, or a decrease in the levels of such a marker, in comparison to the levels in a corresponding biological sample from a normal or even more healthy subject, would also be indicative of a patient with advancing cancer. An example is the loss, decreasing levels or mutation of a tumor suppressor.

Those of skill in the art are very familiar with differentiating between the significant expression of a biomarker, such as HOJ-1 cancer marker, which represents a positive identification, and the low level or background expression of a biomarker. Indeed, background expression levels are often used to form a "cut-off" above which increased levels are scored as significant or positive. Significant expression may be represented by high levels of nucleic acids or antigens in tissues or within body fluids, or alternatively, by a high proportion of cells from within a tissue that each give a positive signal.

If desired, the cancer screening methods of the present invention may be readily combined with other methods in order to provide an even more reliable indication of prognosis. Various markers of cancer have been proposed to be correlated with metastasis and malignancy. They are generally classified as cytological, protein or nucleic acid markers. Any one or more of such methods may thus be combined with those of this invention in order to provide a multi-marker prognostic test.

Cytological markers include such things as "nuclear roundedness" (Diamond et al., 1982) and cell ploidy. Protein markers include prostate specific antigen (PSA) and CA125. Nucleic acid markers have included amplification of Her2/neu, point mutations in the p53 or Ras genes, and changes in the sizes of triplet repeat segments of particular chromosomes.

All of the above markers exhibit certain drawbacks, associated with false positives and false negatives. A false positive result occurs when an individual without malignant cancer exhibits the presence of a "cancer marker". For example, elevated serum PSA has been associated with prostate carcinoma. However, it also occurs in some individuals with non-malignant, benign hyperplasia of the prostate.

A false negative result occurs when an individual actually has cancer, but the test fails to show the presence of a specific marker. The incidence of false negatives varies for each marker, and frequently also by tissue type. For example, Ras point mutations have been reported to range from a high of 75% in pancreatic cancer to a low of zero percent in some gynecological cancers.

Additional problems arise when a marker is present only within the transformed cell itself. Ras point mutations can only be detected within the mutant cell. This means that, in order to detect a malignant tumor, one must take a sample of the tumor itself, or its metastatic cells. Since the object of cancer detection is to identify and treat tumors before they metastasize, essentially one must first identify and sample a tumor before the presence of the cancer marker can be detected.

Finally, specific problems occur with markers that are present in normal cells but absent in cancer cells. Most tumor samples will contain mixed populations of both normal and transformed cells. If one is searching for a marker that is present in normal cells, but occurs at reduced levels in transformed cells, the "background" signal from the normal cells in the sample may mask the presence of transformed cells.

Preferred cancer markers are those that are present in malignant cancers, and either missing or else expressed at significantly lower levels in benign tumors and normal cells. As any single marker would typically be present only in some proportion of malignant cancers, it is desirable to have a number of such markers for each cancer type.

The present invention addresses the need for cancer markers by identifying a new nucleic acid marker that is expressed at higher levels in malignant carcinoma than in normal tissue. In preferred embodiments, this invention provides a cancer marker, termed HOJ-1, that is indicative of cancer progression and metastatic potential. This represents a significant advance. However, combination of the present techniques with one or more other diagnostic or prognostic techniques or markers is certainly contemplated. In that many cancers are multifactorial, the use of more than one method or marker is often highly desirable.

9. Cancer Treatment
a. Antisense Therapy

As discussed above, HOJ-1 has been shown herein to possess sequence homology with HRC-1, a transcriptional factor or oncogene (Weitzel et al., 1992, Weitzel and Patel 1994). These observations suggest that HOJ-1 also is likely an oncogene. However, HRC1 is located on chromosome 11 p whereas HOJ-1 is located on chromosome 12 p. As such, one therapeutic modality of the invention is the use of an effective amount of one or more anti-sense nucleic acid sequences that bind to and inhibit one or more of the nucleic acid cancer markers disclosed herein, such as HOJ-1. Such techniques are effective in inhibiting expression of the protein products of the HOJ-1 and related cancer marker genes.

Antisense molecules of this invention will generally be designed to inhibit the transcription, translation or both, of a given cancer gene. They may be used both in vitro and in vivo, for example, to inhibit gene expression in pre-clinical testing and within host animals, including human subjects.

In pre-clinical testing, transfection of cancer cells with antisense HOJ-1, e.g., expressed by a CMV promoter, will be useful. The soft agar colony formation, in vivo tumorigenicity and metastatic potential of the transfected cells will then be determined. Once antisense expression has been shown to reduce the tumorigenicity and/or metastatic potential, clinical treatment can be pursued.

Antisense constructs are oligo- or polynucleotides comprising complementary nucleotides to the control regions or coding segments of a DNA molecule, such as a gene or cDNA. Such constructs may include antisense versions of both the promoter and other control regions, exons, introns and exon:intron bouridaries of a gene, such as HOJ-1. Antisense molecules inhibit the transcription, translation or both, of a given gene or construct, to a degree effective to reduce or diminish the levels of the resultant protein product.

Nucleic acid sequences comprising "antisense or complementary nucleotides" are those which are capable of basepairing according to the standard Watson-Crick complementarity rules. That is, that the larger purines will base pair with the smaller pyrimidines to form only combinations of Guanine paired with Cytosine (G:C) and Adenine paired with either Thymine (A:T), in the case of DNA, or Adenine paired with Uracil (A:U) in the case of RNA.

A particular example of an antisense sequence of the present invention is a HOJ-1 antisense sequence of SEQ ID NO:1 or an antisense fragment thereof.

Antisense RNA constructs, or DNA encoding such antisense RNAs, may be employed to inhibit cancer gene transcription or translation or both within a host cell or animal, including a human subject. For example, U.S. Pat. No. 4,740,463, incorporated herein by reference, describes in general methods for antagonizing the effects of an oncogene using oppositely transcribed oncogene DNA segments. Although not describing cancer marker genes, such as HOJ-1, the methodology generally disclosed in U.S. Pat. No. 4,740,463 may be used in connection with the genes of the present invention.

PCT Patent Application WO 95/10265, incorporated herein by reference, also describes methods useful for the delivery of antisense oligos, which methods utilize a surface active non-ionic copolymer (a block copolymer). Such delivery methods also may be used in the context of the present invention. If desired, the anti-HOJ-1 constructs, for example, may be linked to a cell-specific binding agent for enhanced delivery, as described in PCT Patent Application WO 94/23050.

In certain embodiments, one may wish to employ antisense constructs that include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

Those of skill in the art are well aware of how to apply sense and antisense gene delivery to in vivo and ex vivo situations. Such delivery can be via DNA sequence alone, plasmids vectors or through peptide nucleic acids (PNAs). DNA sequences alone incorporated in liposomes can be used to deliver sense and antisense DNA (Dzau et al., 1996) PNAs can be used to replace nucleic acid sequences in a sense or antisense orientation. These can be delivered to cell to block expression of mRNA of HOJ-1. Delivery of the above sequences can be directly to the target site, a nearby region or systemically in human. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

Also, U.S. Pat. No. 5,138,045 and European Patent Application EP 431,523, each incorporated herein by reference, describe oligos having improved cellular uptake and nuclease resistance. Antisense constructs directed to cancer genes such as HOJ-1 and modified to include nitrogenous moieties, such as polyamines and hydrazines, linked to the sugar residues, as described in U.S. Pat. No. 5,138,045, are contemplated for use with this invention. Oligos modified according to EP 431,523 are also contemplated for use.

b. Immunotherapy

Immunotherapy is one many ways in which HOJ-1, and the other cancer markers of the invention, may be used in therapeutic intervention in cancer disease. Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In certain contexts, it will first be confirmed that the cancer markers of the invention, such as HOJ-1, are presented on the cell surface in the context of MHC class I. Specific epitopes that are so presented will also be determined. The specific in vitro lysis by primed cytolytic T lymphocytes (CTLs) will then de demonstrated.

In certain other contexts, it also may be desirable to confirm that cancer patients have CTLs that are reactive against the cancer markers of the invention, such as HOJ-1, when the antigens are presented on autologous cancer cells.

In certain treatment embodiments of the invention, cancer may be treated by the administration of an effective amount of one or more antibodies that specifically bind to one or more of the proteins or peptides encoded by the cancer markers of the present invention. Administration of anti-HOJ-1 antibodies is currently preferred. These types of therapy are akin to "passive immunity".

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow. All such techniques can be used in this invention. Humanized or human monoclonal antibodies can also be employed in passive immunotherapy.

In other treatment embodiments, cancer patients are treated by the administration of an effective amount of one or more cancer marker antigens, such as HOJ-1. These therapies are linked to "active immunity".

In active immunotherapy, purified antigens, recombinant cells expressing such antigens, and irradiated autologous or allogeneic tumor cell compositions expressing such antigens may be used. Administration may be combined with general adjuvants, such as BCG.

Therapies for melanoma are being pursued using melanoma antigens, such as the MAGE and GAGE families, as targets for immunotherapy. Portions of melanoma antigens are being used to "immunize" patients with the aim of stimulating their CTLs to react against the tumor. The present invention contemplates an analogous use for, e.g., HOJ-1. HOJ-1 or portions thereof are therefore useful as an immune stimulants to increase the activity of the patient's immune system (specifically the CTLs) against cancer. Many other markers exist and any of these may be suitable for targeting in the context of the present invention. Common tumor markers include carcinoembryonic antigen (CEA), prostate specific antigen (PSA), tyrosinase, Ras, HMFG, Sialyl Lewis Antigens, estrogen receptor, laminin receptor, erb B and MAGE-1 and MAGE-3, among others well known to those of skill in the art.

Effective T cell responses can also be mounted without MHC expression, e.g., in MHC class II negative lymphoma. NK cells also target cells that lack MHC. Recombinant HOJ-1 protein or a chimeric HOJ-1-helper molecule plus adjuvant could be used to activate and anti-HOJ-1 response. Given that HOJ-1, for example, is not expressed in normal tissues except for testes and placenta, and as the testes is an immunologically protected site, the possibility of side toxicity or autoimmunity is contemplated to be minimal during such immunotherapy.

Also, autologous cells, such as macrophages and dendritic cells, may be pulsed with a cancer marker peptide of the invention, such as HOJ-1 or peptide thereof, and then administered to a cancer patient. Similarly, autologous cells may be adapted to recombinantly express a cancer marker peptide, such as HOJ-1, before re-administration to a patient. Any recombinant expression vector may be so used, such as a viral vector.

c. DNA Vaccination

Another means, contemplated herein, for generating a therapeutic response in an animal includes administering to the animal, or human subject, a pharmaceutically acceptable composition comprising an immunologically effective amount of a nucleic acid composition of the invention.

The stimulation of specific antibodies and CTL responses upon administering to an animal a nucleic molecule is now well known in the art, as evidenced by articles such as Tang et al. (1992); Cox et al. (1993;) Fynan et al. (1993); Ulmer et al. (1993); Wang et al. (1993); Gal et. al. (1993) and Whitton et al. (1993); each incorporated herein by reference. This technology is often referred to as genetic immunization DNA vaccination (Cohen, 1993).

Cancer marker DNA segments, such as HOJ-1, could be used in virtually any form, including naked DNA and plasmid DNA, and may be administered to the animal or human patient in a variety of ways, including parenteral, oral, mucosal and gene-gun inoculations, as described, for example, by Fynan et al. (1993).

d. Inhibitors

The invention even further comprises the therapeutic treatment of cancer by the administration of an effective dose of one or more inhibitors of HOJ-1, or inhibitors of any one or more of the other proteins encoded by the marker genes of the invention.

Once one or more biological functions of the HOJ-1 cancer marker protein of the invention have been identified, inhibitors may be designed and constructed to interfere with the function of the protein and thus to treat cancer.

The identification of protein function can be extrapolated, in certain cases, from the primary sequence data, provided that sequence homology exists between the initially unknown protein and a protein of similar sequence and known function. Proteins tend to occur in large families of relatively similar sequence and function. For example, a number of the serine proteases, like trypsin and chymotrypsin, have extensive sequence homologies and relatively similar three-dimensional structures. Other general categories of homologous proteins include different classes of transcriptional factors, membrane receptor proteins, tyrosine kinases, GTP-binding proteins, etc.

The amino acid sequences encoded by the cancer marker nucleic acids of the present invention can be cross-checked for sequence homologies versus the protein sequence database of the National Biomedical Research Fund. Homology searches are standard techniques for the skilled practitioner. The identification of a cancer marker as a defined homologue, say of a receptor, would allow inhibitors to be either identified or designed.

In the receptor example, say the cancer marker was a growth factor receptor, or mutant thereof, that transmitted inappropriate growth or proliferation signals to the cell. Various inhibitory ligands, or antagonists, may already be available from studies of other related receptors. Inhibitors and antagonists could also be designed by altering natural ligands or by modeling.

Three-dimensional structures can also be inferred from the primary sequence data of the encoded proteins. Again, if homologies exist between the encoded amino acid sequences and other proteins of known structure, then a model for the structure of the encoded protein can be designed, based upon the structure of the known protein. Once a three-dimensional model is available, inhibitors can be designed by standard computer modeling techniques (Sun and Cohen, 1993, herein incorporated by reference).

e. Combinations

One of the major challenges in oncology today is the effective treatment of a given tumor. Such tumors are often resistant to traditional therapies. Thus, a great deal of effort is being directed at finding efficous treatment of cancer. One way of achieving this is by combining the traditional therapies discussed above. In the context of the present invention, it is contemplated that therapies directed against HOJ-1 could be used in conjunction with chemo- or radio- and indeed gene therapeutic intervention. It also may prove effective to combine HOJ-1 targeted therapy with antisense or immunotherapies directed at other tumor marker, as described above.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with a HOJ-1 targeted therapy and at least one other agent. These compositions would be provided in a combined amount effective to kill or inhibit proliferation of the cell. This process may involve contacting the cells with the HOJ-1 based therapy and the agent(s) or factor(s) at the same time. This may be achieved by contacting the cell with a single composition or pharmacological formulation that includes both agents, or by contacting the cell with two distinct compositions or formulations, at the same time, wherein one composition includes the HOJ-1 based therapy and the other includes the agent.

Alternatively, the HOJ-1 based treatment may precede or follow the other agent treatment by intervals ranging from min to wk. In embodiments where the other agent and HOJ-1 based therapy are applied separately to the cell, one would generally ensure that a significant period of time did not expire between the time of each delivery, such that the agent and HOJ-1 based treatment would still be able to exert an advantageously combined effect on the cell. In such instances, it is contemplated that one would contact the cell with both modalities within about 12–24 h of each other and, more preferably, within about 6–12 h of each other, with a delay time of only about 12 h being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either HOJ-1 based treatment or the other agent will be desired. Various combinations may be employed, where HOJ-1 based treatment is "A" and the other agent is "B", as exemplified below:

A/B/A B/A/B B/B/A A/A/B B/A/A A/B/B B/B/B/A B/B/ A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as, y-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. Further, therapy may be directed at any of the other tumor antigens listed herein above.

In treating cancer according to the invention, one would contact the tumor cells with an agent in addition to the HOJ-1 based treatment. This may be achieved by irradiating the localized tumor site with radiation such as X-rays, UV-light, y-rays or even microwaves. Alternatively, the tumor cells may be contacted with the agent by administering to the subject a therapeutically effective amount of a pharmaceutical composition comprising a compound such as, cisplatin (CDDP), carboplatin, procarbazine, mechlorethamine, cyclophosphamide, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate. The agent may be prepared and used as a combined therapeutic composition, or kit, by combining it with the HOJ-1 based treatment, as described above.

Agents that directly cross-link nucleic acids, specifically DNA, are envisaged to facilitate DNA damage leading to a useful, antineoplastic combination with HOJ-1 based treatment. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as y-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It is proposed that the regional delivery of HOJ-1 based treatment to patients with HOJ-1-linked cancers will be a very efficient method for delivering a therapeutically effective gene to counteract the clinical disease. Similarly, the chemo- or radiotherapy may be directed to a particular, affected region of the subjects body. Alternatively, systemic delivery of HOJ-1 based treatment and/or the agent may be appropriate in certain circumstances, for example, where extensive metastasis has occurred.

In addition to combining HOJ-1 based treatment with chemo- and radiotherapies, it also is contemplated that combination with gene therapies will be advantageous. For example, targeting of HOJ-1 based treatment and p53 or p16 mutations at the same time may produce an improved anti-cancer treatment. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf, erb, src, fins, jun, trk, ret, gsp, hst, bcl and abl.

It also should be pointed out that any of the foregoing therapies may prove useful by themselves in treating a cancer. In this regard, reference to chemotherapeutics and non-HOJ-1 based treatment in combination should also be read as a contemplation that these approaches may be employed separately.

The upregulation of cancer marker antigens, such as HOJ-1, by demethylating agents such as DAC also is contemplated. In addition, the use of cytokines, such as GM-CSF, along with any of the treatments described above is envisioned for use in further increasing the effectiveness of the therapy.

Of course, where a tumor is being treated, any one or more of the classical anti-cancer strategies above also may be combined with surgery. The tumor may be treated before, after and during resection. The treatment may comprise a single application of therapy or multiple applications as the need arises.

10. Screening for Candidate Substances

In certain embodiments, the present invention concerns a method for screening for candidate substances with anti-tumor activity and for screening for modulators of HOJ-1 activity. It is contemplated that this screening technique will prove useful in the general identification of compounds that will inhibit, reduce, decrease or otherwise abrogate tumor growth, size or metastases.

Such methods of the invention may use HOJ-1 proteins, HOJ-1 nucleic acids or anti-HOJ-1 antibodies and the like as reagents in the screening of small molecule and peptide libraries to identify modulators of HOJ-1 expression. Within one example, a modulator screening assay is performed on cells expressing HOJ-1 proteins. These cells are exposed to a test substance under suitable conditions, and for a time sufficient, to permit the agent to affect the expression of HOJ-1 proteins. HOJ-1 expression is detected, for example, by incubating cells or cell lysates with a HOJ-1 protein-specific antibody, which antibody may be labeled directly or may be detected secondarily, e.g., using a labeled specific antibody. The test reaction is compared to a control reaction which lacks the test sample. To complete the screening assay, the presence and/or amount of complexes formed between the HOJ-1 protein and the anti-HOJ-1 antibody is detected in the test sample (e.g. by determining the presence or amount of label bound directly to the antibody or to a secondary antibody directed against the primary antibody).

In an alternative embodiment, it will be possible to screen for a candidate substance that is capable of modulating HOJ-1 activity. Preferably, HOJ-1 activity is measured in terms of tumorigenicity in a cell, for example, a cancer cell expressing HOJ-1. The HOJ-1 activity is monitored in the presence and absence of a candidate substance. Such an activity also may comprise MAGE-binding capacity of the HOJ-1 protein. Thus, to identify a candidate substance as modulating HOJ-1 activity, one will compare one or more HOJ-1 protein activities in the presence of the candidate substance with the HOJ-1 activity in the absence of the candidate substance.

In defined embodiments, the candidate substance may be a chemotherapeutic agent, a radiotherapeutic agent or selected from a small molecule library. Generally the candidate substance is added in the form of a purified agent. However, it also is contemplated that candidate substances useful within the present invention may include substances present throughout the handling of test sample components, for example host cell factors that are present in a cell lysate used for generating the test sample. Such endogenous factors may be segregated between the test and control samples for example by using different cell types for preparing lysates, where the cell type used for preparing the test sample expresses a putative test substance that is not expressed by the cell type used in preparing the control sample. Useful compounds in this regard may include fragments or parts of naturally-occurring compounds or may be only found as active combinations of known compounds which are otherwise inactive. However, prior to testing of such compounds in humans or animal models, it will possibly be necessary to test a variety of candidates to determine which have potential.

Accordingly, in screening assays to identify pharmaceutical agents which have anti-tumor activity and/or alter the expression of HOJ-1 proteins in for example cancer cells, it is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds.

A candidate substance identified as a substance that decreases HOJ-1 expression can be confirmed as having an anti-tumor activity by correlating the decreases in protein expression and/or activity with decreases in the tumor characteristics of the cancer cell. In these embodiments, the screening assay may measure some other characteristic of a HOJ-1 expressing cancer cell. The characteristic may be selected from the group consisting of, proliferation, metastasis, contact inhibition, soft agar growth, cell cycle regulation, chromosome recombination, tumor formation, tumor progression and tissue invasion. Conversely, where the initial screen is on the basis of anti-tumor activity, specific correlation with HOJ-1 function may be ascertained as a second step.

In these embodiments, the present invention is directed to a method for determining the ability of a candidate substance to exhibit anti-tumor activity, the method including generally the steps of:

(a) providing a cell expressing HOJ-1 polypeptide;

(b) contacting the cell with the candidate substance; and (c) determining the effect of the candidate substance on HOJ-1 expression or cell phenotype.

Determining the effect of the substance involves measuring the expression or characteristic in the absence of the added candidate substance as well. Such candidate screening assays generally involve replicate cultures of the genetically identical cells.

"Effective amounts" are those amounts of a candidate substance effective to reproducibly decrease expression of HOJ-1 in an assay in comparison to levels in untreated cells. An "effective amount" also is defined as an amount that will decrease, reduce, inhibit or otherwise abrogate the growth of a cancer cell.

A significant decreases in HOJ-1 expression and/or activity, are represented by a decrease in HOJ-1 protein expression and/or activity (binding, tumorigenicity) levels of at least about 30%–40%, and most preferably, by decreases of at least about 50%, with higher values of course being possible. Assays that measure protein expression or activity in cells are well known in the art and may be conducted in vitro or in vivo, and have been described elsewhere in the specification.

In particular embodiments, one may measure inhibition of growth of cancer cells, for example, by measuring growth according to the MTT assay. A significant inhibition in growth is represented by decreases of at least about 30%–40% as compared to uninhibited, and most preferably, of at least about 50%, with more significant decreases also being possible. Growth assays as measured by the MTT assay are well known in the art. Assays may be conducted as described by Mosmann et al., 1983; Rubinstein et al., 1990 (incorporated herein by reference).

Quantitative in vitro testing of the anti-tumor agents identified herein is not a requirement of the invention as it is generally envisioned that the agents will often be selected on the basis of their known properties or by structural and/or functional comparison to those agents already demonstrated to be effective. Therefore, the effective amounts will often be those amounts proposed to be safe for administration to animals in another context.

11. Pharmaceuticals

Aqueous compositions of the present invention comprising effective amounts of antibodies, antibody conjugates, inhibitors, antisense constructs, or other compounds of the invention, may be dissolved or dispersed in a pharmaceutically acceptable carrier or medium to form diagnostic and/or therapeutic formulations of the invention.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The active compounds will generally be formulated for parenteral administration, e.g., formulated for injection via the intravenous, intramuscular, sub-cutaneous, intralesional, or even intraperitoneal routes. The preparation of an aqueous composition that contains a cancer marker antibody, conjugate, inhibitor or other agent as an active component or ingredient will be known to those of skill in the art in light of the present disclosure. Typically, such compositions can be prepared as injectibles, either as liquid solutions or suspensions; solid forms suitable for using to prepare solutions or suspensions upon the addition of a liquid prior to injection can also be prepared; and the preparations can also be emulsified.

The pharmaceutical forms suitable for injectible use include sterile aqueous solutions or dispersions; formulations including sesame oil, peanut oil or aqueous propylene glycol; and sterile powders for the extemporaneous preparation of sterile injectible solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Formulations of neutral or salt forms are also provided. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectible compositions can be brought about by the use in the compositions of agents delaying absorption, for example, aluminum monostearate and gelatin.

Sterile injectible solutions are prepared by incorporating the active compounds in the required amount in the appropriate solvent with various of the other ingredients enumerated above, as required, followed by filtered sterilization.

Generally, dispersions are prepared by incorporating the various sterilized active ingredients into a sterile vehicle which contains the basic dispersion medium and the required other ingredients from those enumerated above. In the case of sterile powders for the preparation of sterile injectible solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for local injection also is contemplated. In this regard, the use of DMSO as solvent is preferred as this will result in extremely rapid penetration, delivering high concentrations of the active agents to a small area.

Upon formulation, solutions will be administered in a manner compatible with the dosage formulation and in such amount as is diagnostically or therapeutically effective. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In other embodiments, direct intratumoral injection is contemplated. Alternatively, the tumor may be infused or perfused with the therapeutic compounds using any suitable delivery vehicle. Local or regional administration, with respect to the tumor, also is contemplated. Finally, systemic administration may be performed. Continuous administration also may be applied where appropriate, for example, where a tumor is excised and the tumor bed is treated to eliminate residual, microscopic disease. Delivery via syringe or catherization is also contemplated.

In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated or diagnosed. The person responsible for administration will, in any event, determine the appropriate dose for the individual subject.

12. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods a. Bacterial and Yeast Strains

Manipulations of bacterial strains and of DNAs were by standard methods (Ausubel et al., 1994). *Escherichia coli* subcloning efficiency DH5α and HB 101 competent cells (Gibco/BRL) were used as hosts. Competent dual-reporter yeast strain YRG-2 (Stratagene) were transformed according to manufacturer's instructions.

b. Construction of Bait Plasmid and Two-hybrid Screening

The complete human MAGE-1 cDNA coding for the open reading frame (Van Der Bruggen et al., 1991) was amplified from reverse transcribed RNA isolated from melanoma cell line M12 (Hoon et al., 1995) using primers A58 (5'-GGGAATTCTCTCTTGAGCAGAGG-3')(SEQ ID NO:5) and D1 (5'-GGGTCGACCAAAGCTGCTTCAC-3')(SEQ ID NO:6) which includes EcoRI and SalI cloning sites, excluding the primary ATG of the open reading frame sequence and extending past the TGA stop codon by 57 nucleotides. The 900 base pair amplicon was subcloned into the pGBT9 "bait" vector (Clonetech) and the correct reading frame confirmed by sequencing. For in vivo interaction screening in the yeast two-hybrid system (Chien et al., 1991), 50 µg of a testes cDNA expression "prey" library in pGAD 10 (Clonetech) was cotransformed with 50 µg pGBT9/MAGE-1 fusion plasmid into competent YRG-2 yeast cells. From approximately 100,000 transformations, 103 HIS$^+$, LaeZ$^+$ colonies were selected for further analysis. Plasmid library cDNAs were then prepared from the individual yeast colonies (Robzyk and Kassir, 1992) and separated from the pGBT9/MAGE-1 bait plasmid by LEU2 complementation in *E. coli* HB 101 cells carrying the leuB mutation, and back-transformed into yeast YRG-2 with various control plasmids and the original bait plasmid to ensure specific interaction with the MAGE-1 fusion protein. From this screen, 10 positive MAGE-1 specific interacting clones were identified and dideoxynucleotide sequenced.

c. Protein Sequence Analysis.

BLAST homology searches were performed online via the National Center for Biotechnology Information at the National Institutes of Health, Bethesda, Md. (Altschul et al., 1990). Database programs ScanProsite and Peptide Mass on ExPASy, PSORT, TMpred on ISREC, and TFSEARCH on PAPIA were performed for analysis of the protein sequence.

d. Determination of the 5' cDNA Sequence by RACE.

Based upon the cDNA sequence from the pGAD 10 prey expression plasmid, three nested primers were synthesized complementary to the derived sequence: C28M255 (5'-TGAGGTGCCTAAGTGTCTTTCAGTATCTC-3')(SEQ ID NO:7) C28M179 (5'-GCTAAGGCTATGACAACCTCCTGGC-3')(SEQ ID NO:8) and C28M142 (5'-CAGTGACTCCACAACAATCCTCTGA)(SEQ ID NO:9). One µg M24 melanoma cell line total RNA was reverse transcribed, poly dC tailed according to manufacturer's protocols (Gibco/BRL) and subjected to two rounds of nested PCR™ at 55° C. annealing and 1.5 mM Mg$^{2+}$. The 220 nucleotide amplified product was subcloned and dideoxynucleotide sequenced, yielding an additional 150 nucleotides of mRNA sequence.

e. Genomic-LA PCR™

Based on cloned cDNA sequences, several primer sets were designed 28U (5' CTT AGT CTT CTC CAC TCC GTG TT 3')(SEQ ID NO:12), 607L (5' GAT TAG CTT CTT CAA CTC ATC TGC 3')(SEQ ID NO:13), 67U (5' TGA CCT AAC ACC CTG ATG ACC ACT C 3')(SEQ ID NO:14), 261L (5' TGA GGT GCT AAG TGT CTT TCA GTA TCT CT 3')(SEQ ID NO:15), 124U (5' TGG AAC TTA AAG TAT GGG TGG ATG G 3')(SEQ ID NO:16), 425L (5' CTA AGG GGG AGA CTC TGC CTG TAT 3')SEQ ID NO:17, 267U (5' ACT GAA AGA CAC TTA GCA CCT CAT 3')(SEQ ID NO:18), 432L (5' TTT AGC TAA GGG GGA GAC TCT G 3')(SEQ ID NO:19), 492U (5' GCT CGA ATT CCT GAA AGA AC 3')(SEQ ID NO:20) and 729L (5' CTC TAG ACG GAC AAT TTC CTC T 3') (SEQ ID NO:21). Using these primers, LA (long and accurate) PCR™ (Takara Shuzo, Shiga, Japan) was performed on genomic DNA from the BT-20 human breast cancer cell line to amplify genomic fragments and to compare PCR™ product size between genomic DNA and post-RT cDNA. Primers designed between nucleotides 28 and 607 of the cDNA amplified a longer PCR™ product (>8 kb) than that by RT-PCR™. Primers on the 3' portion of nucleotide 267 of the cDNA did not produce a size difference, indicating the possibility of at least one intron between nucleotides 28 and 266 of the cDNA and the absence of an intron after nucleotide 267. Both primer sets 67U/261L and 124U/425L amplified an 8.5 kb product, indicating that a large intron(s) (>8 kb) is present between nucleotides 123 and 266.

f. FISH for Chromosomal Localization of HOJ-1

A digoxigenin (DIG)-labeled DNA probe was generated for non-isotopic hybridization screening of high density grid filters from the arrayed P1 human genomic DNA library (Genome Systems, St. Louis, Mo.). The PCR™ fragment corresponding to nucleotides 124–448 of HOJ-1 cDNA was labeled by incorporation of digoxigenin-11-dUTP (Boehringer Mannheim, Indianapolis, Ind.) during PCR™ followed by purification with the QIAquick gel extraction kit (Qiagen, Santa Clarita, Calif.) according to the manufacturer's instructions. The P1 filter set represents the entire human genome with individual P1 clones spotted at a very high density on it. Each P1 DNA spot on the filter corresponds to an "address" in the microtiter dishes that contains the P1 library. Individual P1 plasmids contain a genomic insert of 75–100 kb. To avoid false positives, each microtiter dish number was repeated twice.

The filters were hybridized with a DIG-labeled DNA probe (20 ng/ml) overnight at 68° C. in standard hybridization buffer with 1% blocking reagent (Boehringer Mannheim) according to the manufacturer's instructions. The UV-closslinked PCR™ products corresponding to nucleotides 124–448 and 67–289 of the HOJ-1 cDNA were used as positive controls, and a housekeeping gene, porphobilinogen deaminase (PBGD), which has no homology with HOJ-1, was used as a negative control. The detection assay was performed with the colorimetric detection reagents NBT and BCIP (Boehringer Mannheim). There were two positive signals representing one positive clone. After identifying the position of the positive hybridization site, the P1 clone was picked and verified by partial sequencing. To exclude false positives or pseudogene, the oligonucleotide primer 67U (5' TGA CCT AAC ACC CTG ATG ACC ACT C 3')(SEQ ID NO:14), from the sense strand of the HOJ-1 cDNA was used for sequencing since the LA-PCR™ data indicated the presence of an intron(s) between nucleotides 123 and 266 of the cDNA. Sequencing results indicated that it was HOJ-1 and that there is an exon-intron junction between nucleotides 225 and 226 of the HOJ-1 cDNA.

DNA from the positive clone was labeled with DIG-dUTP by nick translation. The labeled probe was combined with sheared human DNA and hybridized to normal metaphase chromosomes derived from PHA stimulated PBLs. Specific hybridization signals were detected by incubating the hybridized slides with fluoresceinated anti-digoxigenin antibodies followed by counterstaining with DAPI. Specific labeling of chromosome 12 on the short arm of a group C chromosome was determined on the basis of size, morphology, and banding pattern. A genomic probe specific for the long arm of chromosome 12 was co-hybridized with the positive clone, which resulted in the specific labeling of both the short arm and long arm of chromosome 12. Measurement of ten specifically labeled chromosome number twelve's demonstrated that the positive clone was located at a distance 41% from the centromere to the telomere of chromosome arm 12 p, an area which corresponds to 12p12.3 (FIG. 6). A total of 80 metaphase cells were analyzed with 67 exhibiting specific labeling.

g. RNA Extraction.

Total cellular RNA was extracted from cell lines using the Ultraspec RNA Isolation System (Biotecx Laboratories, Houston, Tex.). The human cancer cell lines were established at the John Wayne Cancer Institute (Hoon et al., 1995) or were obtained from the American Type Culture Collection (Rockville, Md.) or the Japan Cancer Tissue Bank.

Human cancer tissue specimens were obtained from the John Wayne Cancer Clinic, the Cooperative Human Tissue Network (Case Western Reserve University, Cleveland, Ohio), and the Virginia Commonwealth University (Dr. Randall E. Merchant). Total RNA from tissue specimens was extracted using Tri-Reagent (Molecular Research Center, Inc., Cincinnati, Ohio) and assessed by RT-PCR™. All specimens pathology were verified by a pathologist.

Total RNA also was extracted from PBLs obtained from healthy donor volunteers, as previously described (Kuo et al., 1998). In brief, the isolation of PBLs from ten ml of blood collected in sodium citrate containing tubes was performed, as previously described (Sarantou et al., 1997). When venipuncture was performed, the first several ml of blood were discarded to avoid skin plug contamination.

h. Northern Blot Analysis

Carcinoma cell line total RNA was isolated (Chomczynski and Mackey, 1995) and blotted to positively-charged nylon membrane (Ambion) using NorthernMax reagents (Ambion). A multiple tissue blot of poly(A)$^+$ RNA from normal human tissues was obtained from Clonetech. Both blots were hybridized to random primer labeled probes (Amersham) at 42° C. using NorthernMax hybridization solution (Ambion) and washed according to manufacturer's protocols, then exposed overnight at −80° C. with an intensifying screen.

i. DIG-labeled Northern Blot Analysis.

Northern blot analysis was performed non-isotopically using DIG-labeling. The PCR™ fragment corresponding to nucleotides 124–448 of the HOJ-1 cDNA was random primed DNA labeled with digoxigenin (DIG)-dUTP using DIG-High Prime (Boehringer Mannheim, Indianapolis, Ind.) as a DIG-labeled DNA probe according to the manufacturer's instructions. Human Multiple Tissue Northern (MTN) blots (Clontech) were hybridized with the DIG-labeled DNA probe (20 ng/ml) overnight at 50° C. using the DIG Easy Hyb (Boehringer Mannheim).

The PCR™ fragment corresponding to nucleotides 402–750, added to the SP6 phage RNA polymerase promoter using Lig'nScribe (Ambion, Austin, Tex.), was used as a template for making a DIG-labeled RNA probe using the DIG RNA Labeling Kit (Boehringer Mannheim) according to the manufacturer's instructions. The Multiple Choice Human Northern Blot (OriGene Technologies, Rockville, Md.) was hybridized with the DIG-labeled RNA probe (80 ng/ml) overnight at 60° C. using the DIG Easy Hyb.

Detection was performed using the colorimetric detection reagents nitroblue tetrazolium (NBT) and 5-bromo-4-chloro-3-indolyl phosphate (BCIP) (Boehringer Mannheim) according to the manufacturer's instructions.

j. RT-PCR™

One $\mu$g of total RNA was denatured and hybridized with oligo dT primers. First strand cDNA was synthesized by reverse-transcriptase. An oligonucleotide sequence from the sense strand of the HOJ-1 cDNA (5'-TGACCTAACACCCTGATGACCACTC-3')(SEQ ID NO:14), nucleotides 67–91 and an oligonucleotide sequence from the antisense strand (5'-TGAGGTGCTAAGTGTCTTTCAGTATCTCT-3')(SEQ ID NO:15), nucleotides 261–289 were used as primers for PCR™. PCR™ was performed in a Hybaid thermal cycler (Hybaid, Middlesex, UK) according to the following conditions: 35 cycles of denaturation (94° C. for 60 sec); re-annealing (60° C. for 75 sec); and extension (72° C. for 75 sec). PCR™ products were detected by 2% agarose gel electrophoresis with ethidium bromide (EtBr) staining. The ubiquitously expressed porphobilinogen deaminase (PBGD) gene was used as an mRNA positive control housekeeping gene (20). All RT-PCR™ were performed with equal amount of RNA and assessed for PBGD expression. All assays were repeated at least twice to demonstrate reproduciblity.

k. Southern Blotting.

Specific PCR™ products were verified by Southern blot analysis using the DIG System (Boehringer Mannheim). In brief, after denaturation and neutralization of the PCR™ product run gel, the PCR™ products were blotted onto the membrane using the PosiBlot Pressure Blotter (Stratagene) and crosslinked to the membrane using the Stratalinker UV crosslinker (Stratagene). An oligonucleotide sequence from the sense strand of the HOJ-1 cDNA (5'-CAGGGACCTTGAGTGACTGGCCGGTGCACC-3') (SEQ ID NO:22), nucleotides 93–122, was purified by HPLC and then labeled by 3'tailing using the DIG Oligonucleotide Tailing Kit (Boehringer Mannheim). The membranes were hybridized with the DIG-labeled oligonucleotide probe for 2 hr at 68° C. using the DIG Easy Hyb. Detection was performed with the colorimetric reagents NBT and BCIP. LA (long and accurate) PCR™ (Takara Shuzo, Shiga, Japan) was performed to amplify genomic fragments and to compare PCR™ product size between cDNA fragments and genomic DNA.

l. Recombinant Protein Production and Purification

The 327 nucleotides that encode for the 109 amino acid open reading frame were amplified with PCR™ primers that engineered unique SacI and XhoI sites, and was subsequently subcloned into a modified GST-fusion vector pGEX-1 λT (Pharmacia) (Smith and Johnson, 1988) that contains an in-frame hexa-histidine tag on the C-terminal end (FIG. 1) using primers, 5'-CAAGGAGCTCAATGGAACTTAAAGTATGGG-3'SEQ ID NO:23) and 5'-CTTGCTCGAGGCTAAGGGGGAGACTCTGCC-3' (SEQ ID NO:24). Overnight cultures were diluted 1:100 in LB shaker flasks, and GST-fusion protein was induced with 0.1 mM IPTG at $OD^{600} \approx 0.6$ for 3 h. A crude preparation by glutathione-Sepharose 4B affinity chromatography (Pharmacia) and thrombin digestion (Sigma) was as described by the manufacturer, except for the addition of 5 mM benzamidine (Sigma) and 1 mM ETDA in the lysis and washing buffers. The protein preparation was further purified using a preparative acrylamide gel electrophoresis unit (Biorad, Hercules, Calif.).

m. In vitro Interaction Trap

The 327 nucleotide fragment, containing engineered SacI and XhoI restriction sites, was cloned into pBluescript (Stratagene) downstream from the RNA polymerase promoter. A TnT coupled reticulocyte lysate system (Promega) and 35S methionine (NEN-Dupont) was used to generated 35S labeled recombinant protein. μg GST (control) and 5 μg GST-MAGE-1 bound to 20 μL glutathione Sepharose 4B was prepared and incubated with 35S labeled in-vitro translated HOJ-1 product in 400 μL of bead binding buffer (50 mM $KPO_4$ pH 7.5, 150 mM KCl, 10 mM $MgCl_2$, 10% glycerol, 1% Triton X-100 and 5 mM benzamidine) and clarified E. coli crude lysate (10 mg/mL) (Melcher and Johnson, 1995). After gentle mixing for 2 h at 4° C., the beads were washed 3× in bead binding buffer, and the trapped protein eluted by boiling with 25 μL Laemmli buffer for 5 min. Samples were run on a 15% SDS polyacrylamide gel, dried and autoradiographed.

n. Western Blotting Analysis

5 μg of HOJ-1 was applied on 10–20% SDS-PAGE gel (Novex, San Diego, Calif.) and transferred to the nitrocellulose membrane and the blot was incubated for 1 h with HOJ-1-immunized rabbit sera BAbCO) in series dilutions using a multi-screen apparatus (BioRad) and then incubated with 1:1000 dilution of peroxidase conjugated monoclonal anti-rabbit IgG (g-chain specific) (Sigma), followed by developing with 4-chloro-1-napthol (4CN).

Example 2

Results

Cloning of a Novel Gene HOJ-1.

The inventors report a novel human gene, designated HOJ-1, which was originally isolated from a human testis cDNA library through the identification of reacting proteins with MAGE-1 (Miyashiro et al., submitted). A yeast two-hybrid screening procedure was performed in competent YRG-2 yeast cells using a pGBT9/MAGE-1 fusion plasmid as the bait and a human testis cDNA library in pGAD10 as the prey. One clone, C28, obtained from this screen, was identified and dideoxynucleotide sequenced. Based on the sequence, the inventors synthesized primers (TABLE 3) and applied the 5' RACE. Sequencing of 5' RACE PCR™ products allowed identification of an additional 5' region of the transcript. The compiled sequence (888 bp) of the assembled cDNA, designated HOJ-1, contains an open-reading-frame (ORF) encoding 109 amino acids (SEQ ID NO:1 and SEQ ID NO:2).

A search of the protein database for homologies to HOJ-1 revealed similarity (64% identity) of the predicted amino acid sequence to HRC1, named after HRAS1 Cluster 1, and recently reported as a gene with features of a transcription factor (Weitzel et al., 1992; Weitzel and Patel, 1994) (FIG. 8). The online BLAST homology searches of nucleic acid sequences revealed that HOJ-1 also has limited homology to four other novel human genes but that this homology was less than with HRC1. Nucleotides 767–858 of HOJ-1 show homology to common sequences among three genes (59% identity): a putative human HLA class II associated protein gene PHAPI (Fink et al., 1995), an acidic protein rich in leucines gene APRIL (Mencinger et al., 1998), and a silver-stainable protein gene SSP29 (Zhu et al., 1997). Additionally, nucleotides 767–843 show homology to a huntingtin associated protein HAP1-like protein gene hHLP1 (62% identity) (Li et al., 1995). However, except for HRC1, these other sequence homologies are found within the 3' noncoding region of HOJ-1.

Analysis of the HOJ-1 protein sequence with ScanProsite (protein against PROSITE) showed three protein kinase C phosphorylation sites, three casein kinase II phosphorylation sites, a tyrosine kinase phosphorylation site, and an N-myristoylation site. The PSORT (prediction of protein localization site) and TMpred (prediction of transmembrane regions and orientation) programs revealed that HOJ-1 is probably located in the cytoplasm and is not a transmembrane protein. The TFSEARCH (DNA transcription factor binding site prediction) resulted in no TFMATRIX entry hits for HOJ-1.

TABLE 3

Primer sequences for HOJ-1

| Primer designation | Primer Sequence | Sequence identifier |
|---|---|---|
| 4U: | 5' TTG GTA ACT GAC TGA CTA CAC AGA 3' | SEQ ID NO: 10 |
| 310L: | 5' TAC TGC CCC CAT TTG TTT A 3' | SEQ ID NO: 11 |
| 28U: | 5' CTT AGT CTT CTC CAC TCC GTG TT 3' | SEQ ID NO: 12 |
| 607L: | 5' GAT TAG CTT CTT CAA CTC ATC TGC 3' | SEQ ID NO: 13 |
| p31 (67U)* | 5' TGA CCT AAC ACC CTG ATG ACC ACT C 3' | SEQ ID NO: 14 |
| M255 (261L)* | 5' TGA GGT GCT AAG TGT CTT TCA GTA TCT CT 3' | SEQ ID NO: 15 |
| 123U (124U) | 5' TGG AAC TTA AAG TAT GGG TGG ATG G 3' | SEQ ID NO: 16 |
| 424L (425L) | 5' CTA AGG GGG AGA CTC TGC CTG TAT 3' | SEQ ID NO: 17 |
| 267U | 5' ACT GAA AGA CAC TTA GCA CCT CAT 3' | SEQ ID NO: 18 |
| 432L | 5' TTT AGC TAA GGG GGA GAC TCT G 3' | SEQ ID NO: 19 |
| 402U: | 5' GCT CGA ATT CCT GAA AGA AC 3' | SEQ ID NO: 20 |
| 729L | 5' CTC TAG ACG GAC AAT TTC CTC T 3' | SEQ ID NO: 21 |

*for PCR™ of C28

Northern Blot Analysis.

Figure 4A:
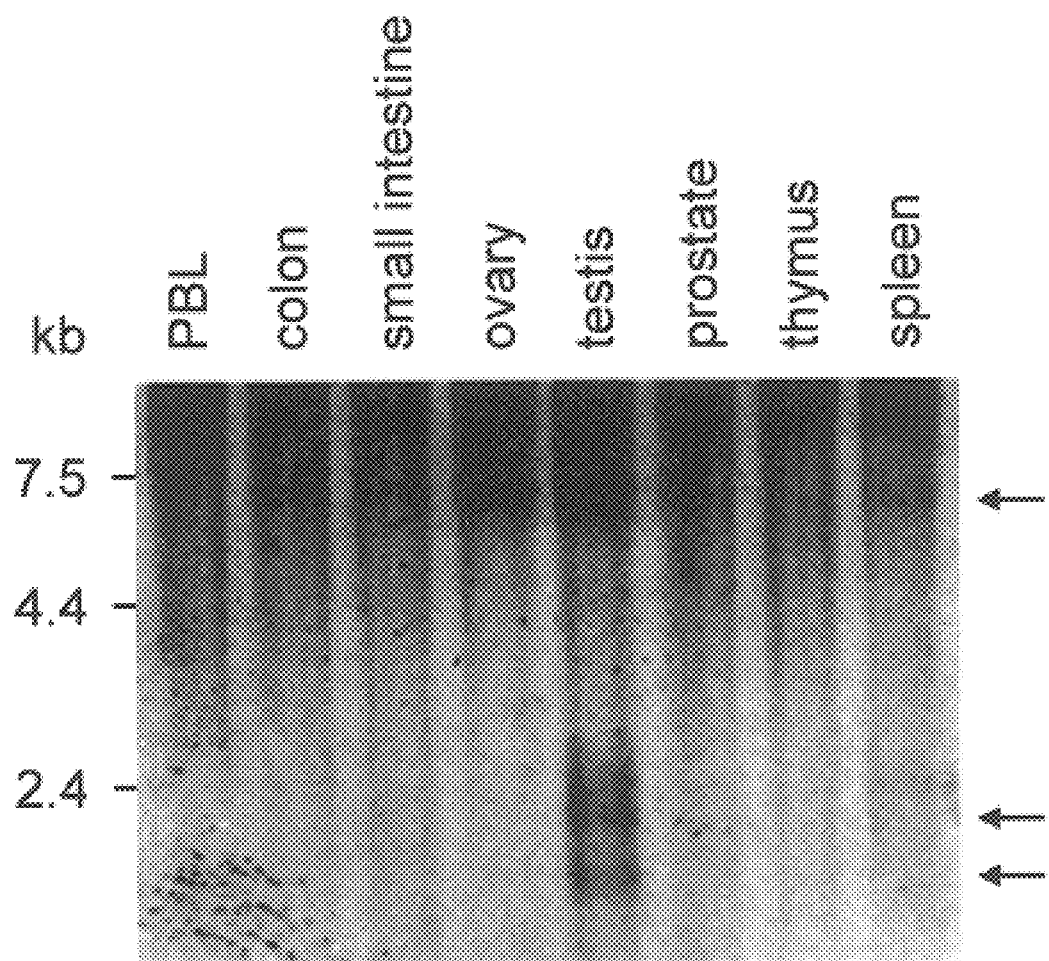
FIG. 4A and FIG. 4B show Northern blot analysis of HOJ-1 in multiple human tissues and cell lines, respectively.

Using a DIG-labeled DNA probe, HOJ124D, corresponding to nucleotide 124–448 of HOJ-1, Northern blot analysis of human mRNA from various normal tissues identified a mRNA of approximately 6.8 kb (FIG. 4A). Normal tissue mRNA, analyzed using the HOJ124D probe, included PBL, colon, small intestine, ovary, testis, prostate, thymus, and spleen. The 6.8 kb mRNA was expressed in all the normal human tissues analyzed, except for PBL (FIG. 4A, TABLE 2). Using a pre-blotted membrane containing an equal amount of mRNA on each lane, the expression level of the 6.8 kb mRNA varied among the tissues assessed. In addition to the 6.8 kb product, testis expressed two other smaller transcription products of approximately 2.4 kb and 1.8 kb in size. All three transcripts in testis were expressed relatively at the same level.

To further verify the findings of HOJ-1 mRNA transcripts in various tissues, a DIG-labeled RNA probe, HOJ402R, for a different region (nucleotides 402–750) of HOJ-1 was also developed. Based on the BLAST homology search, no protein was found to be homologous to this region of HOJ-1. Northern blot analysis using the HOJ402R probe was performed on a membrane blotted with human mRNA from various normal tissues that included lung, small intestine, muscle, stomach, testis, and placenta. The results confirmed the previous findings; only testis expressed all three transcripts and the other tissues expressed only the 6.8 kb product (data not shown).

Figure 4B:
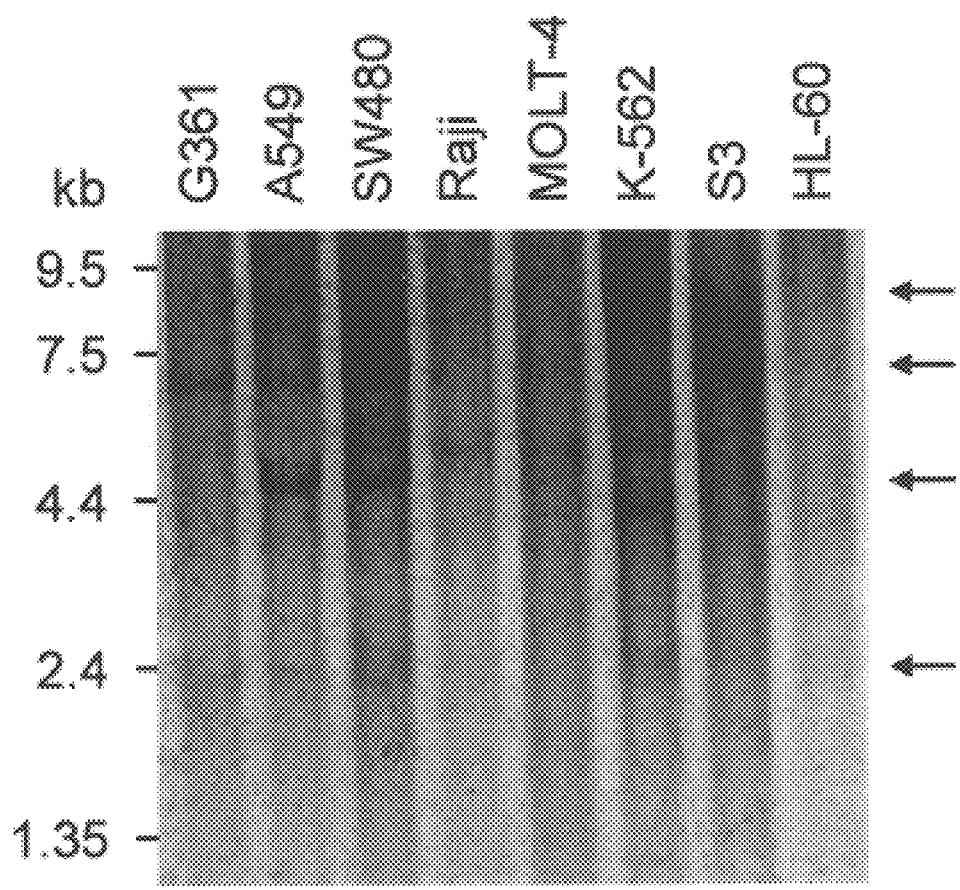

Expression of HOJ-1 was assessed by Northern blotting in eight human cancer cell lines, including melanoma, lung, colorectal, lymphoma, leukemia, and an HeLa cell line. Northern blot analysis showed that these cancer cell lines expressed not only the transcripts detected in normal tissues, but also additional mRNA isoforms (FIG. 4B, TABLE 2). The 6.8 kb product detected in the normal human tissues was also present in 5 of 8 cancer cell lines tested. The 2.4 kb transcript present in testis was detected in 5 of 8 cancer cell lines. The relative abundance of the mRNA isoforms in cancer cell lines was significantly different from the testis pattern of transcripts. The level of the 2.4 kb transcript was reduced in intensity, whereas it is not in testis. At the level of sensitivity of Northern analysis, the 1.8 kb transcript could not be detected clearly in the cancer cell lines tested. Various transcripts ranging from 2.4 to 9.3 kb were also detected. Transcripts of approximately 9.3 kb and/or 4.9 kb, which were not detected on normal tissues, were detected in the chronic myelogenous leukemia cell line K-562, the lung carcinoma cell line A549, and the colorectal adenocarcinoma cell line SW480. The membrane used contained an equal amount of mRNA on each lane, indicating that the expression level of each mRNA product varied among the cancer cell lines assessed. Finding the significance of the different sized transcripts will require detailed molecular characterization of the individual HOJ-1 mRNA isoforms in the cancer cell lines in future studies. Northern blot analysis are shown in FIG. 4A (human tissue) and FIG. 4B (cell lines). These data are summarized in Table 2 below.

TABLE 2

Northern blot analysis of HOJ-1 in human tissue and cancer cell lines. G361 (melanoma); A549 (lung carcinoma); SW480 (colorectal adenocarcinoma); Raji (Burkitt's lymphoma); MOLT-4 (lymphoblastic leukemia); K-562 (chronic mylogenous leukemia); S3 (HeLa cells); HL-60 (promyelocytic leukemia).

| Normal Tissue: | | | | | | | | |
|---|---|---|---|---|---|---|---|---|
| kb | PBL | colon | small intestine | ovary | testis | prostate | thymus | spleen |
| 6.8 | − | + | + | + | + | + | + | + |
| 2.8 | − | − | − | − | + | − | − | − |
| 1.8 | − | − | − | − | + | − | − | − |

| Cell lines: | | | | | | | | |
|---|---|---|---|---|---|---|---|---|
| kb | G361 | A549 | SW480 | Raji | MOLT-4 | K-562 | S3 | HL-60 |
| 9.3 | − | + | − | − | − | + | − | − |
| 6.8 | + | + | + | − | − | − | + | + |
| 6.3 | − | − | − | − | − | + | − | − |
| 5.5 | − | − | + | + | + | + | − | − |
| 5.2 | − | + | − | − | − | − | − | − |
| 4.9 | − | + | + | − | − | − | − | − |
| 4.4 | − | − | − | − | ? | + | − | − |
| 2.4 | + | + | + | ? | ? | + | ? | − |
| 1.8 | − | − | ? | − | − | ? | − | − |
| 1.2 | − | − | − | − | − | ? | − | − |

RT-PCR™ Analysis.

The expression of HOJ-1 was also assessed by RT-PCR™ using specific designed primers for HOJ-1 (TABLE 3). By the BLAST homology search, the primers did not have any homology to other sequences including HRC1. Using the same primers, LA-PCR™ showed that PCR™ products from genomic DNA are much longer (>8 kb) than that from RT-PCR™ (to be published; Miyashiro et al.). This indicated that there is at least one intron between the primers used for PCR™ and that the positive bands detected in the cell lines by RT-PCR™ were not products amplified from contamination of genomic DNA. FIG. 5B shows a schematic of the results of PCR™ analysis.

Figure 5A:
FIG. 5A and FIG. 5B FIG. 5A shows the results of PCR™ analysis of HOJ-1 on human cell lines and normal peripheral blood leukocytes (PBL) from different sources. A 223 base pair HOJ-1 product was detected.
Figure 5B:
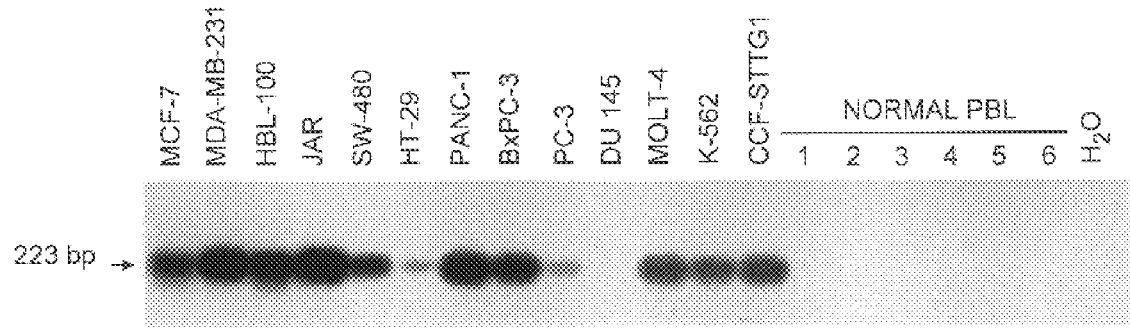

PBL obtained from healthy donors did not express HOJ-1 (FIG. 5A). Using RT-PCR, majority of the human cancer cell lines, including breast, placenta, gastrointestinal, prostate, leukemia, astrocytoma, and melanoma, were found to express a 223 base pair HOJ-1 product (FIG. 5A). PCR™ products were detected with ethidium bromide staining and then verified by Southern blotting using a DIG-labeled internal oligonucleotide probe (FIG. 5B). The internal oligonucleotide probe used for this blot was found to have no homology to any other sequences by the BLAST homology search. PCR™ assays were repeated at least twice to verify results. RT-PCR™ analysis was also performed on human cancer tissue biopsies that included breast, colon, stomach, pancreas, glioblastoma, and melanoma.

Chromosomal Localization of HOJ-1.

Figure 6A:
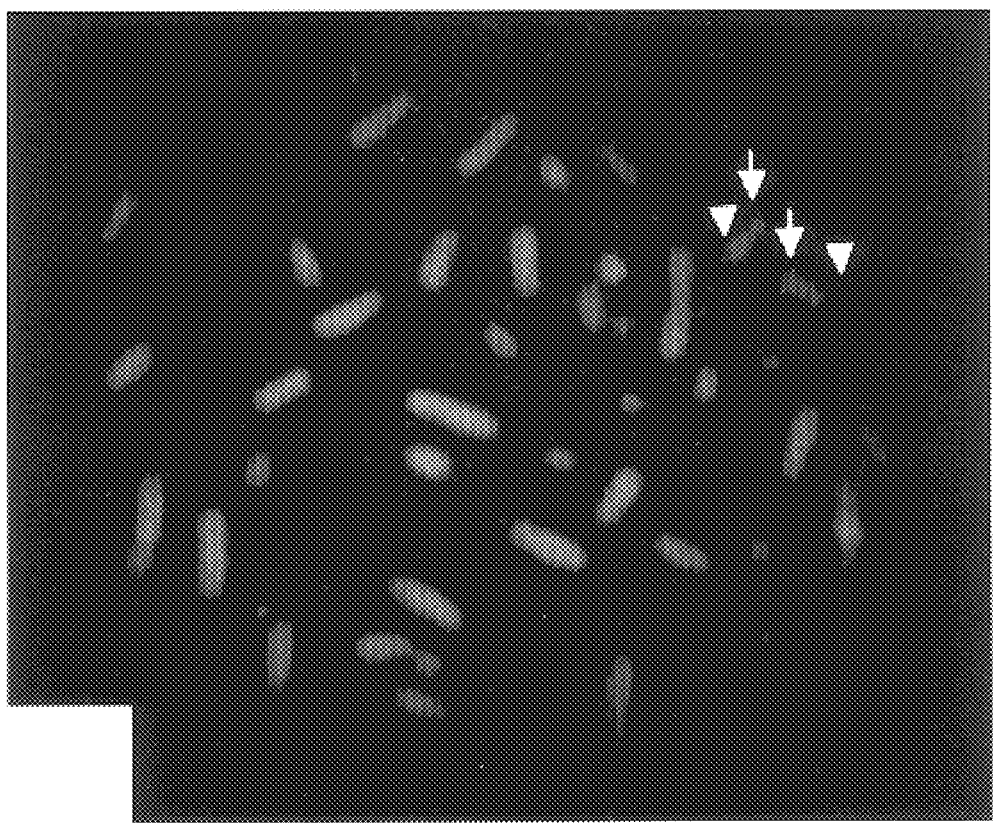
FIG. 6 shows the chromosomal location of HOJ-1.
Figures 1, 2, 6B:
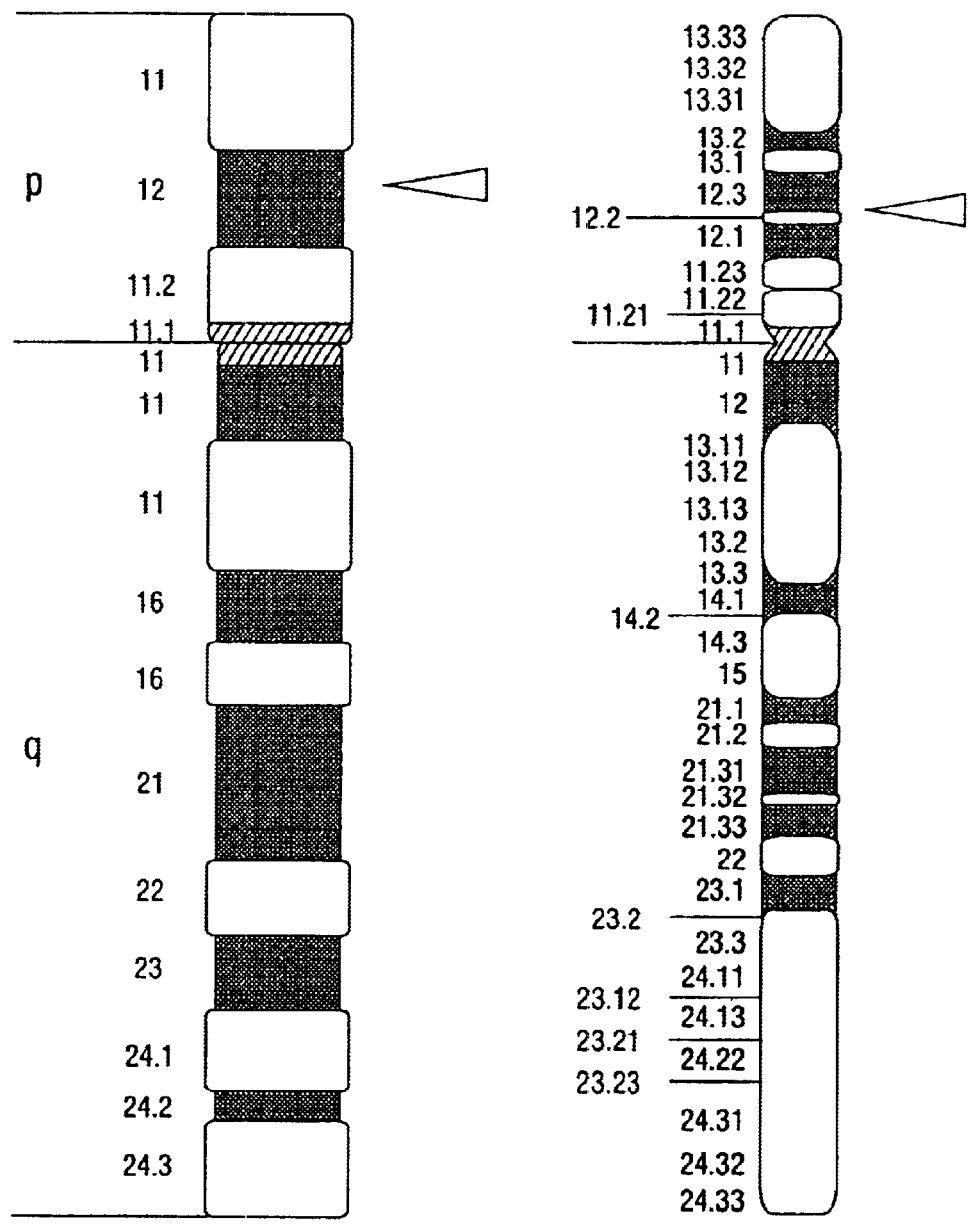

FISH analysis shows that HOJ-1 is located on chromosome 12 where it maps to location 12 p12.3 (FIG. 6A and FIG. 6B). FISH was carried out using a DIG-labeled HOJ-1 probe to screen a P1 human genomic library (Genome Systems, St. Louis, Mo.). The positive P1 clone containing the HOJ-1 gene was cohybridized with a genomic probe which is specific for the long arm of chromosome 12 (FIG. 6A, arrowheads). Measurements of labeled chromosomes mapped HOJ-1 to location 12 p12.3 (FIG. 6A, arrows).

Expression and Purification of Recombinant HOJ-1 Protein.

Figure 2:
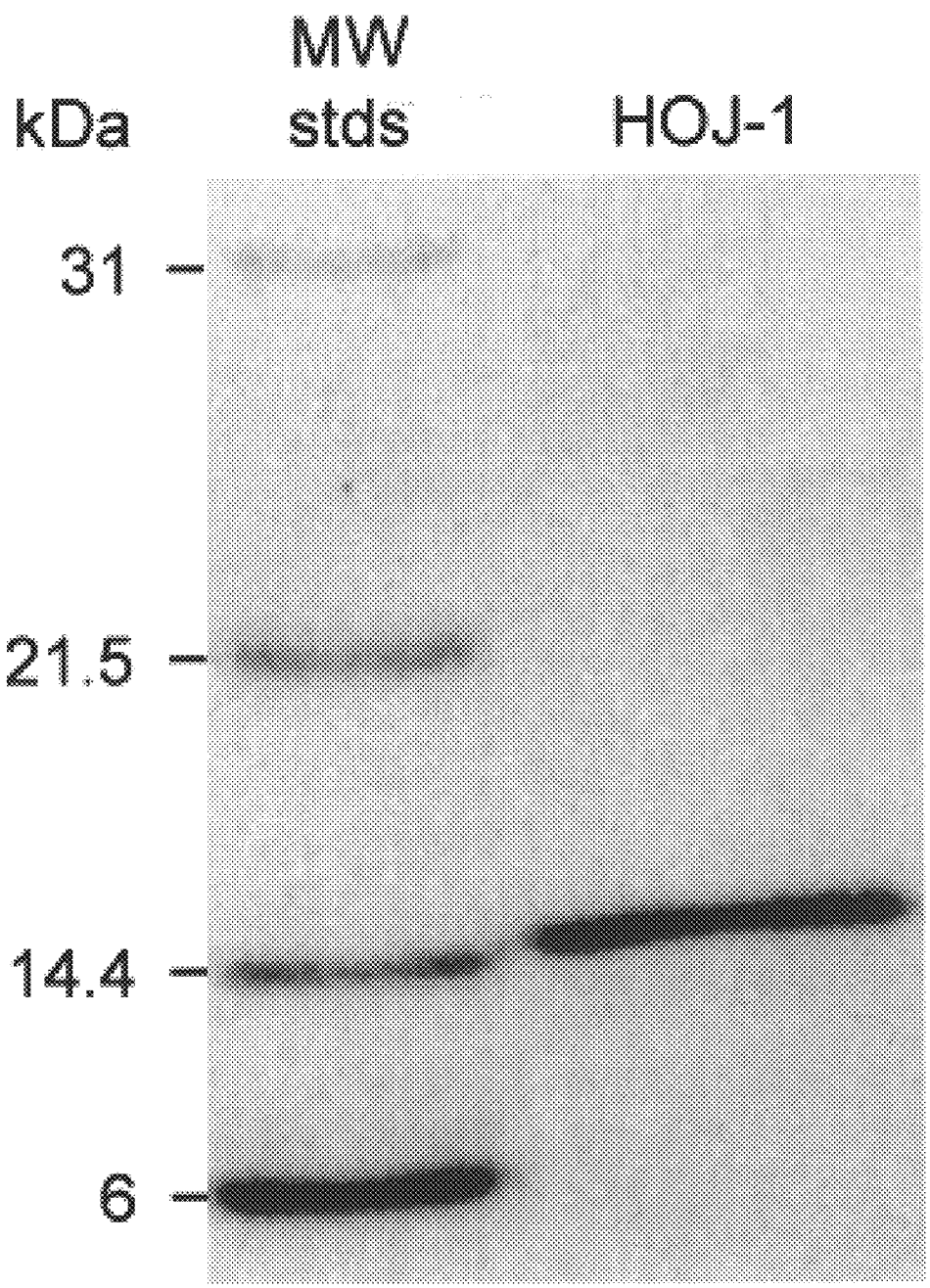
FIG. 2 shows SDS PAGE analysis of purified recombinant HOJ-1. Molecular weight markers are shown on the left lane. HOJ-1 has a molecular mass of 15.4 kDa.

The cDNA encoding ORF of HOJ-1 (109 amino acids) (SEQ ID NO:1), was amplified by PCR™ from the cDNA clone isolated from the two-hybrid system. This cloned sequence was then subcloned into a modified pGEX-2T expression vector and expressed as a GST fusion protein with a hexahistidine tag at the C-terminus (FIG. 1). The intact fusion protein was first purified by glutathion-Sepharose 4B affinity chromatography, and the recombinant HOJ-1 with hexahistidine was cleaved from GST peptide by thrombin protease and then eluted from the column. The HOJ-1 protein was verified by Western blot analysis using an Ni-NTA conjugate antibody (Qiagen, Valencia, Calif.) (FIG. 3) and further purified by SDS-PAGE electrophoresis. The SDS-PAGE analysis (FIG. 2) shows the purified recombinant HOJ-1 has molecular mass of 15.4 kDa.

Western Blot Analysis

Figure 3:
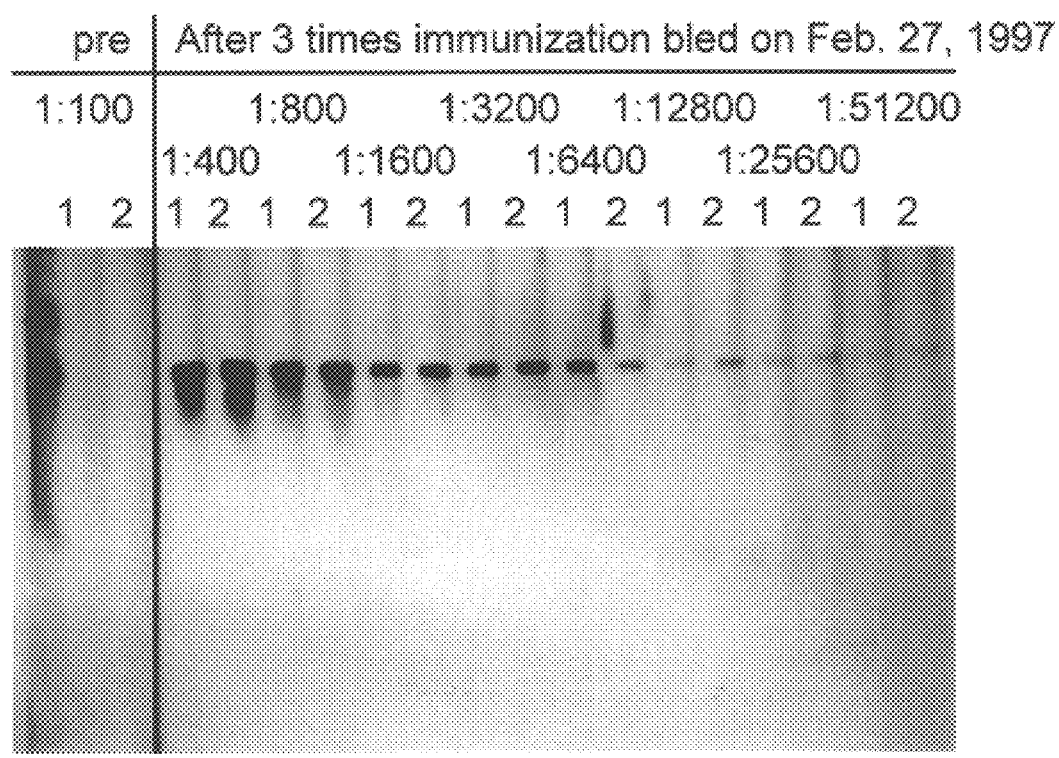
FIG. 3 shows the assessment of HOJ-1 antibody titer in the serum of HOJ-1 immunized rabbit. Serum samples are in duplicated from left to right as follows: preimmunized, 1:100 dilution (lanes 1 and 2); post-immunized serum sample in 2-fold dilution series from 1:400 (lane 3 and 4) to 1:51200 (lane 15 and 16) molecular weight markers shown on the left.

HOJ-1 antibody titers in the serum of HOJ-1 immunized rabbits are shown in FIG. 3.

Detection of HOJ-1 in the blood of Cancer Patients

The absence of HOJ-1 mRNA expression in healthy donor PBL suggests the potential utility of the HOJ-1 gene in detecting circulating cancer cells in the blood. The detection of circulating cancer cells may be clinically beneficial in assessing tumor progression and potential relapse of disease. The RT-PCR™ assay for detection of occult cancer cells in blood using specific markers has provided a new approach to the assessment of cancer progression (Hoon et al., 1995; Kuo et al., 1998). The inventors preliminary data shows that HOJ-1 expression was detected in 2 of 10 PBLs obtained from AJCC stage III and IV breast cancer patients, and in 5 of 10 PBLs from AJCC stage III and IV pancreas cancer patients by RT-PCR™, suggesting that the HOJ-1 gene may be used as a mRNA tumor marker for occult cancer cell detection in blood.

The presence of the HOJ-1 cancer marker in blood (a tissue where normally HOJ-1 is not expressed), allows the detection of occult metastatic cancer cells in the blood of patients with different types of cancer. HOJ-1 mRNA was detected in a RT-PCR™ analysis in the blood of patients suffering from various cancers. HOJ-1 was detected in the blood of 6/13 gastric cancer patients, 6/10 pancreatic cancer patients, 5/20 melanoma cancer patients, 18/20 colon cancer patients and these data are shown in Table 4. Six normal human blood samples were used as negative controls and two cancer cell lines were used positive controls (Table 4).

TABLE 4

| Gastric Cancer Patient Blood | Patient No. | 6/13 (46.2%) |
|---|---|---|
| 1 | 5558 | + |
| 2 | 5559 | − |
| 3 | 5596 | − |
| 4 | 6152 | − |
| 5 | 6153 | + |
| 6 | 6208 | − |
| 7 | 6222 | − |
| 8 | 6223 | − |
| 9 | 7502 | + |
| 10 | 6785 | − |
| 11 | 7807 | + |
| 12 | 7900 | + |
| 13 | 8061 | + |

| Pancreas Cancer Patient Blood | Patient No. | 6/10 (60%) |
|---|---|---|
| 1 | 5163 | + |
| 2 | 6708 | + |
| 3 | 6723 | + |
| 4 | 6836 | + |
| 5 | 6837 | − |
| 6 | 7239 | + |
| 7 | 7605 | + |
| 8 | 7784 | − |
| 9 | 7887 | − |
| 10 | 7945 | − |

| Melanoma Cancer Patient Blood | Patient No. | 5/20 (25%) |
|---|---|---|
| 1 | 1330 | − |
| 2 | 1980 | − |
| 3 | 3976 | − |
| 4 | 3980 | − |
| 5 | 4026 | − |
| 6 | 4028 | − |
| 7 | 4327 | − |
| 8 | 1850 | − |
| 9 | 1578 | − |
| 10 | 4003 | − |
| 11 | 1010 | + |
| 12 | 1013 | + |
| 13 | 1156 | − |
| 14 | 1378 | + |
| 15 | 1993 | − |
| 16 | 3633 | + |
| 17 | 4007 | − |
| 18 | 4009 | − |
| 19 | 4262 | − |
| 20 | 4326 | + |

| Colon Cancer Patient Blood | Patient No. | 18/20 (90%) |
|---|---|---|
| 1 | 8046 | − |
| 2 | 8058 | + |
| 3 | 8095 | + |
| 4 | 8261 | + |
| 5 | 8259 | + |
| 6 | 8513 | + |
| 7 | 8355 | + |
| 8 | 8369 | − |
| 9 | 8481 | + |
| 10 | 8574 | + |
| 11 | 8604 | + |
| 12 | 8746 | + |
| 13 | 8848 | + |
| 14 | 8875 | + |
| 15 | 8920 | + |
| 16 | 8982 | + |
| 17 | 8996 | + |
| 18 | 9011 | + |
| 19 | 9012 | + |
| 20 | 9064 | + |

TABLE 4-continued

| Normal Donor Volunteer Blood | Patient No. | |
|---|---|---|
| 1 | 3330 | − |
| 2 | 3338 | − |
| 3 | 3346 | − |
| 4 | 7218 | − |
| 5 | 7219 | − |
| 6 | 7221 | − |

| Positive Control Cell Line | Patient No. | |
|---|---|---|
| 1 | MCF-7 | + |
| 2 | M12 | + |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abbondanzo et al., *Breast Cancer Res. Treat.*, 16:182(#151), 1990.
Alfthan et al., *Cancer Res.*, 52:4628–4633, 1992.
Allred et al., *Breast Cancer Res. Treat.*, 16:182(#149), 1990.
Altschul et al., *J. Mol. Biol.*, 215:403–410, 1990.
Ando et al., *Int. J. Cancer*, 40:12–17, 1987,
Antibodies: A Laboratory Manual, Cold Spring Harbor Laboratory, Cold Spring Harbor Press, Cold Spring Harbor, N.Y., 1988,
Ausubel, Brent, Kingston, Moore, Seidman, Smith, Struhl, eds., *Current Protocols in Molecular Biology* (Wiley, N.Y.), 1994.
Barany and Merrifield, "The Peptides, Gross and Meienhofer, eds", Academic Press, New York, 1–284, 1979
Basombrio, *Cancer Res.*, 30:2458–2462, 1970.
Bittner et al., *Methods in Enzymol*, 153:516–544, 1987.
Boel et al., *Immunity*, 2(2):167–75, 1995.
Boon et al., *J. Exp. Med.*, 152:1184–1193, 1980.
Boring et al., *Cancer Statistics*, 1994.
Brown et al., *Breast Cancer Res. Treat.*, 16: 192(#191), 1990.
Brunner et al., *J. Immunol.*, 124:1627–1634, 1980.
Bystryn et al., *Cancer Res.*, 45:5603–5607, 1985.
Campbell, In: *Monoclonal Antibody Technology, Laboratory Techniques in Biochemistry and Molecular Biology*, Vol. 13, Burden & Von Knippenberg (Eds.), Elseview, Amsterdam, pp. 71–74; 75–83, 1984.
Capaldi et al., *Biochem. Biophys. Res. Comm.*, 76:425, 1977.
Carubia et al., *Biochem. Biophys. Res. Commun.*, 120:500–504, 1984.
Chen et al., *Proc. Am. Urol. Assn.*, 153: 267A, 1995.
Chien et al., *Proc. Nat'l. Acad. Sci. USA*, 88:9578–9582, 1991.
Chinault and Carbon, *Gene*, 5:111–126, 1979.
Chomczynski and Mackey, *Anal. Biochem.*, 225:163–164, 1995.
Cohen, *Science*, 259:1691–1692, 1993.
Cole et al., *Endocrinology*, 113:1176–1178, 1983.
Cox et al., *J. Virol.*, 67(9):5664–5667, 1993.
Datta et al., *J. Clin. Oncol.*, 12:475–482, 1994.
Denton et al., *J. Pathol*, 167(2):187–91, 1992.
Diamond et al., *J. Urol.*, 128:729–734, 1982.
Donahue et al., *J. Biol. Chem.*, 269: 8604–8609, 1994
Dzau et al., *Proc. Nat'l. Acad. Sci. USA*, 93:11421–11425, 1996.
Elder et al., *Cancer Res.*, 49:5091–5096, 1989.
EP 431,523
EPO 329,822
Fearon et al., *Am J Clin Nutr*, 47 (1):42–48, 1988
Fidler and Hart, *Science*, 217:998–1001, 1982.
Fidler, et al., *Res Immunol.*, 144:(4)284–7; discussion 294–8, 198.
Fink et al., *Genomics*, 29:309–310, 1995.
Fitzpatrick, T. B., In: The American Cancer Society Cancer Handbook. Ch. 30, pp. 532–547, Doubleday & Co., Garden City, N.Y. (Arthur I. Holleb, M. D., ed.) 1986.
Forrest, A. P., *J. Nat'l. Cancer Inst.*, 82:1525, 1990.
Frohman, In: *PCR Protocols: A Guide To Methods And Applications*, Academic Press, N.Y., 1990.
Furukawa et al., *Proc. Nat'l. Acad Sci.* (USA), 90:1972–1976, 1993.
Fynan et al., *Proc. Nat'l. Acad. Sci. USA*, 90:11478–11482, 1993.
Gal et. al., *Lab. Invest.*, 68(1):18, 1993.
Gaugler et al., *J. Exper. Med.*, 179:921–930, 1994.
GB 2,202,328
Gefter et al., *Somatic Cell Genet.*, 3:231–236, 1977
Goding, In: *Monoclonal Antibodies: Principles and Practice*, 2d ed., Academic Press, Orlando, Fla., pp. 65–66, and 71–74, 1986.
Gomella et al., *J. Urolology*, 158:326–337, 1997.
Gross, *Cancer Res.*, 3:326–333, 1943.
Hess et al., *J. Adv. Enzyme Reg.*, 7:149, 1968.
Hewitt et al., *Br J Cancer*, 33 (3) p241–59, 1976.
Hewitt et al., *Br Med J*, 2 (6033):477, 1976.
Hitzeman et al., *J. Biol. Chem.*, 255:2073, 1980.
Holland et al., *Biochemistry*, 17:4900, 1978.
Hollingsworth et al., *Int J Cancer*, 57(2):198–203, 1994.
Hoon et al., *Int J Cancer*, 69(5):369–74, 1996.
Hoon et al., *J. Clin. Oncol.*, 13:2109–2116, 1995.
Hoon et al., *J. Immunol.*, 154:730–737, 1995.
Hoon et al., *J. Urol.*, 150(6):2013–2018, 1993.
Hoon et al., *Int. J. Cancer*, 43:857–862,1989.
Innis et al., *PCR Protocols*, Academic Press, Inc., San Diego Calif., 1990.
Inouye et al., *Nucleic Acids Res.*, 13:3101–3109, 1985.
Irie, In: M. Torisu and T. Yoshida (eds), Basic mechanisms and clinical treatment of tumor metastasis, pp. 371–384, Academic Press, Tokyo, 1985.
Johnson et al., Peptide Turn Mimetics" IN: *Biotechnology And Pharmacy*, Pezzuto et al., eds., Chapman and Hall, New York, 1993.
Jones, *Genetics*, 85: 12, 1977.
Kingsman et al., *Gene*, 7: 141, 1979.
Klein et al., *Cancer Res.*, 20:1561–1572, 1960.
Kohler and Milstein, *Eur. J. Immunol.* 6:511–519, 1976.
Kohler and Milstein, *Nature*, 256:495–497, 1975
Kripke, *J. Nat'l. Canc. Inst.*, 53:333–1336, 1974.
Kuo et al., *Clin. Cancer Res.*, 4:411–418, 1998.
Kwoh et al., *Proc. Nat. Acad. Sci. USA*, 86: 1173, 1989.
Kwon, B. S, *J. Invest. Dermatol.*, 100(2 Suppl): 134S–140S, 1993.

Kyte and Doolittle, *J. Mol. Biol.*, 157:105–132, 1982.
Lehmann et al., *Proc. Nat'l Acad. Sci. USA*, 86:9891–9895, 1989.
Lehmann, et al., *Cancer Res.*, 47:841–845, 1987.
Levy et al., *Adv. Cancer Res.*, 24:1–59, 1977.
Li et al., *Nature*, 378: 398–402, 1995.
Liang and Pardee, *Science*, 257: 967–971, 1992.
Liang et al., *Cancer Res.*, 52:6966–6968, 1992.
Lin and Guidotti, *J. Biol. Chem.*, 264:14408–14414, 1989.
Lowy et al., *Cell*, 22: 17, 1980.
Madersbacher et al., *Cancer Res.*, 54:5096–5100, 1994.
Marcillac et al., *Cancer Res.*, 52:3901–3907, 1992.
Maryanski et al., *Eur. J. Immunol.*, 124:1627–1634, 1980.
Maryanski et al., *Eur. J. Immunol.*, 12:406–412, 1982.
McManus et al., *Cancer Res.*, 36:3476–3481, 1976.
Melcher and Johnson, *Mol. Cell Biol.*, 15:2839–2848, 1995.
Mencinger et al., *Biochim. Biophys. Acta*, 1395:176–180, 1998.
Merrifield, *Science*, 232: 341–347, 1986.
Mok et al., *Gynecol. Oncol.*, 52: 247–252, 1994.
Morton et al., *Cancer*, 71:3737–3743, 1993.
Mosmann, *J. Immunol. Methods*, 65:55–63, 1983.
Mulligan, *Science*, 260:926–932, 1993.
Nagata et al., *J. Biol. Chem*, 267:12082–12089, 1992.
Nakamura et al., In: *Handbook of Experimental Immunology* (4th Ed.), Weir, E., Herzenberg, L. A., Blackwell, C., Herzenberg, L. (eds). Vol. 1, Chapter 27, Blackwell Scientific Publ., Oxford, 1987.
Natali et al., *Cancer*, 59:55–63, 1987.
Nordlund et al., *J. Invest. Dermatol,.* 92:53S–60S, 1989.
Nowell, P. C. Genetic instability in cancer cells: relationship to tumor cell heterogeneity. *TUMOR CELL HETEROGENEITY*, Owens, A. H., Coffey, D. S., Baylin, S. B. (eds.). New York, Academic Press (1982) pp. 351–365.
O'Hare et al., *Proc. Nat'l Acad. Sci. USA*, 78: 1527, 1981.
Ohara et al., *Proc. Nat'l Acad. Sci. USA*, 86: 5673–5677, 1989.
Palladino et al., *Canc. Res.*, 47:5074–5079, 1987.
PCT/US87/00880
PCT/US89/01025
Pinkel, et a., *Proc Nat'l Acad Sci USA*, 83(9):2934–8, 1986.
Prehn, et al., *J. Nat'l. Canc. Inst.*, 18:769–778, 1957.
Remington's Pharmaceutical Sciences, 15th ed., pp. 1035–1038 and 1570–1580; 624–652.
Robbins et al., *Cancer Res*, 54(12):3124–6, 1994.
Robzyk and Kassir, "A simple and highly efficient procedure for rescuing autonomous plasmids from yeast," *Nucl. Acids Res.*, 20:3790 , 1992.
Rubinstein et al.,*J. Nat'l. Cancer Inst.*, 82:1113–1120, 1990.
Sager et al., *FASEB J.*, 7:964–970, 1993.
Sambrook et al., *Molecular Cloning*, 2nd ed., Cold Spring Harbor Laboratory Press, CSH, 1.38–1.39, 1989.
Santerre et al., *Gene*, 30:147, 1984.
Sarantou et al., *Cancer Res*, 57(7):1371–6, 1997.
See Hewitt, et al., *Brit. J. Cancer*, 33:241–259, 1976.
Serrano et al., *Nature*, 366:704–707, 1993.
Serrano et al., *Science*, 267:249–252, 1995.
Smith and Johnson, "Single-step purification of polypeptides expressed in *Escherichia Coli* as fusions with glutathione S-transferase," *Gene*, 67:31–40, 1988.
Stewart and Young, Solid Phase Peptide Synthesis, 2d. ed., Pierce Chemical Co., 1984.
Stinchcomb et al., *Nature*, 282: 39, 1979.
Sun and Cohen, *Gene*, 137:127–132, 1993.
Szybalska et al, *Proc. Nat'l Acad. Sci. USA*, 48:2026, 1962.
Talmadge et al., *Nature*, 307:37–40, 1984.
Tam et al., *J. Am. Chem. Soc.*, 105:6442, 1983.
Tang et al., *Nature*, 356:152–154, 1992.
Traversari et al., *Immunogenetics*, 35(3):145–52, 1992.
Traversari et al , *J Exp Med.*, 176(5):1453–7, 1992.
Tschemper et al., *Gene*, 10: 157, 1980.
Tsuchida et al., *J. Nat'l. Cancer Inst.*, 78:45–54, 1987a.
Tsuchida et al., *J. Nat'l. Cancer Inst.*, 78:55–60, 1987b.
U.S. Pat. No. 4,883,750
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,215,051
U.S. Pat. No. 4,275,149
U.S. Pat. No. 4,277,437
U.S. Pat. No. 4,340,535
U.S. Pat. No. 4,366,241
U.S. Pat. No. 4,472,509
U.S. Pat. No. 4,472,509
U.S. Pat. No. 4,554,101
U.S. Pat. No. 4,682,195
U.S. Pat. No. 4,683,195
U.S. Pat. No. 4,683,202
U.S. Pat. No. 4,740,463
U.S. Pat. No. 4,800,159
U.S. Pat. No. 4,816,567
U.S. Pat. No. 4,867,973
U.S. Pat. No. 5,021,236
U.S. Pat. No. 5,138,045
U.S. Pat. No. 5,262,311
U.S. Pat. No. 5,279,721
U.S. Pat. No. 5,342,774
U.S. Pat. No. 5,565,332
U.S. Pat. No. 5,633,365
U.S. Pat. No. 5,665,549
U.S. Pat. No. 5,693,762
Ulmer et al., *Science*, 259:1745–1749, 1993.
Van den Eynde, et al., *Biochem Soc Trans*, 23(3):681–6, 1995.
Van den Eynde et al., *J Exp Med*, 182(3):689–98, 1995.
Van Der Bruggen, Traversari, Chomez, Lurquin, De Plaen, Van Den Eynde, Knuth, Boon, "A gene encoding an antigen recognized by cytolytic T lymphocytes on a human melanoma," *Science*, 254:1643–1647, 1991.
Van Pel et al., *J. Exp. Med.*, 157:1992–2001, 1983.
Vijayasardahi et al., *J Experimental Medicine*, 171(4):1375–1380, 1990.
Visualization of Nucleic Acids" Gerad Morell Ed., CRC publ., 1995.
Wagner et al., *Science*, 260:1510–1513, 1993.
Walker et al., *Proc. Nat'l Acad. Sci. USA*, 89:392–396 1992.
Wang et al, In: *Animal Cell Technology: Basic & Applied Aspects*, S. Kaminogawa et al., (eds), vol. 5, pp463–469, Kluwer Academic Publishers, Netherlands, 1993.
Watson et al., *Cancer Res.*, 54:4598–4602, 1994.
Weitzel and Patel, *GATA*, 11(5–6) 165–170, 1994.
Weitzel et al., *Genomics*, 14:309–319, 1992.
Welsh et al., *Nucleic Acids Res.*, 20:4965–4970, 1992.
Whitton et al., *J. Virol.*, 67:(1)348–352, 1993.
Wigler et al., *Cell*, 11:223, 1977.
Wigler et al., *Proc. Nat'l Acad. Sci. USA*, 77:3567, 1980.
WO 88/10315
WO 89/06700
WO 94/10343
WO 94/23050
WO 95/10265
Wong et al., *Int. J. Oncol.*, 3: 13–17, 1993.
Wu et al., *Genomics*, 4:560, 1989
Yamaguchi et al., *Br. J. Cancer*, 60:382–384, 1989.
Yoshimura et al., *Cancer*, 73:2745–2752, 1994.
Zhu et al., *Biochem. Mol. Biol. Int.*, 42:927–935, 1997.

What is claimed is:

1. An isolated DNA segment that encodes a HOJ-1 polypeptide comprising the amino acid sequence of SEQ ID NO:2.

2. The isolated DNA segment of claim 1, comprising the nucleic acid sequence of SEQ ID NO:1.

3. The isolated DNA segment of claim 1, wherein the DNA segment is positioned under the control of a promoter.

4. The isolated DNA segment of claim 1, further defined as a recombinant vector.

5. An isolated recombinant host cell comprising an isolated DNA segment that comprises a DNA segment that encodes a HOJ-1 protein comprising the amino acid sequence of SEQ ID NO:2.

6. The recombinant host cell of claim 5, further defined as a prokaryotic host cell.

7. The recombinant host cell of claim 5, further defined as a eukaryotic host cell.

8. The recombinant host cell of claim 5, wherein the DNA segment is introduced into the cell by means of a recombinant vector.

9. The recombinant host cell of claim 5, wherein the DNA segment has the sequence of SEQ ID NO:1.

10. An isolated nucleic acid segment or 14 to no more than 100 contiguous nucleotides from bases 1–868 of SEQ ID NO:1, or the fill complement thereof, wherein the complement is a contiguous segment of 14 to no more than 100 nucleotides.

11. The isolated nucleic acid segment of claim 10, wherein said isolated nucleic acid segment is 20 to no more than 100 contiguous nucleotides from bases 1–868 of SEQ ID NO:1, or the full complement thereof, wherein the complement is a contiguous segment of 20 to no more than 100 nucleotides.

12. The isolated nucleic acid segment of claim 10, wherein said isolated nucleic acid segment is 25 to no more than 100 contiguous nucleotides from bases 1–868 of SEQ ID NO:1, or the full complement thereof, wherein the complement is a contiguous segment of 25 to no more than 100 nucleotides.

13. The isolated nucleic acid segment of claim 10, further defined as a DNA segment.

14. The isolated nucleic acid segment of claim 10, further defined as a RNA segment.

15. The isolated DNA segment of claim 1, further comprising an origin of replication.

16. A bacterial vector or a plasmid vector that comprises the DNA segment of claim 15.

17. The isolated DNA segment of claim 1, further comprising a polyadenylation signal operably linked to the segment encoding HOJ-1.

18. The isolated DNA segment of claim 15, wherein said DNA segment is a viral vector selected from the group consisting of retrovirus, adenovirus, herpesvirus, vaccinia virus, pox-virus and adeno-associated virus.

19. A composition of matter comprising a DNA segment that encodes a HOJ-1 polypeptide comprising the amino acid sequence of SEQ ID NO:2 packaged in a virus particle.

20. A composition of matter comprising a DNA segment that encodes a HOJ-1 polypeptide comprising the amino acid sequence of SEQ ID NO:2 packaged in a liposome.

* * * * *

UNITED STATES PATENT AND TRADEMARK OFFICE
CERTIFICATE OF CORRECTION

PATENT NO. : 6,673,914 B1 Page 1 of 1
DATED : January 6, 2004
INVENTOR(S) : David S. B. Hoon It is certified that error appears in the above-identified patent and that said Letters Patent is hereby corrected as shown below:

<u>Title page,</u>
Item [54], Title, please insert -- A NEW -- before "HUMAN" therefor.

<u>Column 91,</u>
Line 39, please delete "or" and insert -- of -- therefor.
Line 41, please delete "fill" and insert -- full -- therefor.

Signed and Sealed this

Eleventh Day of May, 2004

JON W. DUDAS
*Acting Director of the United States Patent and Trademark Office*